United States Patent
Mingozzi et al.

(10) Patent No.: US 12,171,843 B2
(45) Date of Patent: Dec. 24, 2024

(54) HYBRID REGULATORY ELEMENTS

(71) Applicants: GENETHON, Evry (FR); INSTITUT NATIONAL DE LA SANTÉ ET DE LA RECHERCHE MÉDICALE, Paris (FR); SORBONNE UNIVERSITÉ, Paris (FR); UNIVERSITE D'EVRY VAL D'ESSONNE, Evry (FR); ASSOCIATION INSTITUT DE MYOLOGIE, Paris (FR)

(72) Inventors: Federico Mingozzi, Paris (FR); Pasqualina Colella, Naples (IT)

(73) Assignees: GENETHON, Evry (FR); INSTITUT NATIONAL DE LA SANTÉ ET DE LA RECHERCHE MÉDICALE (INSERM), Paris (FR); SORBONNE UNIVERSITÉ, Paris (FR); UNIVERSITE D'EVRY VAL D'ESSONNE, Evry (FR); ASSOCIATION INSTITUT DE MYOLOGIE, Paris (FR)

( * ) Notice: Subject to any disclaimer, the term of this patent is extended or adjusted under 35 U.S.C. 154(b) by 696 days.

(21) Appl. No.: 16/968,196

(22) PCT Filed: Feb. 7, 2019

(86) PCT No.: PCT/EP2019/053061
§ 371 (c)(1),
(2) Date: Aug. 7, 2020

(87) PCT Pub. No.: WO2019/154939
PCT Pub. Date: Aug. 15, 2019

(65) Prior Publication Data
US 2021/0346519 A1 Nov. 11, 2021

Related U.S. Application Data

(60) Provisional application No. 62/627,442, filed on Feb. 7, 2018.

(30) Foreign Application Priority Data

Mar. 14, 2018 (EP) .................................... 18161872
Jun. 20, 2018 (EP) .................................... 18178853

(51) Int. Cl.
*A61K 48/00* (2006.01)
*C12N 15/86* (2006.01)
*C12Q 1/68* (2018.01)

(52) U.S. Cl.
CPC .......... *A61K 48/0058* (2013.01); *C12N 15/86* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

2021/0162073 A1* 6/2021 Gray .................... A61K 48/005

FOREIGN PATENT DOCUMENTS

| EP | 1 310 561 | 5/2003 |
|----|-----------|--------|
| EP | 2 500 428 | 9/2012 |
| JP | 2007319073 | 12/2007 |
| WO | WO 01/027303 | 4/2001 |
| WO | WO 02/02765 | 1/2002 |
| WO | WO 02/095006 | 11/2002 |
| WO | WO 2004/087926 | 10/2004 |
| WO | WO 2006/096815 | 9/2006 |
| WO | WO 2009/130208 | 10/2009 |
| WO | WO 2015/110449 | 7/2015 |
| WO | WO 2015/196179 | 12/2015 |

OTHER PUBLICATIONS

Rasowo et al. European Scientific Journal vol. 10(18):23-37, Jun. 2014.*
Lam et al. Molecular Therapy vol. 15(6):1129-1136, Jun. 2007.*
Appleby, C. E. et al. "A novel combination of promoter and enhancers increases transgene expression in vascular smooth muscle cells in vitro and coronary arteries in vivo after adenovirus-mediated gene transfer" *Gene Therapy*, 2003, pp. 1616-1622, vol. 10, No. 18.
Davis, J. J. et al. "Oncolysis and suppression of tumor growth by a GFP-expressing oncolytic adenovirus controlled by an hTERT and CMV hybrid promoter" *Cancer Gene Therapy*, 2006, pp. 1-4.
Frauli, M. et al. "Adenoviral-mediated skeletal muscle transcriptional targeting using chimeric tissue-specific promoters" *Med Sci Monit*, 2003, pp. BR78-BR84, vol. 9, No. 2.
Hagstrom, J. N. et al. "Improved muscle-derived expression of human coagulation factor IX from a skeletal actin/CMV hybrid enhancer/promoter" *Blood*, Apr. 15, 2000, pp. 2536-2542, vol. 95, No. 8.
Kiang, A. et al. "Fully Deleted Adenovirus Persistently Expressing GAA Accomplishes Long-Term Skeletal Muscle Glycogen Correction in Tolerant and Nontolerant GSD-II Mice" *Molecular Therapy*, Jan. 2006, pp. 127-134, vol. 13, No. 1.
Kim, Y.-H. et al. "Image-aided Suicide Gene Therapy Utilizing Multifunctional hTERT-targeting Adenovirus for Clinical Translation in Hepatocellular Carcinoma" *Theranostics*, 2016, pp. 357-368, vol. 6, Issue 3.
Lam, P. Y.-P. et al. "An Efficient and Safe Herpes Simplex Virus Type 1 Amplicon Vector for Transcriptionally Targeted Therapy of Human Hepatocellular Carcinomas" *Molecular Therapy*, Jun. 2007, pp. 1129-1136, vol. 15, No. 6.

(Continued)

*Primary Examiner* — Sean McGarry
(74) *Attorney, Agent, or Firm* — SALIWANCHIK, LLOYD & EISENSCHENK

(57) ABSTRACT

The present invention relates to hybrid transcription regulatory elements to drive gene expression, in particular hybrid promoters, designed by the fusion of at least two transcription regulatory elements with different tissue selectivity, such as two promoters driving expression in different tissues in a tissue-selective manner.

13 Claims, 30 Drawing Sheets

Figure 1:
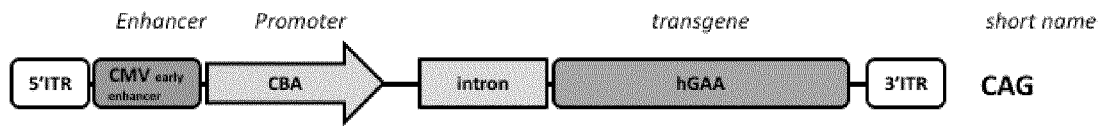

Specification includes a Sequence Listing.

(56) References Cited

OTHER PUBLICATIONS

Ribault, S. et al. "Chimeric Smooth Muscle-Specific Enhancer/Promoters, Valuable Tools for Adenovirus-Mediated Cardiovascular Gene Therapy" Circulation Research, Mar. 16, 2001, pp. 468-475, vol. 88, No. 1.
Written Opinion in International Application No. PCT/EP2019/053061, Mar. 1, 2019, pp. 1-10.
Van Hove, J.L.K. et al. "High-level production of recombinant human lysosomal acid a-glucosidase in Chinese hamster ovary cells which targets to heart muscle and corrects glycogen accumulation in fibroblasts from patients with Pompe disease" *Proc Natl. Acad. Sci. USA*, Jan. 1996, pp. 65-70, vol. 93.
Egawa, T. et al. "The role of the Runx transcription factors in thymocyte differentiation and in homeostasis of naive T cells" *J Exp Med*, Aug. 2007, pp. 1945-1957, vol. 204, No. 8.

\* cited by examiner

A

B

C

D

E

```
                         SEQUENCE LISTING

<160> NUMBER OF SEQ ID NOS: 25

<210> SEQ ID NO 1
<211> LENGTH: 358
<212> TYPE: DNA
<213> ORGANISM: artificial
<220> FEATURE:
<223> OTHER INFORMATION: spC5.12 promoter

<400> SEQUENCE: 1
caccgcggtg gcggccgtcc gccctcggca ccatcctcac gacacccaaa tatggcgacg      60
ggtgaggaat ggtggggagt tattttaga gcggtgagga aggtgggcag gcagcaggtg     120
ttggcgctct aaaaataact cccgggagtt attttagag cggaggaatg gtggacaccc     180
aaatatggcc acggttcctc acccgtcgcc atatttgggt gtccgccctc ggccggggcc     240
gcattcctgg gggccgggcg gtgctcccgc ccgcctcgat aaaaggctcc ggggccggcg     300
gcggcccacg agctacccgg aggagcggga ggcgccaagc tctagaacta gtggatct      358

<210> SEQ ID NO 2
<211> LENGTH: 397
<212> TYPE: DNA
<213> ORGANISM: artificial
<220> FEATURE:
<223> OTHER INFORMATION: hAAT promoter

<400> SEQUENCE: 2
gatcttgcta ccagtggaac agccactaag gattctgcag tgagagcaga gggccagcta      60
agtggtactc tcccagagac tgtctgactc acgccacccc ctccaccttg gacacaggac     120
gctgtggttt ctgagccagg tacaatgact cctttcggta agtgcagtgg aagctgtaca     180
ctgcccaggc aaagcgtccg ggcagcgtag gcgggcgact cagatcccag ccagtggact     240 tagccctgt ttgctcctcc gataactggg gtgaccttgg ttaatattca ccagcagcct     300 ccccgttgc ccctctggat ccactgctta aatacgacg aggacagggc cctgtctcct     360
cagcttcagg caccaccact gacctgggac agtgaat                            397

<210> SEQ ID NO 3
<211> LENGTH: 468
```

```
<212> TYPE: DNA
<213> ORGANISM: artificial
<220> FEATURE:
<223> OTHER INFORMATION: hSYN promoter

<400> SEQUENCE: 3
tgcagagggc cctgcgtatg agtgcaagtg ggttttagga ccaggatgag gcggggtggg      60
ggtgcctacc tgacgaccga ccccgaccca ctggacaagc acccaacccc cattccccaa    120
attgcgcatc ccctatcaga gaggggagg ggaaacagga tgcggcgagg cgcgtgcgca     180
ctgccagctt cagcaccgcg gacagtgcct tcgccccgc ctggcggcgc gcgccaccgc     240
cgcctcagca ctgaaggcgc gctgacgtca ctcgccggtc ccccgcaaac tccccttccc    300
ggccaccttg gtcgcgtccg cgccgccgcc ggcccagccg gaccgcacca cgcgaggcgc    360
gagatagggg ggcacgggcg cgaccatctg cgctgcggcg ccggcgactc agcgctgcct    420
cagtctgcgg tgggcagcgg aggagtcgtg tcgtgcctga gagcgcag                 468

<210> SEQ ID NO 4
<211> LENGTH: 321
<212> TYPE: DNA
<213> ORGANISM: artificial
<220> FEATURE:
<223> OTHER INFORMATION: ApoE enhancer

<400> SEQUENCE: 4
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg g                                              321

<210> SEQ ID NO 5
<211> LENGTH: 683
<212> TYPE: DNA
<213> ORGANISM: artificial
<220> FEATURE:
<223> OTHER INFORMATION: Enh.C5.12
<220> FEATURE:
<221> NAME/KEY: misc_feature
<222> LOCATION: (1)..(321)
<223> OTHER INFORMATION: ApoE enhancer
<220> FEATURE:
<221> NAME/KEY: misc_feature
<222> LOCATION: (322)..(325)
<223> OTHER INFORMATION: linker
<220> FEATURE:
<221> NAME/KEY: misc_feature
<222> LOCATION: (326)..(683)
<223> OTHER INFORMATION: spC5.12 promoter

<400> SEQUENCE: 5
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg ggtaccaccg cggtggcggc cgtccgccct cggcaccatc    360
```

```
ctcacgacac ccaaatatgg cgacgggtga ggaatggtgg ggagttattt ttagagcggt      420
gaggaaggtg ggcaggcagc aggtgttggc gctctaaaaa taactcccgg gagttatttt      480
tagagcggag gaatggtgga cacccaaata tggcgacggt tcctcacccg tcgccatatt      540
tgggtgtccg ccctcggccg gggccgcatt cctgggggcc gggcggtgct cccgcccgcc      600
tcgataaaag gctccggggc cggcggcggc ccacgagcta cccggaggag cgggaggcgc      660
caagctctag aactagtgga tct                                              683
```

<210> SEQ ID NO 6
<211> LENGTH: 1121
<212> TYPE: DNA
<213> ORGANISM: artificial
<220> FEATURE:
<223> OTHER INFORMATION: LiMP
<220> FEATURE:
<221> NAME/KEY: misc_feature
<222> LOCATION: (1)..(321)
<223> OTHER INFORMATION: ApoE enhancer
<220> FEATURE:
<221> NAME/KEY: misc_feature
<222> LOCATION: (322)..(330)
<223> OTHER INFORMATION: linker
<220> FEATURE:
<221> NAME/KEY: misc_feature
<222> LOCATION: (331)..(727)
<223> OTHER INFORMATION: hAAT promoter
<220> FEATURE:
<221> NAME/KEY: misc_feature
<222> LOCATION: (728)..(763)
<223> OTHER INFORMATION: linker
<220> FEATURE:
<221> NAME/KEY: misc_feature
<222> LOCATION: (764)..(1121)
<223> OTHER INFORMATION: spC5.12 promoter

<400> SEQUENCE: 6

```
aggctcagag gcacacagga gtttctgggc tcaccctgcc cccttccaac ccctcagttc       60
ccatcctcca gcagctgttt gtgtgctgcc tctgaagtcc acactgaaca aacttcagcc      120
tactcatgtc cctaaaatgg gcaaacattg caagcagcaa acagcaaaca cacagccctc      180
cctgcctgct gaccttggag ctggggcaga ggtcagagac ctctctgggc ccatgccacc      240
tccaacatcc actcgacccc ttggaatttc ggtggagagg agcagaggtt gtcctggcgt      300
ggtttaggta gtgtgagagg ggtacccggg gatcttgcta ccagtggaac agccactaag      360
gattctgcag tgagagcaga gggccagcta agtggtactc tcccagagac tgtctgactc      420
acgccacccc ctccaccttg gacacaggac gctgtggttt ctgagccagg tacaatgact      480
cctttcggta agtgcagtgg aagctgtaca ctgcccaggc aaagcgtccg ggcagcgtag      540
gcgggcgact cagatcccag ccagtggact tagcccctgt ttgctcctcc gataactggg      600
gtgaccttgg ttaatattca ccagcagcct ccccgttgc ccctctggat ccactgctta      660 aatacgacg aggacagggc cctgtctcct cagcttcagg caccaccact gacctgggac       720
agtgaataga tcctgagaac ttcagggtga gtctatggga ccccaccgcg gtggcggccg      780
tccgccctcg gcaccatcct cacgacaccc aaatatggcg acgggtgagg aatggtgggg      840
agttattttt agagcggtga ggaaggtggg caggcagcag gtgttggcgc tctaaaaata      900
actcccggga gttattttta gagcggagga atggtggaca cccaaatatg gcgacggttc      960
ctcacccgtc gccatatttg gtgtccgcc ctcggccggg gccgcattcc tgggggccgg     1020
gcggtgctcc cgcccgcctc gataaaaggc tccggggccg gcggcggccc acgagctacc     1080
cggaggagcg ggaggcgcca agctctagaa ctagtggatc t                         1121
```

<210> SEQ ID NO 7
<211> LENGTH: 1231
<212> TYPE: DNA
<213> ORGANISM: artificial
<220> FEATURE:
<223> OTHER INFORMATION: LiNeuP
<220> FEATURE:
<221> NAME/KEY: misc_feature
<222> LOCATION: (1)..(321)
<223> OTHER INFORMATION: ApoE enhancer
<220> FEATURE:
<221> NAME/KEY: misc_feature
<222> LOCATION: (322)..(330)
<223> OTHER INFORMATION: linker
<220> FEATURE:
<221> NAME/KEY: misc_feature
<222> LOCATION: (331)..(727)
<223> OTHER INFORMATION: hAAT promoter
<220> FEATURE:
<221> NAME/KEY: misc_feature
<222> LOCATION: (728)..(763)
<223> OTHER INFORMATION: linker
<220> FEATURE:
<221> NAME/KEY: misc_feature
<222> LOCATION: (764)..(1231)
<223> OTHER INFORMATION: hSYN promoter

<400> SEQUENCE: 7

```
aggctcagag gcacacagga gtttctgggc tcaccctgcc ccttccaac ccctcagttc      60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg ggtacccggg gatcttgcta ccagtggaac agccactaag    360
gattctgcag tgagagcaga gggccagcta agtggtactc tcccagagac tgtctgactc    420
acgccacccc ctccaccttg gacacaggac gctgtggttt ctgagccagg tacaatgact    480
cctttcggta agtgcagtgg aagctgtaca ctgcccaggc aaagcgtccg ggcagcgtag    540
gcgggcgact cagatcccag ccagtggact tagcccctgt ttgctcctcc gataactggg    600
gtgaccttgg ttaatattca ccagcagcct ccccgttgc ccctctggat ccactgctta    660
aatacggacg aggacagggc cctgtctcct cagcttcagg caccaccact gacctgggac    720
agtgaataga tcctgagaac ttcagggtga gtctatggga ccctgcagag ggccctgcgt    780
atgagtgcaa gtgggtttta ggaccaggat gaggcggggt ggggggtgcct acctgacgac    840
cgaccccgac ccactggaca agcacccaac ccccattccc caaattgcgc atcccctatc    900
agagagggg aggggaaaca ggatgcgcg aggcgcgtgc gcactgccag cttcagcacc    960
gcggacagtg ccttcgcccc cgcctggcgg cgcgcgccac cgccgcctca gcactgaagg   1020
cgcgctgacg tcactcgccg gtcccccgca aactccccctt ccggccacc ttggtcgcgt  1080
ccgcgccgcc gccggcccag ccggaccgca ccacgcgagg gcgagatag gggggcacgg   1140
gcgcgaccat ctgcgctgcg gcgccggcga ctcagcgctg cctcagtctg cggtgggcag   1200
cggaggagtc gtgtcgtgcc tgagagcgca g                                  1231
```

<210> SEQ ID NO 8
<211> LENGTH: 23
<212> TYPE: DNA
<213> ORGANISM: artificial
<220> FEATURE:

```
<223> OTHER INFORMATION: primer

<400> SEQUENCE: 8
tctagttgcc agccatctgt tgt                                             23

<210> SEQ ID NO 9
<211> LENGTH: 18
<212> TYPE: DNA
<213> ORGANISM: artificial
<220> FEATURE:
<223> OTHER INFORMATION: primer

<400> SEQUENCE: 9
tgggagtggc accttcca                                                   18

<210> SEQ ID NO 10
<211> LENGTH: 22
<212> TYPE: DNA
<213> ORGANISM: artificial
<220> FEATURE:
<223> OTHER INFORMATION: primer

<400> SEQUENCE: 10
agatacgccg gacattggac tg                                              22

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
gcacgcccag cagattgaac                                                 20

<210> SEQ ID NO 12
<211> LENGTH: 19
<212> TYPE: DNA
<213> ORGANISM: artificial
<220> FEATURE:
<223> OTHER INFORMATION: probe

<400> SEQUENCE: 12
gtgtggtcct cttgggagc                                                  19

<210> SEQ ID NO 13
<211> LENGTH: 612
<212> TYPE: DNA
<213> ORGANISM: artificial
<220> FEATURE:
<223> OTHER INFORMATION: E-Syn promoter

<400> SEQUENCE: 13
cactacgggt ctaggctgcc catgtaagga ggcaaggcct ggggacaccc gagatgcctg      60
gttataatta accccaacac ctgctgcccc cccccccca acacctgctg cctgagcctg     120
agcggttacc ccaccccggt gcctgggtct taggctctgt acaccatgga ggagaagctc    180
gctctaaaaa taaccctgtc cctggtggcg cgccgagctc caccgcggtg gcggccgtcc    240
gccctcggca ccatcctcac gacacccaaa tatggcgacg ggtgaggaat ggtggggagt    300 tattttttaga gcggtgagga aggtgggcag gcagcaggtg ttggcgctct aaaaataact    360
cccgggagtt atttttagag cggaggaatg gtggacaccc aaatatggcc caaatatggc    420
gacggttcct caccgtcgc catatttggg tgtccgccct cggccggggc cgcattcctg    480
```

-continued

```
ggggccgggc ggtgctcccg cccgcctcga taaaaggctc cggggccggc ggcggcccac    540
gagctacccg gaggagcggg aggcgccaag ctctagaact agtggatccc ccgggctgca    600
ggaattcgat at                                                        612
```

<210> SEQ ID NO 14
<211> LENGTH: 925
<212> TYPE: PRT
<213> ORGANISM: artificial
<220> FEATURE:
<223> OTHER INFORMATION: hGAA polypeptide (wt w/o sp)

<400> SEQUENCE: 14

Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
            20                  25                  30

Ala Ser Arg Pro Gly Pro Arg Asp Ala Gln Ala His Pro Gly Arg Pro
        35                  40                  45

Arg Ala Val Pro Thr Gln Cys Asp Val Pro Pro Asn Ser Arg Phe Asp
    50                  55                  60

Cys Ala Pro Asp Lys Ala Ile Thr Gln Glu Gln Cys Glu Ala Arg Gly
65                  70                  75                  80

Cys Cys Tyr Ile Pro Ala Lys Gln Gly Leu Gln Gly Ala Gln Met Gly
                85                  90                  95

Gln Pro Trp Cys Phe Phe Pro Pro Ser Tyr Pro Ser Tyr Lys Leu Glu
            100                 105                 110

Asn Leu Ser Ser Ser Glu Met Gly Tyr Thr Ala Thr Leu Thr Arg Thr
        115                 120                 125

Thr Pro Thr Phe Phe Pro Lys Asp Ile Leu Thr Leu Arg Leu Asp Val
    130                 135                 140

Met Met Glu Thr Glu Asn Arg Leu His Phe Thr Ile Lys Asp Pro Ala
145                 150                 155                 160

Asn Arg Arg Tyr Glu Val Pro Leu Glu Thr Pro His Val His Ser Arg
                165                 170                 175

Ala Pro Ser Pro Leu Tyr Ser Val Glu Phe Ser Glu Glu Pro Phe Gly
            180                 185                 190

Val Ile Val Arg Arg Gln Leu Asp Gly Arg Val Leu Leu Asn Thr Thr
        195                 200                 205

Val Ala Pro Leu Phe Phe Ala Asp Gln Phe Leu Gln Leu Ser Thr Ser
    210                 215                 220

Leu Pro Ser Gln Tyr Ile Thr Gly Leu Ala Glu His Leu Ser Pro Leu
225                 230                 235                 240

Met Leu Ser Thr Ser Trp Thr Arg Ile Thr Leu Trp Asn Arg Asp Leu
                245                 250                 255

Ala Pro Thr Pro Gly Ala Asn Leu Tyr Gly Ser His Pro Phe Tyr Leu
            260                 265                 270

Ala Leu Glu Asp Gly Gly Ser Ala His Gly Val Phe Leu Leu Asn Ser
        275                 280                 285

Asn Ala Met Asp Val Val Leu Gln Pro Ser Pro Ala Leu Ser Trp Arg
    290                 295                 300

Ser Thr Gly Gly Ile Leu Asp Val Tyr Ile Phe Leu Gly Pro Glu Pro
305                 310                 315                 320

Lys Ser Val Val Gln Gln Tyr Leu Asp Val Val Gly Tyr Pro Phe Met
                325                 330                 335

```
Pro Pro Tyr Trp Gly Leu Gly Phe His Leu Cys Arg Trp Gly Tyr Ser
            340                 345                 350

Ser Thr Ala Ile Thr Arg Gln Val Val Glu Asn Met Thr Arg Ala His
            355                 360                 365

Phe Pro Leu Asp Val Gln Trp Asn Asp Leu Asp Tyr Met Asp Ser Arg
        370                 375                 380

Arg Asp Phe Thr Phe Asn Lys Asp Gly Phe Arg Asp Phe Pro Ala Met
385                 390                 395                 400

Val Gln Glu Leu His Gln Gly Gly Arg Arg Tyr Met Met Ile Val Asp
                405                 410                 415

Pro Ala Ile Ser Ser Gly Pro Ala Gly Ser Tyr Arg Pro Tyr Asp
            420                 425                 430

Glu Gly Leu Arg Arg Gly Val Phe Ile Thr Asn Glu Thr Gly Gln Pro
            435                 440                 445

Leu Ile Gly Lys Val Trp Pro Gly Ser Thr Ala Phe Pro Asp Phe Thr
        450                 455                 460

Asn Pro Thr Ala Leu Ala Trp Trp Glu Asp Met Val Ala Glu Phe His
465                 470                 475                 480

Asp Gln Val Pro Phe Asp Gly Met Trp Ile Asp Met Asn Glu Pro Ser
                485                 490                 495

Asn Phe Ile Arg Gly Ser Glu Asp Gly Cys Pro Asn Asn Glu Leu Glu
            500                 505                 510

Asn Pro Pro Tyr Val Pro Gly Val Gly Gly Thr Leu Gln Ala Ala
        515                 520                 525

Thr Ile Cys Ala Ser Ser His Gln Phe Leu Ser Thr His Tyr Asn Leu
            530                 535                 540

His Asn Leu Tyr Gly Leu Thr Glu Ala Ile Ala Ser His Arg Ala Leu
545                 550                 555                 560

Val Lys Ala Arg Gly Thr Arg Pro Phe Val Ile Ser Arg Ser Thr Phe
                565                 570                 575

Ala Gly His Gly Arg Tyr Ala Gly His Trp Thr Gly Asp Val Trp Ser
            580                 585                 590

Ser Trp Glu Gln Leu Ala Ser Ser Val Pro Glu Ile Leu Gln Phe Asn
        595                 600                 605

Leu Leu Gly Val Pro Leu Val Gly Ala Asp Val Cys Gly Phe Leu Gly
        610                 615                 620

Asn Thr Ser Glu Glu Leu Cys Val Arg Trp Thr Gln Leu Gly Ala Phe
625                 630                 635                 640

Tyr Pro Phe Met Arg Asn His Asn Ser Leu Leu Ser Leu Pro Gln Glu
                645                 650                 655

Pro Tyr Ser Phe Ser Glu Pro Ala Gln Gln Ala Met Arg Lys Ala Leu
            660                 665                 670

Thr Leu Arg Tyr Ala Leu Leu Pro His Leu Tyr Thr Leu Phe His Gln
        675                 680                 685

Ala His Val Ala Gly Glu Thr Val Ala Arg Pro Leu Phe Leu Glu Phe
            690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
                725                 730                 735

Thr Gly Tyr Phe Pro Leu Gly Thr Trp Tyr Asp Leu Gln Thr Val Pro
            740                 745                 750
```

```
Val Glu Ala Leu Gly Ser Leu Pro Pro Ala Pro Arg Glu
            755                 760             765

Pro Ala Ile His Ser Glu Gly Gln Trp Val Thr Leu Pro Ala Pro Leu
    770             775                 780

Asp Thr Ile Asn Val His Leu Arg Ala Gly Tyr Ile Ile Pro Leu Gln
785             790                 795                 800

Gly Pro Gly Leu Thr Thr Glu Ser Arg Gln Gln Pro Met Ala Leu
                805                 810              815

Ala Val Ala Leu Thr Lys Gly Gly Glu Ala Arg Gly Glu Leu Phe Trp
            820                 825             830

Asp Asp Gly Glu Ser Leu Glu Val Leu Glu Arg Gly Ala Tyr Thr Gln
835             840                 845

Val Ile Phe Leu Ala Arg Asn Asn Thr Ile Val Asn Glu Leu Val Arg
850                 855                 860

Val Thr Ser Glu Gly Ala Gly Leu Gln Leu Gln Lys Val Thr Val Leu
865             870                 875                 880

Gly Val Ala Thr Ala Pro Gln Gln Val Leu Ser Asn Gly Val Pro Val
                885                 890             895

Ser Asn Phe Thr Tyr Ser Pro Asp Thr Lys Val Leu Asp Ile Cys Val
            900                 905                 910

Ser Leu Leu Met Gly Glu Gln Phe Leu Val Ser Trp Cys
            915                 920             925

<210> SEQ ID NO 15
<211> LENGTH: 925
<212> TYPE: PRT
<213> ORGANISM: artificial
<220> FEATURE:
<223> OTHER INFORMATION: variant hGAAwt w/o sp

<400> SEQUENCE: 15

Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
            20                  25                  30

Ala Ser Arg Pro Gly Pro Arg Asp Ala Gln Ala His Pro Gly Arg Pro
        35                  40                  45

Arg Ala Val Pro Thr Gln Cys Asp Val Pro Pro Asn Ser Arg Phe Asp
50                  55                  60

Cys Ala Pro Asp Lys Ala Ile Thr Gln Glu Gln Cys Glu Ala Arg Gly
65                  70                  75                  80

Cys Cys Tyr Ile Pro Ala Lys Gln Gly Leu Gln Gly Ala Gln Met Gly
                85                  90                  95

Gln Pro Trp Cys Phe Phe Pro Ser Tyr Pro Ser Tyr Lys Leu Glu
            100                 105                 110

Asn Leu Ser Ser Ser Glu Met Gly Tyr Thr Ala Thr Leu Thr Arg Thr
        115                 120                 125

Thr Pro Thr Phe Phe Pro Lys Asp Ile Leu Thr Leu Arg Leu Asp Val
    130                 135                 140

Met Met Glu Thr Glu Asn Arg Leu His Phe Thr Ile Lys Asp Pro Ala
145                 150                 155                 160

Asn Arg Arg Tyr Glu Val Pro Leu Glu Thr Pro Arg Val His Ser Arg
                165                 170                 175

Ala Pro Ser Pro Leu Tyr Ser Val Glu Phe Ser Glu Glu Pro Phe Gly
            180                 185                 190
```

```
Val Ile Val His Arg Gln Leu Asp Gly Arg Val Leu Leu Asn Thr Thr
            195                 200                 205
Val Ala Pro Leu Phe Phe Ala Asp Gln Phe Leu Gln Leu Ser Thr Ser
210                 215                 220
Leu Pro Ser Gln Tyr Ile Thr Gly Leu Ala Glu His Leu Ser Pro Leu
225                 230                 235                 240
Met Leu Ser Thr Ser Trp Thr Arg Ile Thr Leu Trp Asn Arg Asp Leu
                245                 250                 255
Ala Pro Thr Pro Gly Ala Asn Leu Tyr Gly Ser His Pro Phe Tyr Leu
                260                 265                 270
Ala Leu Glu Asp Gly Gly Ser Ala His Gly Val Phe Leu Leu Asn Ser
            275                 280                 285
Asn Ala Met Asp Val Val Leu Gln Pro Ser Pro Ala Leu Ser Trp Arg
290                 295                 300
Ser Thr Gly Gly Ile Leu Asp Val Tyr Ile Phe Leu Gly Pro Glu Pro
305                 310                 315                 320
Lys Ser Val Val Gln Gln Tyr Leu Asp Val Val Gly Tyr Pro Phe Met
                325                 330                 335
Pro Pro Tyr Trp Gly Leu Gly Phe His Leu Cys Arg Trp Gly Tyr Ser
                340                 345                 350
Ser Thr Ala Ile Thr Arg Gln Val Val Glu Asn Met Thr Arg Ala His
            355                 360                 365
Phe Pro Leu Asp Val Gln Trp Asn Asp Leu Asp Tyr Met Asp Ser Arg
            370                 375                 380
Arg Asp Phe Thr Phe Asn Lys Asp Gly Phe Arg Asp Phe Pro Ala Met
385                 390                 395                 400
Val Gln Glu Leu His Gln Gly Gly Arg Arg Tyr Met Met Ile Val Asp
                405                 410                 415
Pro Ala Ile Ser Ser Ser Gly Pro Ala Gly Ser Tyr Arg Pro Tyr Asp
                420                 425                 430
Glu Gly Leu Arg Arg Gly Val Phe Ile Thr Asn Glu Thr Gly Gln Pro
            435                 440                 445
Leu Ile Gly Lys Val Trp Pro Gly Ser Thr Ala Phe Pro Asp Phe Thr
450                 455                 460
Asn Pro Thr Ala Leu Ala Trp Trp Glu Asp Met Val Ala Glu Phe His
465                 470                 475                 480
Asp Gln Val Pro Phe Asp Gly Met Trp Ile Asp Met Asn Glu Pro Ser
                485                 490                 495
Asn Phe Ile Arg Gly Ser Glu Asp Gly Cys Pro Asn Asn Glu Leu Glu
                500                 505                 510
Asn Pro Pro Tyr Val Pro Gly Val Val Gly Gly Thr Leu Gln Ala Ala
            515                 520                 525
Thr Ile Cys Ala Ser Ser His Gln Phe Leu Ser Thr His Tyr Asn Leu
530                 535                 540
His Asn Leu Tyr Gly Leu Thr Glu Ala Ile Ala Ser His Arg Ala Leu
545                 550                 555                 560
Val Lys Ala Arg Gly Thr Arg Pro Phe Val Ile Ser Arg Ser Thr Phe
                565                 570                 575
Ala Gly His Gly Arg Tyr Ala Gly His Trp Thr Gly Asp Val Trp Ser
            580                 585                 590
Ser Trp Glu Gln Leu Ala Ser Ser Val Pro Glu Ile Leu Gln Phe Asn
            595                 600                 605
Leu Leu Gly Val Pro Leu Val Gly Ala Asp Val Cys Gly Phe Leu Gly
```

-continued

```
                610                 615                 620
Asn Thr Ser Glu Glu Leu Cys Val Arg Trp Thr Gln Leu Gly Ala Phe
625                 630                 635                 640

Tyr Pro Phe Met Arg Asn His Asn Ser Leu Leu Ser Leu Pro Gln Glu
                645                 650                 655

Pro Tyr Ser Phe Ser Glu Pro Ala Gln Gln Ala Met Arg Lys Ala Leu
                660                 665                 670

Thr Leu Arg Tyr Ala Leu Leu Pro His Leu Tyr Thr Leu Phe His Gln
                675                 680                 685

Ala His Val Ala Gly Glu Thr Val Ala Arg Pro Leu Phe Leu Glu Phe
690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
                725                 730                 735

Thr Gly Tyr Phe Pro Leu Gly Thr Trp Tyr Asp Leu Gln Thr Val Pro
                740                 745                 750

Ile Glu Ala Leu Gly Ser Leu Pro Pro Pro Ala Ala Pro Arg Glu
                755                 760                 765

Pro Ala Ile His Ser Glu Gly Gln Trp Val Thr Leu Pro Ala Pro Leu
770                 775                 780

Asp Thr Ile Asn Val His Leu Arg Ala Gly Tyr Ile Ile Pro Leu Gln
785                 790                 795                 800

Gly Pro Gly Leu Thr Thr Thr Glu Ser Arg Gln Gln Pro Met Ala Leu
                805                 810                 815

Ala Val Ala Leu Thr Lys Gly Gly Glu Ala Arg Gly Glu Leu Phe Trp
                820                 825                 830

Asp Asp Gly Glu Ser Leu Glu Val Leu Glu Arg Gly Ala Tyr Thr Gln
                835                 840                 845

Val Ile Phe Leu Ala Arg Asn Asn Thr Ile Val Asn Glu Leu Val Arg
850                 855                 860

Val Thr Ser Glu Gly Ala Gly Leu Gln Leu Gln Lys Val Thr Val Leu
865                 870                 875                 880

Gly Val Ala Thr Ala Pro Gln Gln Val Leu Ser Asn Gly Val Pro Val
                885                 890                 895

Ser Asn Phe Thr Tyr Ser Pro Asp Thr Lys Val Leu Asp Ile Cys Val
                900                 905                 910

Ser Leu Leu Met Gly Glu Gln Phe Leu Val Ser Trp Cys
                915                 920                 925
```

<210> SEQ ID NO 16
<211> LENGTH: 917
<212> TYPE: PRT
<213> ORGANISM: artificial
<220> FEATURE:
<223> OTHER INFORMATION: hGAA-delta-8

<400> SEQUENCE: 16

```
Leu Leu Val Pro Arg Glu Leu Ser Gly Ser Ser Pro Val Leu Glu Glu
1               5                   10                  15

Thr His Pro Ala His Gln Gln Gly Ala Ser Arg Pro Gly Pro Arg Asp
                20                  25                  30

Ala Gln Ala His Pro Gly Arg Pro Arg Ala Val Pro Thr Gln Cys Asp
                35                  40                  45

Val Pro Pro Asn Ser Arg Phe Asp Cys Ala Pro Asp Lys Ala Ile Thr
```

```
                50                  55                  60
Gln Glu Gln Cys Glu Ala Arg Gly Cys Cys Tyr Ile Pro Ala Lys Gln
 65                  70                  75                  80

Gly Leu Gln Gly Ala Gln Met Gly Gln Pro Trp Cys Phe Phe Pro Pro
                 85                  90                  95

Ser Tyr Pro Ser Tyr Lys Leu Glu Asn Leu Ser Ser Ser Glu Met Gly
                100                 105                 110

Tyr Thr Ala Thr Leu Thr Arg Thr Thr Pro Thr Phe Phe Pro Lys Asp
                115                 120                 125

Ile Leu Thr Leu Arg Leu Asp Val Met Met Glu Thr Glu Asn Arg Leu
130                 135                 140

His Phe Thr Ile Lys Asp Pro Ala Asn Arg Arg Tyr Glu Val Pro Leu
145                 150                 155                 160

Glu Thr Pro His Val His Ser Arg Ala Pro Ser Pro Leu Tyr Ser Val
                165                 170                 175

Glu Phe Ser Glu Glu Pro Phe Gly Val Ile Val Arg Arg Gln Leu Asp
                180                 185                 190

Gly Arg Val Leu Leu Asn Thr Thr Val Ala Pro Leu Phe Phe Ala Asp
                195                 200                 205

Gln Phe Leu Gln Leu Ser Thr Ser Leu Pro Ser Gln Tyr Ile Thr Gly
                210                 215                 220

Leu Ala Glu His Leu Ser Pro Leu Met Leu Ser Thr Ser Trp Thr Arg
225                 230                 235                 240

Ile Thr Leu Trp Asn Arg Asp Leu Ala Pro Thr Pro Gly Ala Asn Leu
                245                 250                 255

Tyr Gly Ser His Pro Phe Tyr Leu Ala Leu Glu Asp Gly Gly Ser Ala
                260                 265                 270

His Gly Val Phe Leu Leu Asn Ser Asn Ala Met Asp Val Val Leu Gln
                275                 280                 285

Pro Ser Pro Ala Leu Ser Trp Arg Ser Thr Gly Gly Ile Leu Asp Val
                290                 295                 300

Tyr Ile Phe Leu Gly Pro Glu Pro Lys Ser Val Val Gln Gln Tyr Leu
305                 310                 315                 320

Asp Val Val Gly Tyr Pro Phe Met Pro Pro Tyr Trp Gly Leu Gly Phe
                325                 330                 335

His Leu Cys Arg Trp Gly Tyr Ser Ser Thr Ala Ile Thr Arg Gln Val
                340                 345                 350

Val Glu Asn Met Thr Arg Ala His Phe Pro Leu Asp Val Gln Trp Asn
                355                 360                 365

Asp Leu Asp Tyr Met Asp Ser Arg Arg Asp Phe Thr Phe Asn Lys Asp
                370                 375                 380

Gly Phe Arg Asp Phe Pro Ala Met Val Gln Glu Leu His Gln Gly Gly
385                 390                 395                 400

Arg Arg Tyr Met Met Ile Val Asp Pro Ala Ile Ser Ser Ser Gly Pro
                405                 410                 415

Ala Gly Ser Tyr Arg Pro Tyr Asp Glu Gly Leu Arg Arg Gly Val Phe
                420                 425                 430

Ile Thr Asn Glu Thr Gly Gln Pro Leu Ile Gly Lys Val Trp Pro Gly
                435                 440                 445

Ser Thr Ala Phe Pro Asp Phe Thr Asn Pro Thr Ala Leu Ala Trp Trp
                450                 455                 460

Glu Asp Met Val Ala Glu Phe His Asp Gln Val Pro Phe Asp Gly Met
465                 470                 475                 480
```

```
Trp Ile Asp Met Asn Glu Pro Ser Asn Phe Ile Arg Gly Ser Glu Asp
            485                 490                 495
Gly Cys Pro Asn Asn Glu Leu Glu Asn Pro Pro Tyr Val Pro Gly Val
                500                 505                 510
Val Gly Gly Thr Leu Gln Ala Ala Thr Ile Cys Ala Ser Ser His Gln
        515                 520                 525
Phe Leu Ser Thr His Tyr Asn Leu His Asn Leu Tyr Gly Leu Thr Glu
    530                 535                 540
Ala Ile Ala Ser His Arg Ala Leu Val Lys Ala Arg Gly Thr Arg Pro
545                 550                 555                 560
Phe Val Ile Ser Arg Ser Thr Phe Ala Gly His Gly Arg Tyr Ala Gly
                565                 570                 575
His Trp Thr Gly Asp Val Trp Ser Ser Trp Glu Gln Leu Ala Ser Ser
                580                 585                 590
Val Pro Glu Ile Leu Gln Phe Asn Leu Leu Gly Val Pro Leu Val Gly
            595                 600                 605
Ala Asp Val Cys Gly Phe Leu Gly Asn Thr Ser Glu Glu Leu Cys Val
        610                 615                 620
Arg Trp Thr Gln Leu Gly Ala Phe Tyr Pro Phe Met Arg Asn His Asn
625                 630                 635                 640
Ser Leu Leu Ser Leu Pro Gln Glu Pro Tyr Ser Phe Ser Glu Pro Ala
                645                 650                 655
Gln Gln Ala Met Arg Lys Ala Leu Thr Leu Arg Tyr Ala Leu Leu Pro
                660                 665                 670
His Leu Tyr Thr Leu Phe His Gln Ala His Val Ala Gly Glu Thr Val
            675                 680                 685
Ala Arg Pro Leu Phe Leu Glu Phe Pro Lys Asp Ser Ser Thr Trp Thr
        690                 695                 700
Val Asp His Gln Leu Leu Trp Gly Glu Ala Leu Leu Ile Thr Pro Val
705                 710                 715                 720
Leu Gln Ala Gly Lys Ala Glu Val Thr Gly Tyr Phe Pro Leu Gly Thr
                725                 730                 735
Trp Tyr Asp Leu Gln Thr Val Pro Val Glu Ala Leu Gly Ser Leu Pro
            740                 745                 750
Pro Pro Pro Ala Ala Pro Arg Glu Pro Ala Ile His Ser Glu Gly Gln
        755                 760                 765
Trp Val Thr Leu Pro Ala Pro Leu Asp Thr Ile Asn Val His Leu Arg
770                 775                 780
Ala Gly Tyr Ile Ile Pro Leu Gln Gly Pro Gly Leu Thr Thr Thr Glu
785                 790                 795                 800
Ser Arg Gln Gln Pro Met Ala Leu Ala Val Ala Leu Thr Lys Gly Gly
                805                 810                 815
Glu Ala Arg Gly Glu Leu Phe Trp Asp Asp Gly Glu Ser Leu Glu Val
                820                 825                 830
Leu Glu Arg Gly Ala Tyr Thr Gln Val Ile Phe Leu Ala Arg Asn Asn
            835                 840                 845
Thr Ile Val Asn Glu Leu Val Arg Val Thr Ser Glu Gly Ala Gly Leu
        850                 855                 860
Gln Leu Gln Lys Val Thr Val Leu Gly Val Ala Thr Ala Pro Gln Gln
865                 870                 875                 880
Val Leu Ser Asn Gly Val Pro Val Ser Asn Phe Thr Tyr Ser Pro Asp
                885                 890                 895
```

```
Thr Lys Val Leu Asp Ile Cys Val Ser Leu Leu Met Gly Glu Gln Phe
                900                 905                 910

Leu Val Ser Trp Cys
        915

<210> SEQ ID NO 17
<211> LENGTH: 27
<212> TYPE: PRT
<213> ORGANISM: artificial
<220> FEATURE:
<223> OTHER INFORMATION: sp1

<400> SEQUENCE: 17

Met Gly Val Arg His Pro Pro Cys Ser His Arg Leu Leu Ala Val Cys
1               5                  10                  15

Ala Leu Val Ser Leu Ala Thr Ala Ala Leu Leu
            20                  25

<210> SEQ ID NO 18
<211> LENGTH: 18
<212> TYPE: PRT
<213> ORGANISM: artificial
<220> FEATURE:
<223> OTHER INFORMATION: sp7

<400> SEQUENCE: 18

Met Ala Phe Leu Trp Leu Leu Ser Cys Trp Ala Leu Leu Gly Thr Thr
1               5                  10                  15

Phe Gly

<210> SEQ ID NO 19
<211> LENGTH: 24
<212> TYPE: PRT
<213> ORGANISM: artificial
<220> FEATURE:
<223> OTHER INFORMATION: sp2

<400> SEQUENCE: 19

Met Pro Ser Ser Val Ser Trp Gly Ile Leu Leu Leu Ala Gly Leu Cys
1               5                  10                  15

Cys Leu Val Pro Val Ser Leu Ala
            20

<210> SEQ ID NO 20
<211> LENGTH: 25
<212> TYPE: PRT
<213> ORGANISM: artificial
<220> FEATURE:
<223> OTHER INFORMATION: sp6

<400> SEQUENCE: 20

Met Pro Pro Pro Arg Thr Gly Arg Gly Leu Leu Trp Leu Gly Leu Val
1               5                  10                  15

Leu Ser Ser Val Cys Val Ala Leu Gly
            20                  25

<210> SEQ ID NO 21
<211> LENGTH: 22
<212> TYPE: PRT
<213> ORGANISM: artificial
<220> FEATURE:
<223> OTHER INFORMATION: sp8

<400> SEQUENCE: 21
```

```
Met Ala Ser Arg Leu Thr Leu Leu Thr Leu Leu Leu Leu Leu Ala
1               5                   10                  15

Gly Asp Arg Ala Ser Ser
            20

<210> SEQ ID NO 22
<211> LENGTH: 20
<212> TYPE: DNA
<213> ORGANISM: artificial
<220> FEATURE:
<223> OTHER INFORMATION: primer

<400> SEQUENCE: 22
ggctgtattc ccctccatcg                                              20

<210> SEQ ID NO 23
<211> LENGTH: 22
<212> TYPE: DNA
<213> ORGANISM: artificial
<220> FEATURE:
<223> OTHER INFORMATION: primer

<400> SEQUENCE: 23
ccagttggta acaatgccat gt                                           22

<210> SEQ ID NO 24
<211> LENGTH: 22
<212> TYPE: DNA
<213> ORGANISM: artificial
<220> FEATURE:
<223> OTHER INFORMATION: primer

<400> SEQUENCE: 24
ggtctttctg gtgcttgtct ca                                           22

<210> SEQ ID NO 25
<211> LENGTH: 19
<212> TYPE: DNA
<213> ORGANISM: artificial
<220> FEATURE:
<223> OTHER INFORMATION: primer

<400> SEQUENCE: 25
gttcggcttc ccattctcc                                               19
```

HYBRID REGULATORY ELEMENTS

CROSS-REFERENCE TO RELATED APPLICATIONS

This application is the U.S. national stage application of International Patent Application No. PCT/EP2019/053061, filed Feb. 7, 2019, which claims the benefit of U.S. Provisional Application Ser. No. 62/627,442, filed Feb. 7, 2018.

The Sequence Listing for this application is labeled "Seq-List.txt" which was created on Jun. 15, 2020 and is 35 KB. The entire content of the sequence listing is incorporated herein by reference in its entirety.

FIELD OF THE INVENTION

The present invention relates to hybrid transcription regulatory elements to drive gene expression, in particular hybrid promoters, designed by the fusion of at least two transcription regulatory elements with different tissue selectivities, such as two promoters driving expression in different tissues in a tissue-selective manner.

BACKGROUND OF THE INVENTION

Gene therapy has the potential to provide sustained therapeutic correction of genetic diseases and is currently tested in a number of clinical trials. Yet, insufficient transgene expression in the desired target tissues and anti-transgene immunity still represent important hurdles to achieve successful gene therapy for many diseases. This is particularly relevant for the treatment of diseases that are caused by mutations in genes which are expressed ubiquitously or in multiple tissues of the body [such as liver, muscle and the central nervous system (CNS)]. Example of these disease include: i. lysosomal storage diseases [(LSDs), such as Pompe disease (PD), mucopolysaccharidosis type I to VII (MPSI-VII), Sandhoff and Tay-Sachs disease] ii. metabolic diseases [such as Maple syrup disease (MSUD), Methylmalonic academia (MMA), glycogenosis type I and III (GSDI, III], Niemann-Pick disease (NPC), Canavan disease, Phenylketonuria (PKU)]; and iii. neuro-muscular diseases [such as Spinal Muscular Atrophy (SMA) and Freidreich's ataxia (FA)]. So far, the use of ubiquitous promoters driving expression in different tissues represents the only option to target transgene expression to multiple affected tissues including visceral organs, muscle and CNS. The ubiquitous promoters are far from being ideal tools for in vivo AAV gene therapy as they have been reported to promote liver genotoxicity in animal models due their strong transactivation activity which can lead to tumor formation (Chandler et al., JCI 2015; 125(2):870-880) and is associated with ectopic non-physiological gene expression. Recently, severe toxicity has been reported in pre-clinical studies in non-human primates and piglets treated by systemic delivery of high doses of AAV vectors containing the ubiquitous chicken beta actin promoter (Hinderer et al., Hum Gene Ther. 2018 Feb. 12).

In addition, many diseases are caused by genetic mutations that result in large alterations or complete absence of a protein product (null mutation). Treatment of these diseases by gene therapy leads to the de novo expression of a wild-type protein that has high risk to trigger a detrimental immune response that may prevent therapeutic efficacy and even mediate the destruction of transgene-expressing cells. This is particularly critical for therapeutic protein products which are highly immunogenic such as: coagulation factor VIII [FVIII, causing hemophilia A (HA)], lysosomal enzymes α-L-iduronidase [IDUA (alphase-Liduronidase), causing MPSI and acid-α-glucosidase (GAA), causing Pompe disease] and muscle proteins [dystrophin, causing Duchenne muscular dystrophy (DMD) and α-sarcoglycan (SGCA) causing Limb-girdle-muscular dystrophy 2D (LGMD2D)], among others.

Pompe disease is a severe neuromuscular disorder caused by mutations in the lysosomal enzyme acid alpha-glucosidase (GAA), which result in the pathological accumulation of glycogen in all tissues. Pompe disease is classified in two forms: Infantile-Onset Pompe disease (IOPD) with a morbidity that occurs during the first year of birth and Late Onset Pompe disease (LOPD) which appear later in childhood, adolescence or adulthood [Kishnani et al., Am J Med Genet C Semin Med Genet. 2012]. Therapeutic intervention in the first months of life is an important medical need for IOPD. If untreated, IOPD leads to death in the first year of life while late/inefficient treatment would be not able to revert advanced disease signs [Chien et. al., Pediatr Neonatol. 2013 August; 54(4):219-27]. Enzyme replacement therapy (ERT) with recombinant human GAA (rhGAA) is available for PD. Despite being a life-saving treatment for IOPD subjects, ERT has however limited efficacy in CNS and muscle groups refractory to rhGAA uptake. Moreover, ERT is hampered by the induction of immune responses against the therapeutic product (rhGAA) that prevent therapeutic efficacy. Similar to ERT, AAV gene therapy in clinical trials of Pompe disease (Corti et al., Hum Gene Ther Clin Dev. 2017 December; 28(4):208-218) and pre-clinical studies in mouse models of the diseases faced the same limitations. In particular: 1. strong immune responses towards GAA are observed following gene transfer to muscle using either ubiquitous or muscle-selective promoters; 2. limited bio-distribution of the GAA protein to the affected tissues, such as whole-body muscle and the nervous system is achieved. The GAA protein is indeed naturally poorly secreted by the cells and cannot cross the blood-brain-barrier (circulating GAA protein size~110 Kda).

Accordingly, there remains a need for the provision of sustained and widespread expression of therapeutic transgenes in multiple tissues of the body. In addition, there remains a need for providing sustained and widespread expression of transgenes in different target tissues, in combination with the induction of immune tolerance to the therapeutic protein for safe and effective gene therapy.

SUMMARY OF THE INVENTION

The present invention provides genetic engineering strategies implementing novel multi-tissue-selective transcription regulatory elements designed by the inventors for expressing a transgene of interest in a subject in need thereof.

In particular, the present invention relates to a nucleic acid sequence combining, fused together, at least two different transcription regulatory elements having different tissue-selective expression profiles. This nucleic acid sequence may provide expression of the transgene of interest in a minimum of two tissues or in multiple tissues, depending on the specific need, such as depending on the specific disease need. One of the tissues targeted may be a tolerogenic tissue (such as the liver) when it is necessary to achieve immunological tolerance by the immune system. This multi-tissue-selective genetic engineering strategy leads to an increase of gene expression efficacy, as compared to classical strategies focusing on the expression of the transgene in one tissue only. The invention is thus particularly advantageous in the context of gene therapy. The combination of multiple tissue-selective transcription regulatory elements (such as multiple tissue-selective promoters) in the present invention has the advantage of driving high transgene expression in desired tissues in a selective way.

In addition, differently from ubiquitous promoters, the present invention prevents ectopic transgene expression in tissues that do not express physiologically the transgene of interest or where the expression of the transgene of interest is not desired. The combination of transcription regulatory elements disclosed herein also overcomes the concerns over genotoxicity elicited by ubiquitous promoters (Chandler et al., cited supra) and may also prevent possible toxicities recently reported in pre-clinical studies in non-human Primates (Hinderer et al., cited supra).

A first aspect of the invention relates to a nucleic acid sequence comprising:
  (i) a first transcription regulatory element capable of driving or enhancing tissue-selective expression in a first tissue; and
  (ii) a second transcription regulatory element capable of driving or enhancing tissue-selective expression in a second tissue;
  wherein the first and second transcription regulatory elements are fused together; and
  wherein at least one of the first and second transcription regulatory elements is a tissue-selective promoter.

In a particular embodiment, the first transcription regulatory element is a tissue-selective promoter capable of driving tissue-selective expression in a first tissue. In a further embodiment, the second transcription regulatory element is also a tissue-selective promoter.

In particular embodiment, one transcription regulatory element is selected in the group consisting of a liver-selective promoter, a muscle-selective promoter and a neuron-selective promoter, in particular a liver-selective promoter. In a particular embodiment, when the transcription regulatory element is a liver-selective promoter, it is preferably selected in the group consisting of the alpha-1 antitrypsin promoter (hAAT), a combination of the ApoE enhancer and the hAAT promoter, the transthyretin promoter, the albumin promoter, the thyroxine-binding globulin (TBG) promoter and the LSP promoter. In another embodiment, when the transcription regulatory element is a muscle-selective promoter, it is preferably selected in the group consisting of a spC5.12 promoter, the MHCK7 promoter, the E-syn promoter, a muscle creatine kinase myosin light chain (MLC) promoter, a myosin heavy chain (MHC) promoter, a desmin promoter, a cardiac troponin C promoter, a troponin I promoter, a myoD gene family promoter, an alpha actin promoter, an beta actin promoter, an gamma actin promoter, a muscle-selective promoter residing within intron 1 of the ocular form of Pitx3 and a CK6 promoter. In another embodiment, when the transcription regulatory element is a muscle-selective promoter, it is preferably selected in the group consisting of a spC5.12 promoter, the MHCK7 promoter, the E-syn promoter, a muscle creatine kinase myosin light chain (MLC) promoter, a myosin heavy chain (MHC) promoter, a cardiac troponin C promoter, a troponin I promoter, a myoD gene family promoter, an alpha actin promoter, an beta actin promoter, an gamma actin promoter, a muscle-selective promoter residing within intron 1 of the ocular form of Pitx3 and a CK6 promoter. In yet another particular embodiment, when the transcription regulatory element is a neuron-selective promoter, it is preferably selected in the group consisting of synapsin-1 (Syn) promoter, neuron-specific enolase (NSE) promoter, neurofilament light-chain gene promoter, neuron-specific vgf gene promoter, synapsin-2 promoter, tyrosine hydroxylase promoter, dopamine β-hydroxylase promoter, hypoxanthine phosphoribosyltransferase promoter, low affinity NGF receptor promoter, choline acetyl transferase promoter, Calcitonin Gene-Related Peptide (CGRP) promoter, Hb9 promoter, GFAP promoter, Calbindin 2 promoter, Mnx1 promoter, Nestin promoter, Parvalbumin promoter, Somatostatin promoter and Plp1 promoter.

Furthermore, in another embodiment, the muscle-selective promoter is selected from the group consisting of spC5.12, desmin and Muscle Creatine Kinase (MCK) promoters, in particular from the group consisting of spC5.12 and Muscle Creatine Kinase (MCK) promoters; and/or the neuron-selective promoter is the Syn promoter.

In yet another embodiment, the nucleic acid sequence is:
  (i) a combination of the ApoE enhancer and the hAAT promoter and (ii) is the spC5.12 promoter; or
  (i) a combination of the ApoE enhancer and the hAAT promoter and (ii) is the Syn promoter; or
  (i) the ApoE enhancer and (ii) is the spC5.12 promoter.

According to another aspect, the invention relates to an expression cassette comprising the nucleic acid sequence disclosed herein, and a transgene of interest. The transgene of interest may more particularly be a therapeutic transgene of interest. In specific embodiments, the therapeutic transgene of interest is acid alpha-glucosidase (GAA).

In another aspect, the invention relates to a vector comprising the expression cassette disclosed herein. Said vector may be, in particular a viral vector. Representative viral vectors include, without limitation, adenovirus vectors, retrovirus vectors, lentivirus vectors and AAV vectors. In a particular embodiment, the viral vector is an AAV vector, such as an AAV vector comprising an AAV8 or AAV9 capsid.

The invention further relates to an isolated cell transformed with the nucleic acid sequence, the expression cassette or the vector disclosed herein.

In addition, the invention also relates to a pharmaceutical composition comprising the expression cassette, the vector, or the cell according to the invention. In this aspect, the transgene of interest comprised in the expression cassette, the vector or the cell is a therapeutic transgene.

Furthermore, the invention also relates to the expression cassette, the vector or the cell disclosed herein, for use as a medicament. In this aspect, the transgene of interest comprised in the expression cassette, the vector or the cell is a therapeutic transgene.

In another aspect, the invention relates to the expression cassette, the vector or the cell disclosed herein, for use in a method for the treatment of a disorder by gene therapy by expression of a therapeutic transgene into a tissue of therapeutic interest. The invention may be used to treat a number of disorders. In a particular embodiment, the disorder is selected in the group consisting of:
  a lysosomal storage disease (LSD), such as mucopolysaccharidosis type I to VII (MPSI-VII), Sandhoff disease and Tay-Sachs;
  a metabolic disease such as Maple syrup disease (MSUD), Methylmalonic academia (MMA), glycogenosis type I and III (GSDI and III], Niemann-Pick disease (NPC), Canavan disease, Phenylketonuria (PKU);
  a neuromuscular disorder such as muscular dystrophies (e.g. myotonic dystrophy (Steinert disease), Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy, motor neuron diseases (e.g. amyotrophic lateral sclerosis (ALS), spinal muscular atrophy (Infantile progressive spinal muscular atrophy (type 1, Werdnig-Hoffmann disease), intermediate spinal muscular atrophy (Type 2), juvenile spinal muscular atrophy (Type 3, Kugelberg-Welander disease), adult spinal muscular atrophy (Type 4)), spinal-bulbar muscular atrophy (Kennedy disease)), inflammatory Myopathies (e.g. polymyositis dermatomyositis, inclusion-body myositis), diseases of neuromuscular junction (e.g. myasthenia gravis, Lambert-Eaton (myasthenic) syndrome, congenital myasthenic syndromes), diseases of peripheral nerve (e.g. Charcot-Marie-Tooth disease, Friedreich's ataxia, Dejerine-Sottas disease), metabolic diseases of muscle (e.g. phosphorylase deficiency (McArdle disease) acid maltase deficiency (Pompe disease) phosphofructokinase deficiency (Tarui disease) debrancher enzyme deficiency (Cori or Forbes disease) mitochondrial myopathy, carnitine deficiency, carnitine palmityl transferase deficiency, phosphogly cerate kinase deficiency, phosphoglycerate mutase deficiency, lactate dehydrogenase deficiency, myoadenylate deaminase deficiency), myopathies due to endocrine abnormalities (e.g. hyperthyroid myopathy, hypothyroid myopathy), and other myopathies (e.g. myotonia congenita paramyotonia congenita central core disease nemaline myopathy myotubular myopathy periodic paralysis); and Other diseases such as hemophilia A, MPSI, Alzheimer's Disease, Parkinson's Disease, Huntington's Disease, Tourette Syndrome, schizophrenia, Sly disease, Hunter's disease, dementia, paranoia, obsessive compulsive disorder, learning disabilities, ALS, Charcot-Marie Tooth disease, Kennedy's disease, glioblastoma, neuroblastoma, autism, Gaucher's disease, Hurler's disease, Krabbe's disease, and altered behaviors (e. g., disorders in sleeping, perception or cognition).

More specifically, the disorder may be selected in the group consisting of
- a lysosomal storage disease (LSD), such as mucopolysaccharidosis type I to VII (MPSI-VII), Sandhoff disease and Tay-Sachs;
- a metabolic disease such as Maple syrup disease (MSUD), Methylmalonic academia (MMA), glycogenosis type I and III (GSDI and III], Niemann-Pick disease (NPC), Canavan disease, Phenylketonuria (PKU);
- a neuromuscular disorder such as muscular dystrophies (e.g. myotonic dystrophy (Steinert disease), Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy, motor neuron diseases (e.g. amyotrophic lateral sclerosis (ALS), spinal muscular atrophy (Infantile progressive spinal muscular atrophy (type 1, Werdnig-Hoffmann disease), intermediate spinal muscular atrophy (Type 2), juvenile spinal muscular atrophy (Type 3, Kugelberg-Welander disease), adult spinal muscular atrophy (Type 4)), spinal-bulbar muscular atrophy (Kennedy disease)), inflammatory Myopathies (e.g. polymyositis dermatomyositis, inclusion-body myositis), diseases of neuromuscular junction (e.g. myasthenia gravis, Lambert-Eaton (myasthenic) syndrome, congenital myasthenic syndromes), diseases of peripheral nerve (e.g. Charcot-Marie-Tooth disease, Friedreich's ataxia, Dejerine-Sottas disease).

In a further particular embodiment, the disorder is a glycogen storage disease, in particular Pompe disease, more particularly infantile onset Pompe disease or late onset Pompe disease, even more particularly infantile onset Pompe disease.

LEGEND OF THE FIGURES

FIG. 1. Schematic representation of the expression cassettes used.

A: Ubiquitous promoter (CAG) composed of a cytomegalovirus (CMV) enhancer and a chicken β-actin promoter (CBA) promoter and basic single-tissue promoters. B (invention): hybrid multi-tissue-selective promoters. ITR: inverted terminal repeats for AAV packaging; ApoE: Apolipoprotein enhancer; hAAT: human alpha-1 anti-trypsin promoter; spC5.12: synthetic promoter C5.12; hSYN: human Synapsin promoter; intron: either HBB2 2.1 (improved synthetic human beta-globin-derived (HBB2 2.1) or SV40 intron; hGAA: human acid alpha-glucosidase coding sequence followed by human bovine growth hormone polyadenylation signal.

Figure 2A:
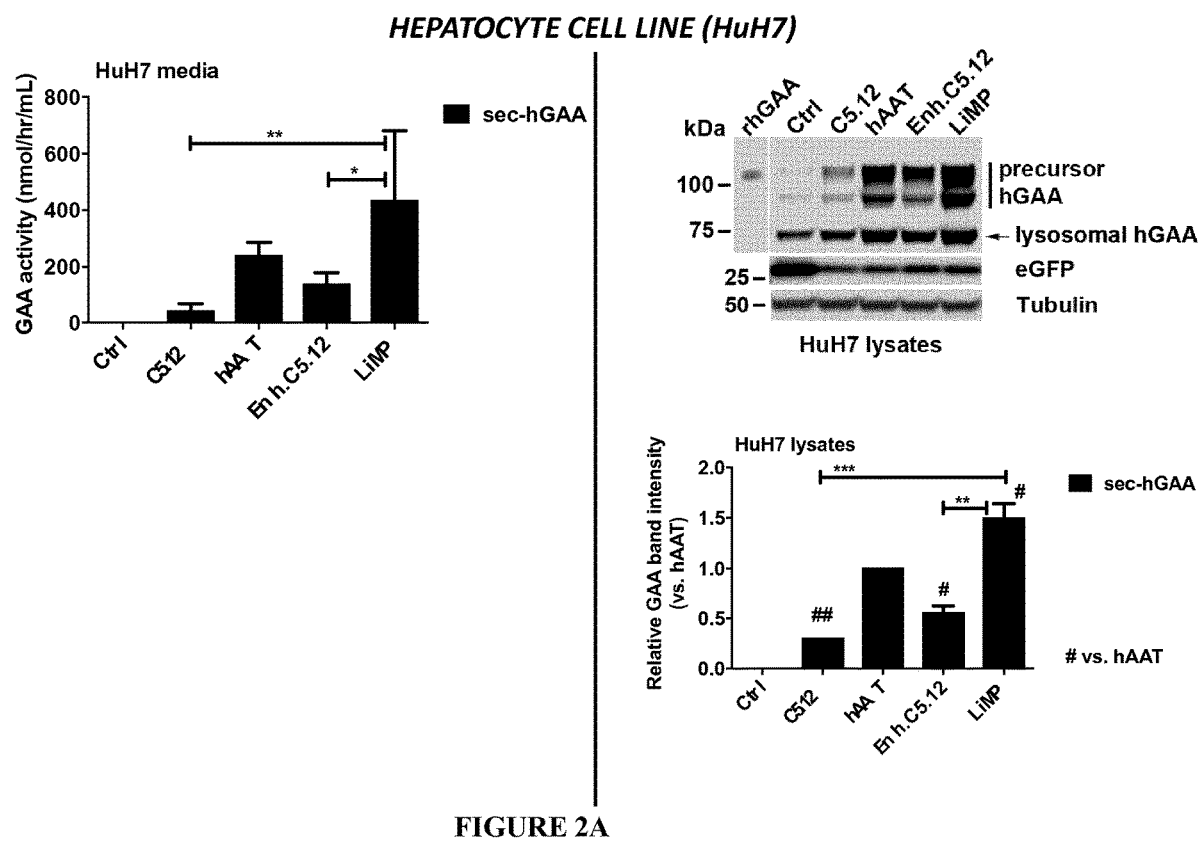
Figure 2B:
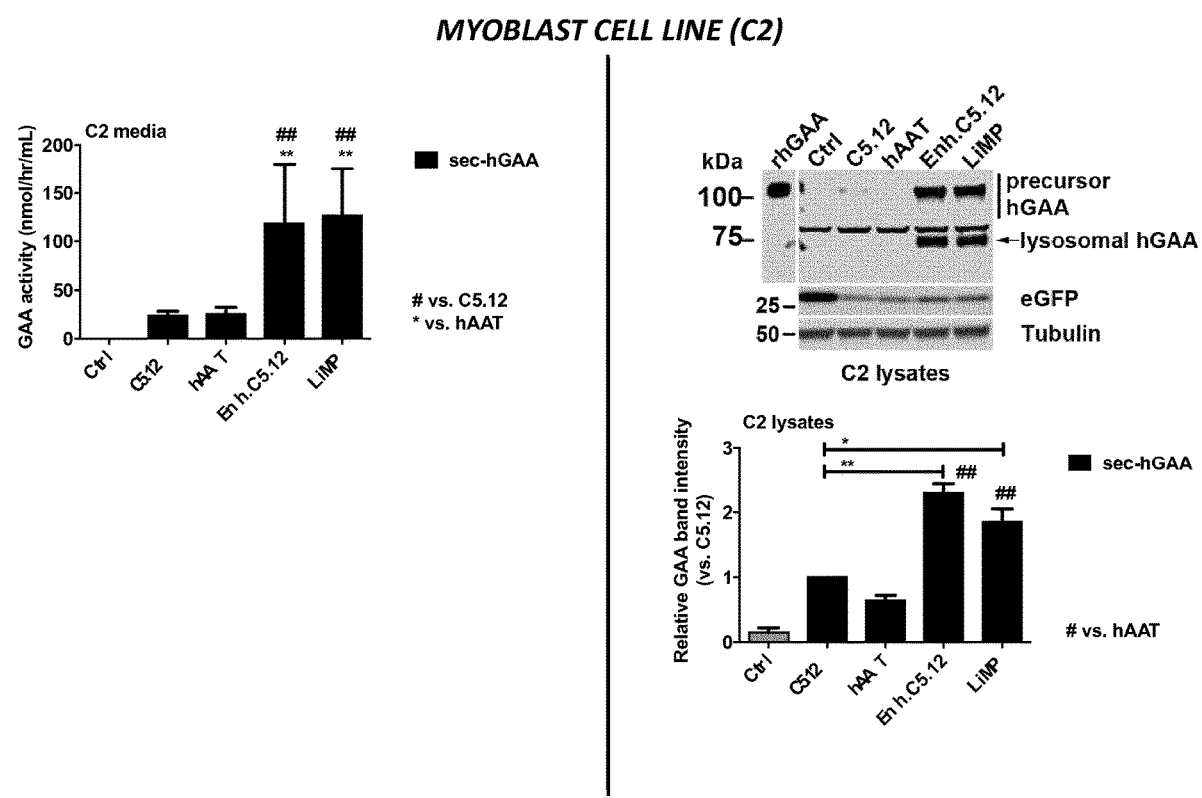

FIGS. 2A-2B. Activity of hybrid liver-muscle promoters Enh.C5.12 and LiMP in cell lines.

Analysis of GAA expression 72 hours upon transient transfection of human hepatocyte cell line HuH7 (FIG. 2A) and myoblast cell line C2 (FIG. 2B) with plasmids encoding for a highly secretable hGAA transgene (sp7-Δ8-co, abbreviated as sec-hGAA, Table 1) under the control of muscle-selective (C5.12), hepatocyte-selective (hAAT) or our newly generated hybrid liver-muscle promoters (Enh.C5.12 and LiMP). A plasmid encoding for enhanced green fluorescent protein (Ctrl) was used as negative control and co-transfected with GAA-expressing plasmids as positive control for transfection. Fig. A-B. Left panels: GAA activity in cell media at 72H (n=4 independent experiments); right panels: GAA protein expression in cell lysates assessed by Western blot analysis with anti-GAA antibody (n=2 independent experiments). Anti-eGFP and anti-Tubulin antibodies were used as transfection control and loading control, respectively. GAA band quantification is depicted. Statistical analysis was performed by One-way ANOVA with Tukey post hoc. *$p<0.05$, $p<0.01$, *$p<0.001$, ****$p<0.0001$, #$p<0.05$, ##$p<0.01$.

Figure 3A:
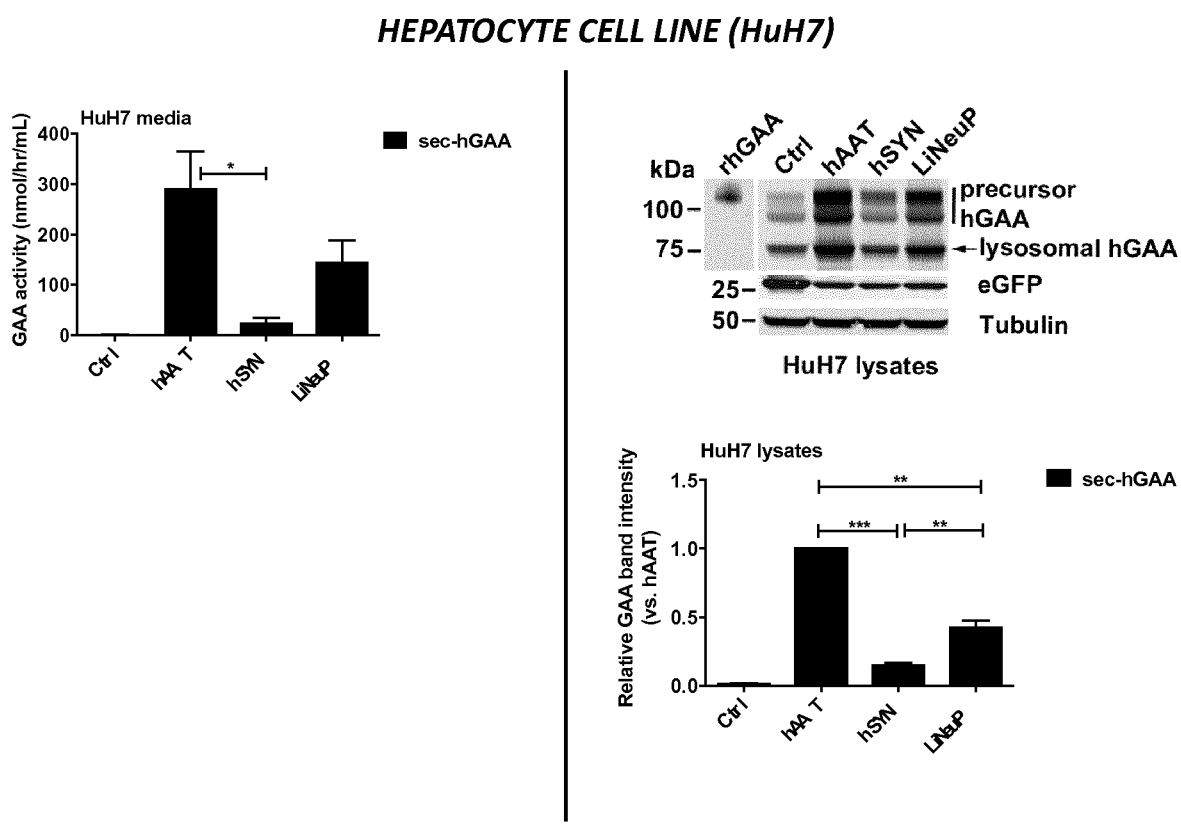
Figure 3B:
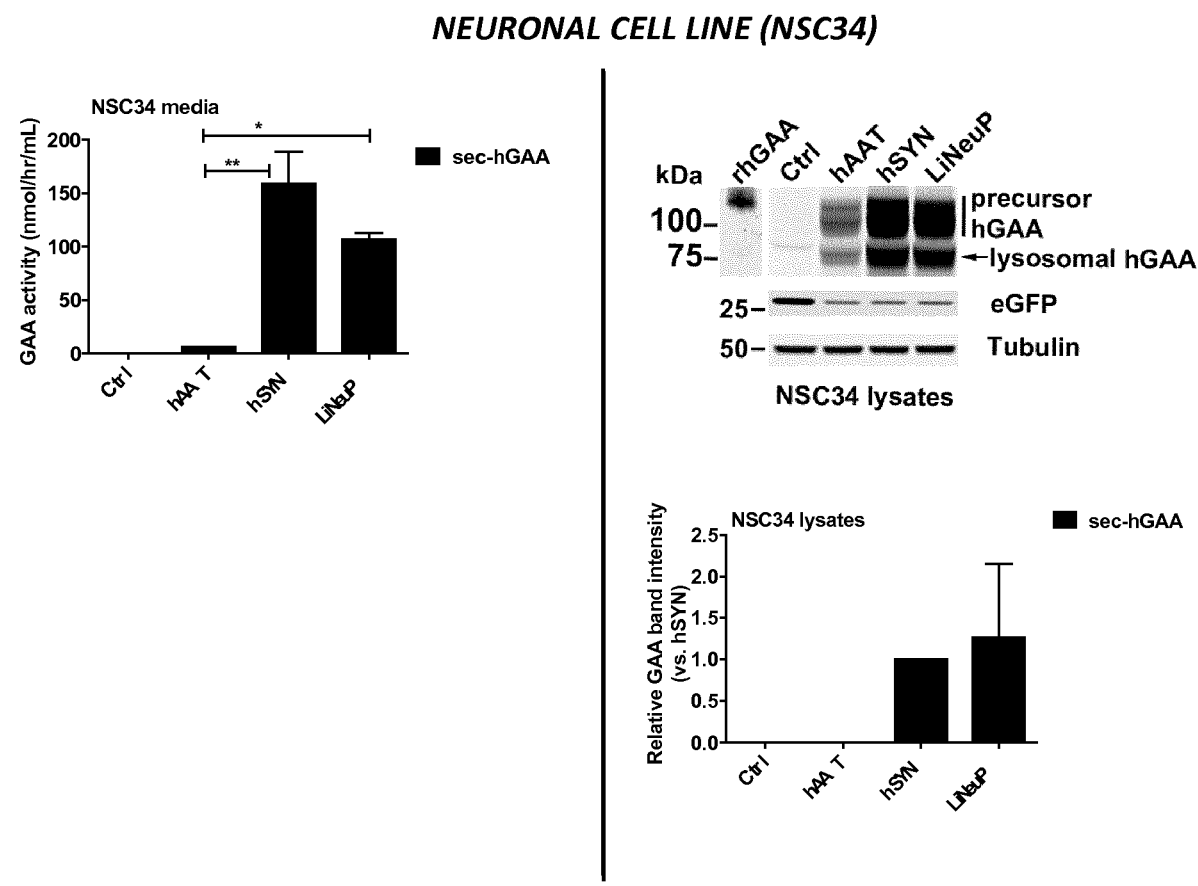

FIGS. 3A-3B. Activity of hybrid liver-neuron promoter LiNeuP in cell lines.

Analysis of GAA expression 72 hours upon transient transfection of human hepatocyte cell line HuH7 (FIG. 3A) or neuronal cell line NSC34 (FIG. 3B) with plasmids encoding for a highly secretable hGAA transgene (sp7-Δ8-co, abbreviated as sec-hGAA, Table 1) under the control of the neuron-selective human Synapsin promoter (hSYN), hepatocyte-selective (hAAT) or our newly generated hybrid liver-neuron promoter (LiNeuP). A plasmid encoding for enhanced green fluorescent protein (Ctrl) was used as negative control and co-transfected with GAA-expressing plasmids as positive control for transfection. FIGS. 3A-B. Left panels: GAA activity in cell media at 72H (n=2 independent experiments); right panels: GAA protein expression in cell lysates assessed by Western blot analysis with anti-GAA antibody (n=2 independent experiments). Anti-eGFP and anti-Tubulin antibodies were used as transfection control and loading control, respectively. GAA band quantification is depicted. Statistical analysis was performed by One-way ANOVA with Tukey posthoc. $*p<0.05$, $p<0.01$, $*p<0.001$, $****p<0.0001$.

Figure 4A:
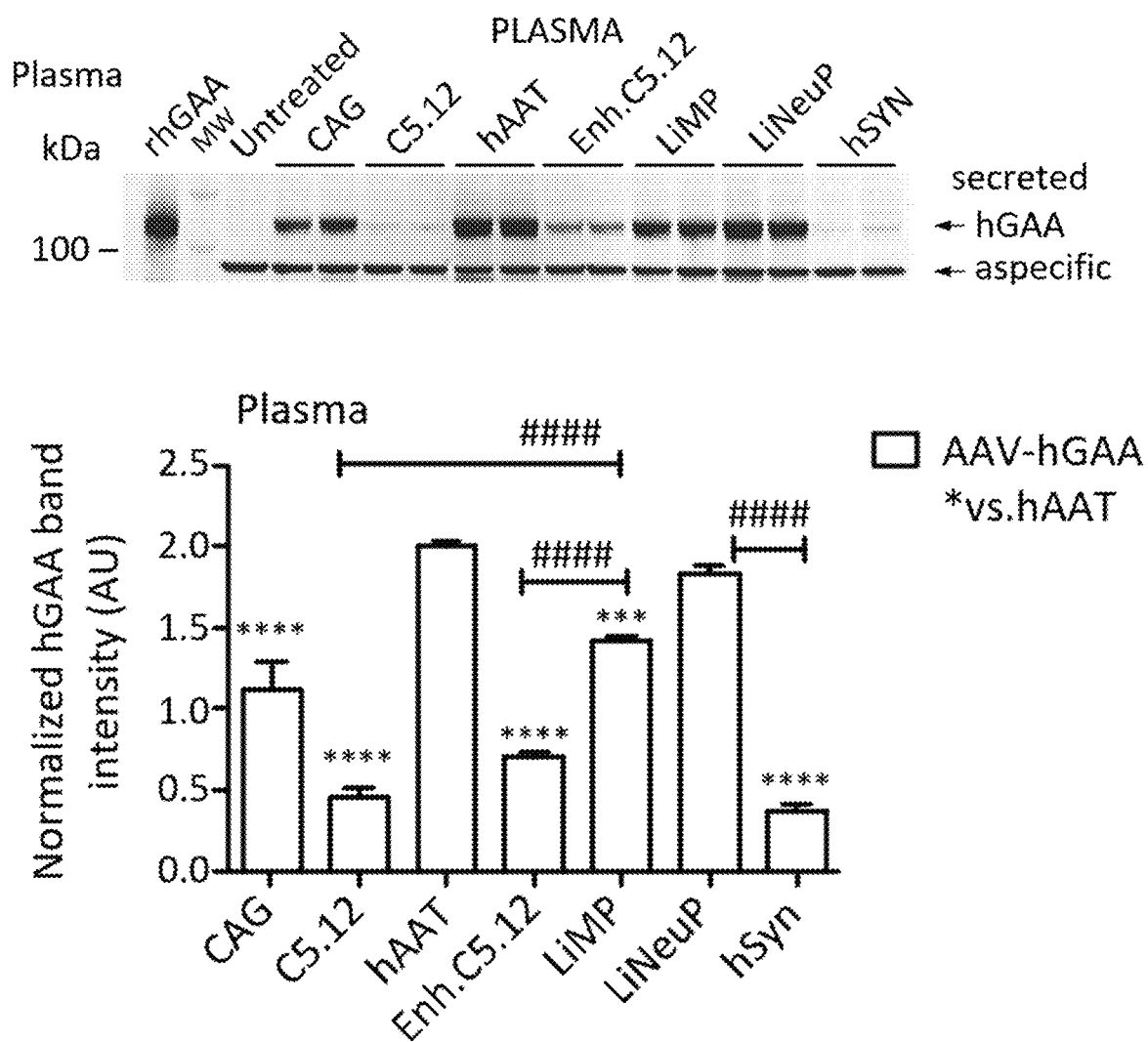

FIG. 4A. Circulating GAA protein in wild type C57BL/6 mice.

Analysis of GAA expression 4 weeks following intravenous injection of an AAV9 vector harboring a full-length codon optimized GAA transgene (abbreviated as hGAA) under the control of ubiquitous (CAG), liver-selective (hAAT) and muscle-selective (C5.12) promoters or our newly generated liver-muscle (Enh.C5.12, LiMP) and liver-neurons (LiNeuP) promoters (AAV dose: $2\times10^{12}$ vg/kg; mouse n=4/group). Top panel: Representative Western blot of mouse plasma with anti-GAA antibody; Bottom panel: Quantification of GAA bands. The GAA band intensity was normalized by the intensity of the non-specific band detected in plasma and used as loading control. rhGAA which is the recombinant human GAA protein (commercial name Myozyme) used as positive control; molecular weight marker (kDa on the left); Untreated: plasma from not injected C57BL/6 mouse used as negative control. Statistical analysis was performed by One-way ANOVA with Tukey post hoc. $*p<0.05$, $p<0.01$, $*p<0.001$, $****p<0.0001$.

Figure 4B:
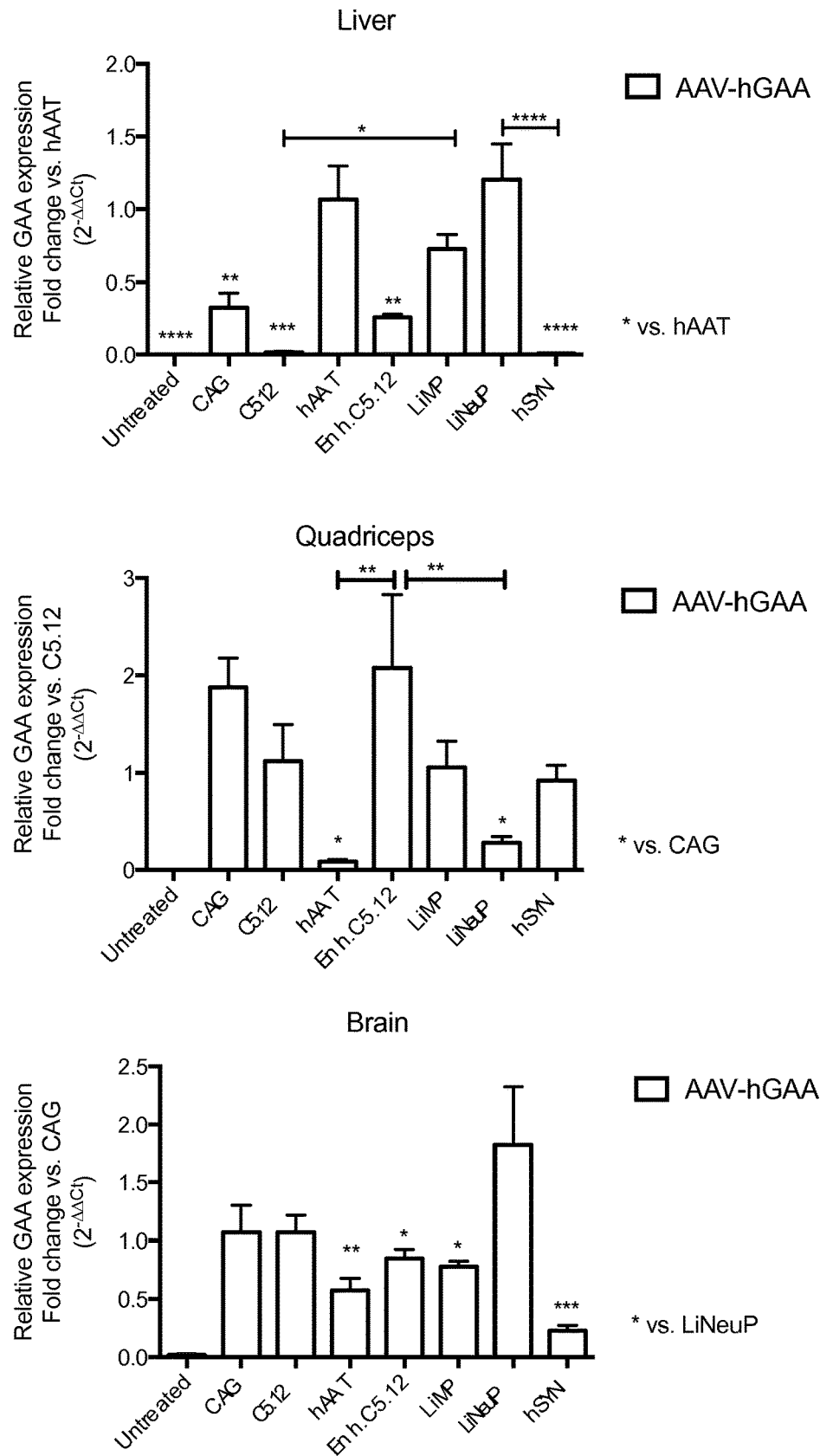
Figure 4B:
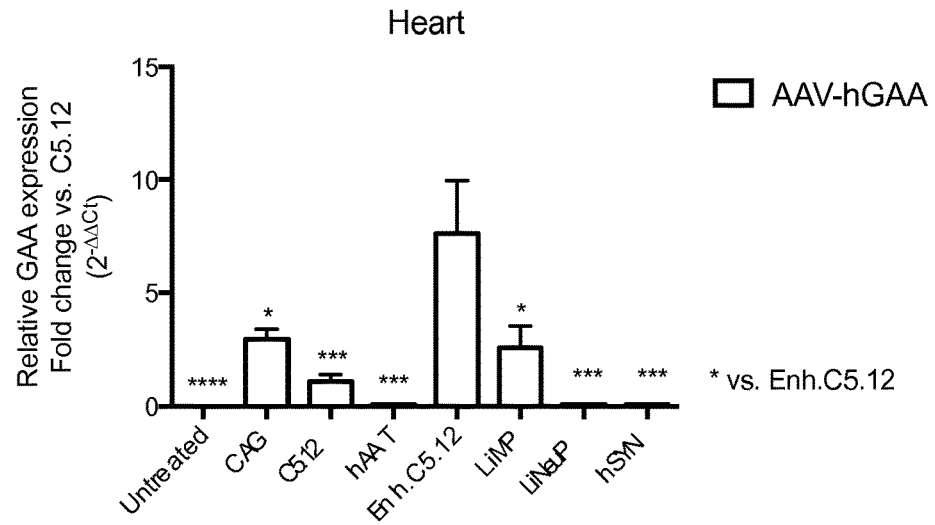
Figure 4B:
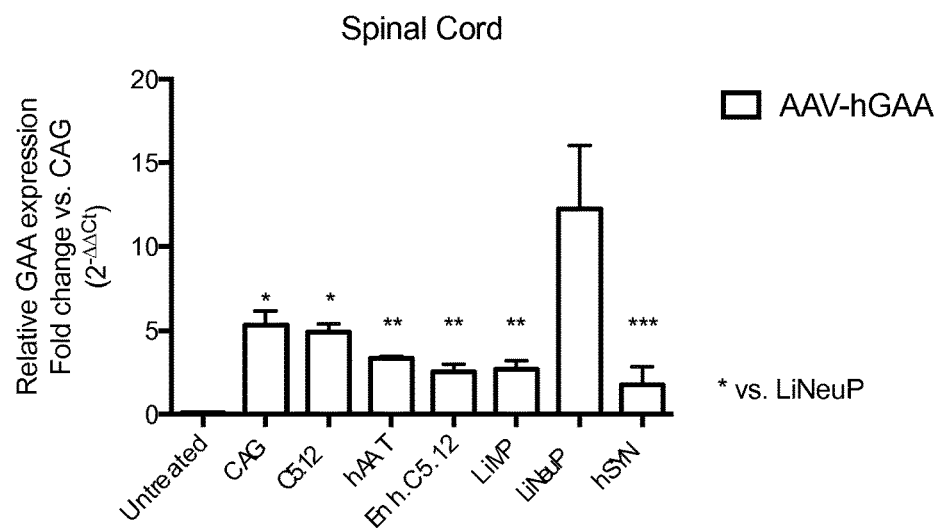
Figure 4B:
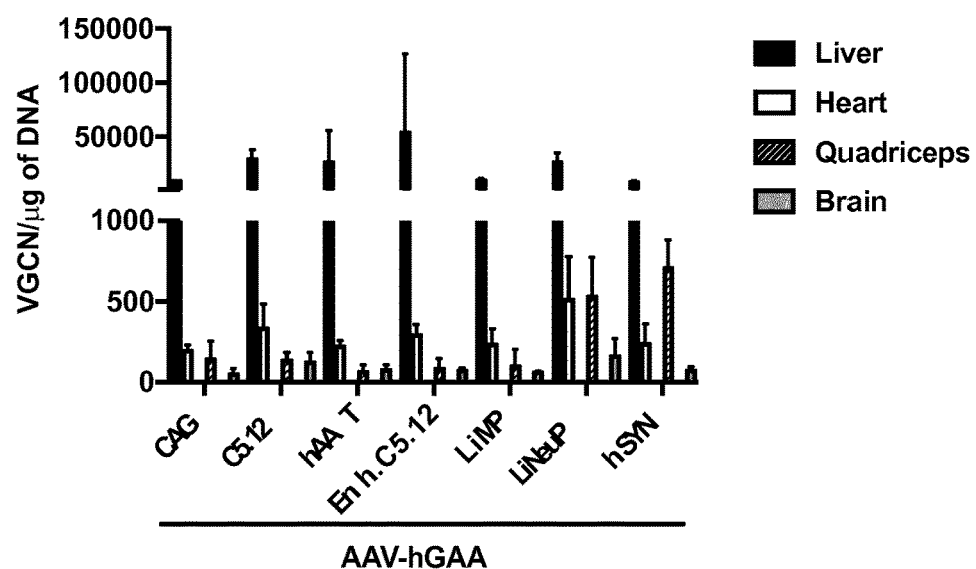

FIG. 4B. Human GAA RNA expression in wild type C57BL/6 mice.

Analysis of GAA expression 5 weeks following intravenous injection of an AAV9 vector harboring a full-length codon optimized GAA transgene (abbreviated as hGAA) under the control of ubiquitous (CAG), liver-selective (hAAT) and muscle-selective (C5.12) promoters or our newly generated liver-muscle (Enh.C5.12, LiMP) and liver-neurons (LiNeuP) promoters (AAV dose: $2\times10^{12}$ vg/kg). Human GAA RNA expression was evaluated in liver, heart, quadriceps, spinal cord and brain and normalized by the expression of the endogenous mouse Actin gene. The relative fold change expression is depicted. Untreated: not injected C57BL/6 mouse used as negative control. Vector genome copy number (VGCN) normalized per μg of DNA is depicted for tissues in which RNA and DNA extraction was possible. Statistical analysis: One-way ANOVA with Tukey post hoc for RNA expression or Two-way ANOVA (promoter and tissue) with Tukey post hoc for VGCN. $*p<0.05$, $p<0.01$, $*p<0.001$, $****p<0.0001$.

Figure 5A:
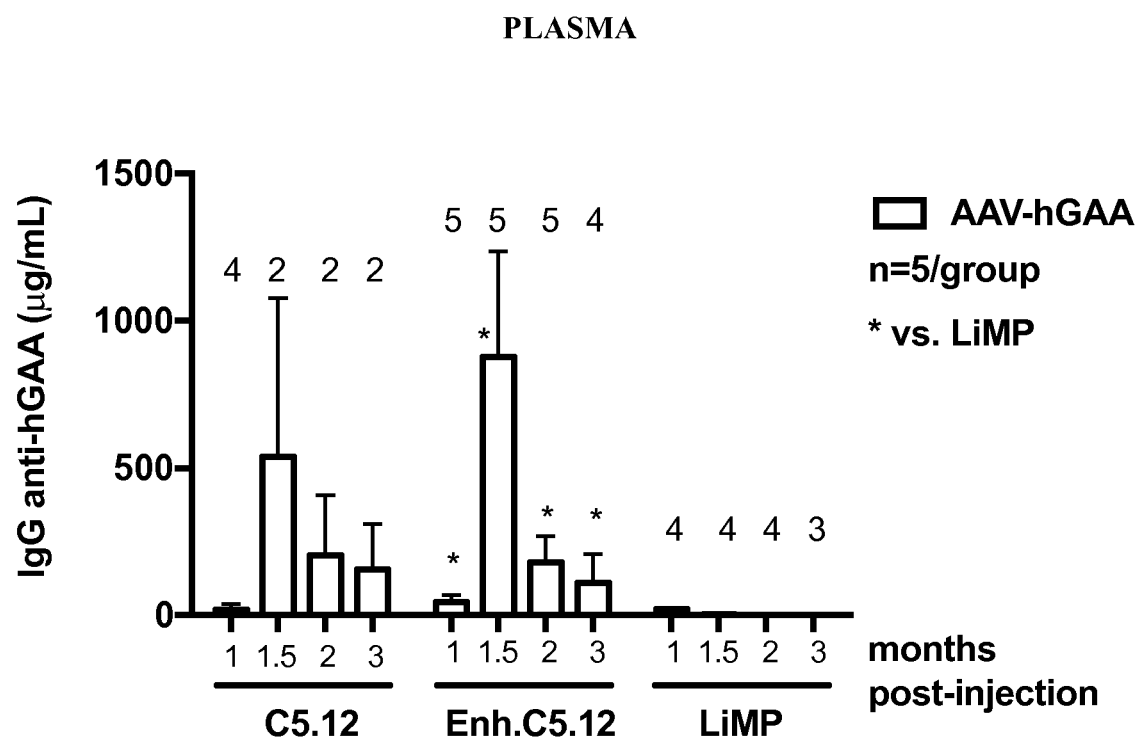
Figure 5B:
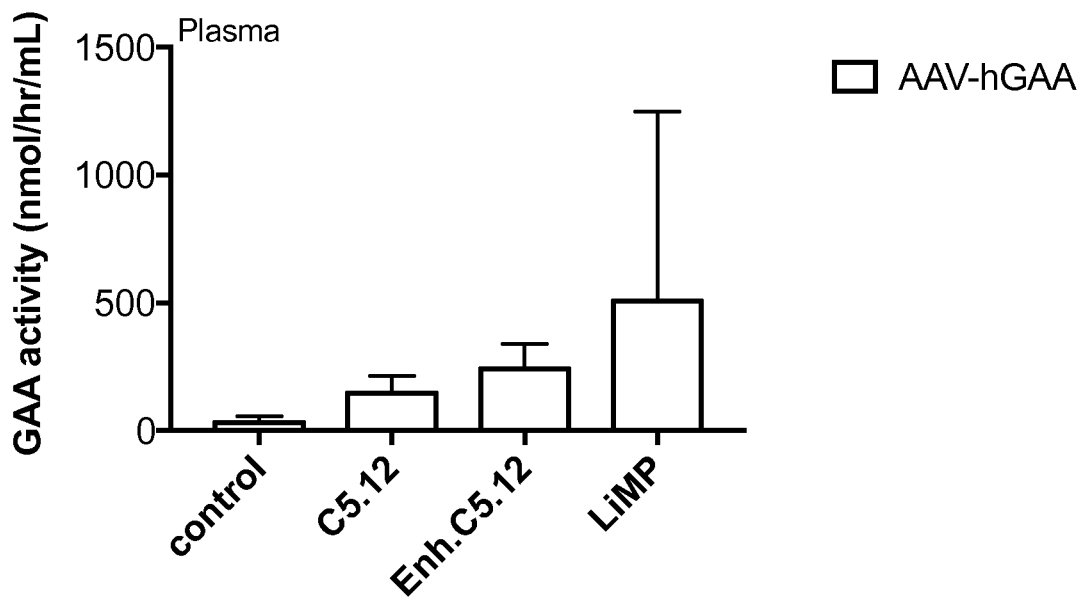
Figure 5B:
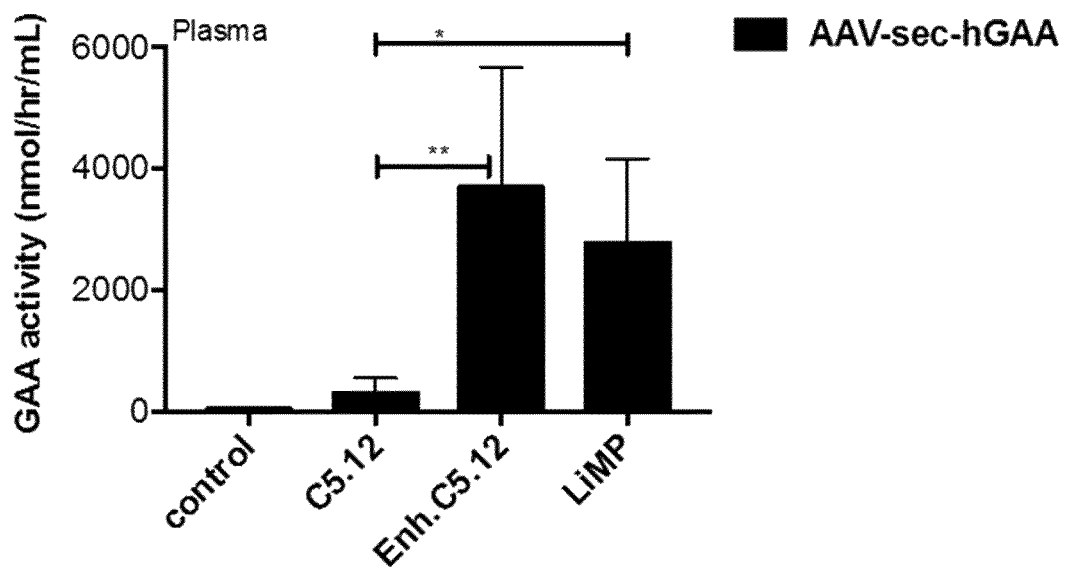

FIGS. 5A-5B. Humoral immune responses to GAA in adult Gaa−/− mice when using promoters active in muscle or liver-muscle.

Analysis of Anti-GAA antibodies (Immunoglobulin G: IgG; FIG. 5A) following intravenous injection of an AAV8 vector encoding a native (hGAA), and analysis circulating GAA enzyme activity (FIG. 5B) following intravenous injection of an AAV8 vector encoding a native (hGAA) or highly secretable GAA (sec-hGAA) under the control of the muscle-selective (C5.12) or our newly generated liver-muscle promoters Enh.C5.12 and LiMP (AAV8 dose: $2\times10^{12}$ vg/kg) in Gaa−/− mice. FIG. 5A. Anti-GAA IgG were measured from 1 to 3 months following intravenous injection of AAV8 vectors. Five mice/group were treated, the numbers above the bars indicate the number of live mice at each time point, the numbers below the bars indicate the month post-injection. Statistical analysis: Two-way ANOVA with Tukey post-hoc. FIG. 5B. Analysis of circulating GAA enzyme activity three months following intravenous injection of AAV8 vectors encoding for native GAA (hGAA) or highly secretable GAA (sec-hGAA). Statistical analysis: One way ANOVA with Tukey post-hoc. Control: plasma from untreated Gaa−/− littermate mice. $*p<0.05$, $p<0.01$, $*p<0.001$, $****p<0.0001$.

Figure 6:
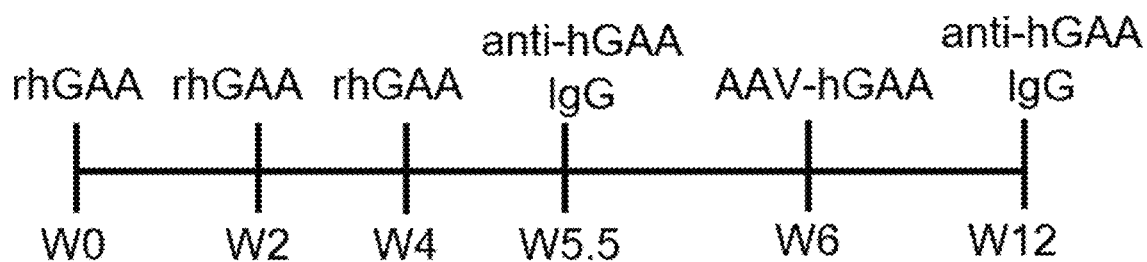
Figure 6:
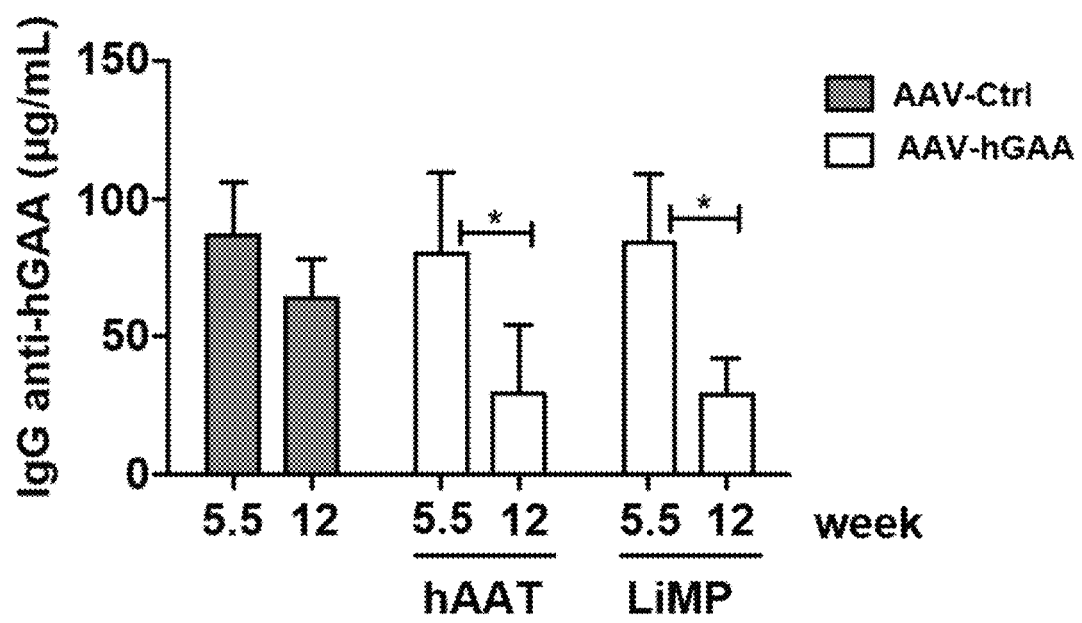

FIG. 6: Anti-hGAA humoral immune responses in Gaa−/− mice following AAV gene transfer of hGAA using dual promoters after recombinant hGAA injection.

(A) Experimental design: 2-month old Gaa−/− were immunized by intravenous injection of the recombinant human GAA protein (rhGAA). Six week later the immunized Gaa−/− were treated by intravenous injection of AAV9-hGAA vectors (dose: $2\times10^{12}$ vg/kg) harboring the dual liver-muscle LiMP promoter or the hepatocyte-specific hAAT promoter; AAV9 vectors encoding for luciferase were used as control (AAV-Ctrl, dose: $2\times10^{12}$ vg/kg). Anti-hGAA IgG were measured as indicated (W: week). (B) Analysis of anti-hGAA IgG in Gaa−/− mice at 5.5 and 12 weeks (see panel C). Data are depicted as average+SD; AAV-hGAA n=3 mice/cohort; AAV-Ctrl n=2 mice/cohort. Statistical analysis: Two-way ANOVA (AAV, week) with Sidak post-hoc. $*p<0.05$, $**p<0.01$, $\#\#p<0.01$.

Figure 7:
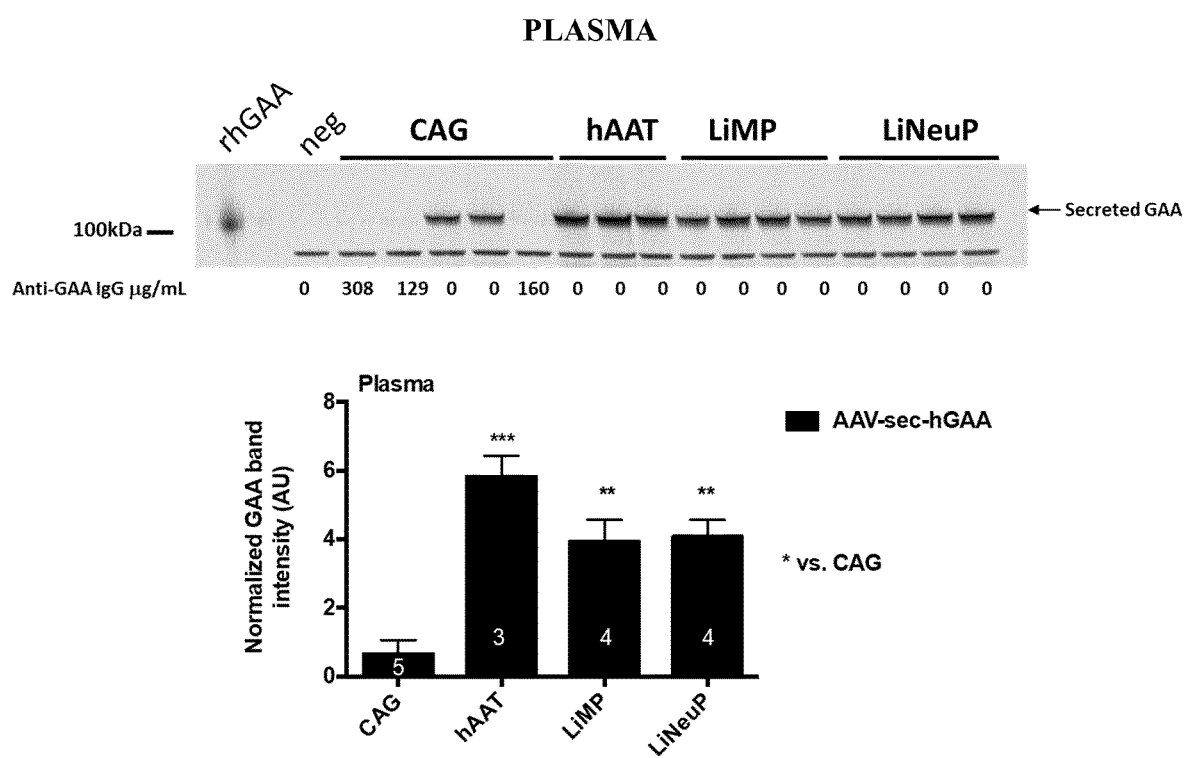

FIG. 7. Circulating GAA protein and anti-GAA IgG in adult Gaa−/− mice when using hybrid promoters very active in the liver (LiMP and LiNeuP).

Analysis of circulating GAA protein 4 weeks following intravenous injection of an AAV9 vector encoding a highly secretable GAA protein (sec-hGAA), under the control of ubiquitous (CAG) promoter, liver-selective (hAAT) promoter, and our newly generated liver-muscle (LiMP) and liver-neuron (LiNeuP) promoters (AAV dose: $5\times10^{11}$ vg/kg). Top panel: Western blot of mouse plasma with anti-GAA antibody; the humoral response to GAA (IgG) measured in mouse plasma at the same time point is depicted under each corresponding lane. rhGAA: recombinant human GAA used as positive control; molecular weight marker (kDa on the left); neg: mouse plasma from uninjected Gaa−/− mice used as negative control. The number of mice per group is depicted in the bars. Bottom panel: Quantification of GAA protein bands. The GAA band intensity was normalized by the intensity of the non-specific band detected in plasma and used as loading control. Statistical analyses: One-way ANOVA with Tukey post-hoc. $*p<0.05$, $p<0.01$, $*p<0.001$, $****p<0.0001$.

Figure 8:
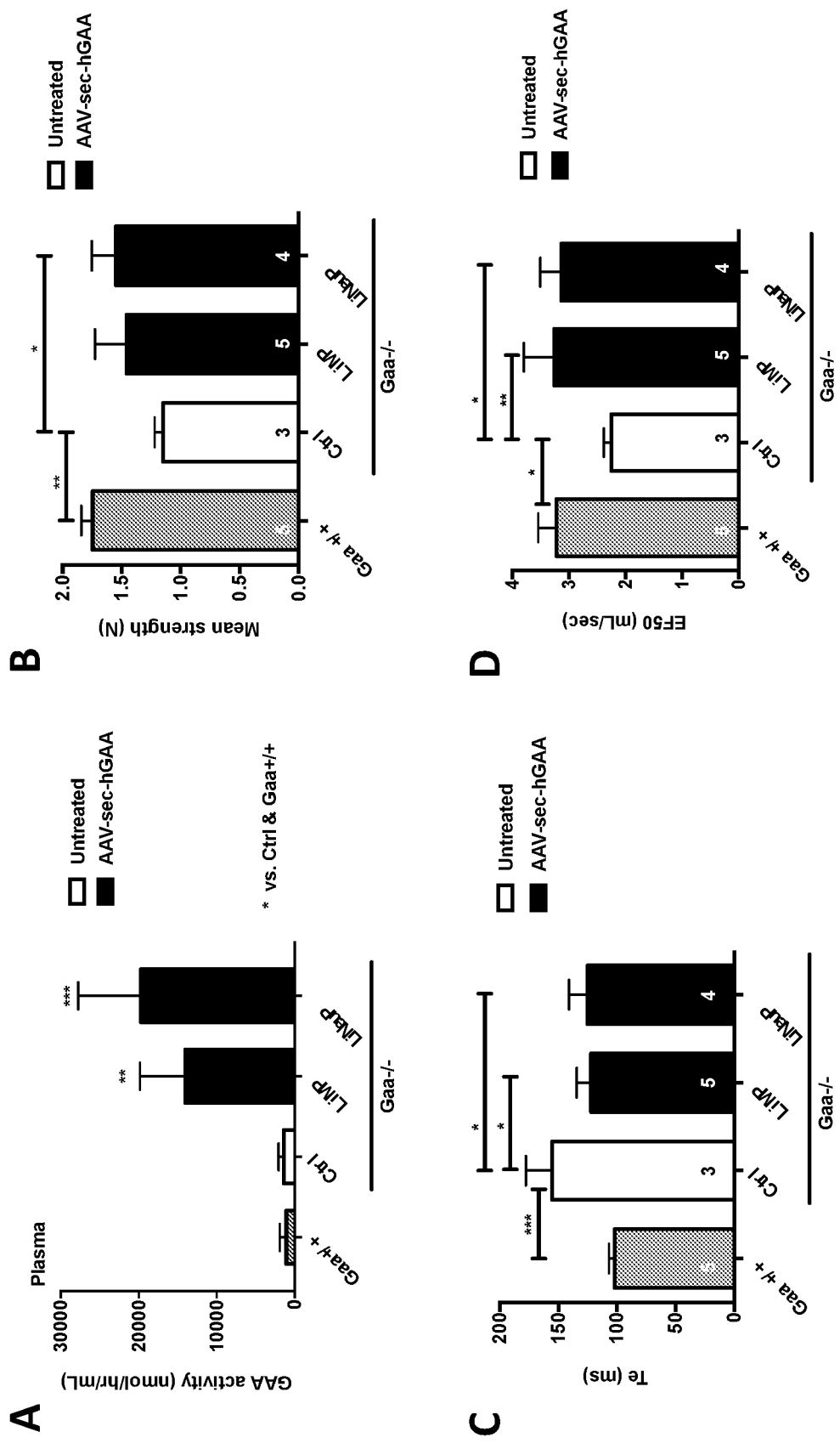

FIG. 8. Rescue of muscle strength and respiratory function in adult Gaa−/− mice when using hybrid promoters active in the liver (LiMP and LiNeuP).

Analysis of plasma GAA enzyme activity (A), muscle strength (B) and respiratory function (C, D) following intravenous injection of an AAV9 vector encoding for a highly secretable GAA (sec-hGAA) under the control of our newly generated liver-muscle (LiMP) and liver-neuron (LiNeuP) promoters (AAV9 dose: $2\times10^{12}$ vg/kg) in Gaa−/− mice. (A) Analysis of circulating GAA enzyme activity 2 months following intravenous injection of AAV9 vectors. Analysis of and muscle strength by 4-paths grip test (B) and respiratory function by whole-body plethysmography (C, D) 3 months following intravenous injection of AAV9 vectors. Te: expiratory time; EF50: (mid-expiratory flow); Ctrl: untreated Gaa−/− mice used as control treatment group. Gaa+/+: wild type unaffected littermate mice. Statistical analysis: A. One way ANOVA with Tukey post-hoc; One way ANOVA vs. Ctrl with Dunnet's post-hoc. $*p<0.05$, $p<0.01$, $*p<0.001$, $****p<0.0001$.

Figure 9:
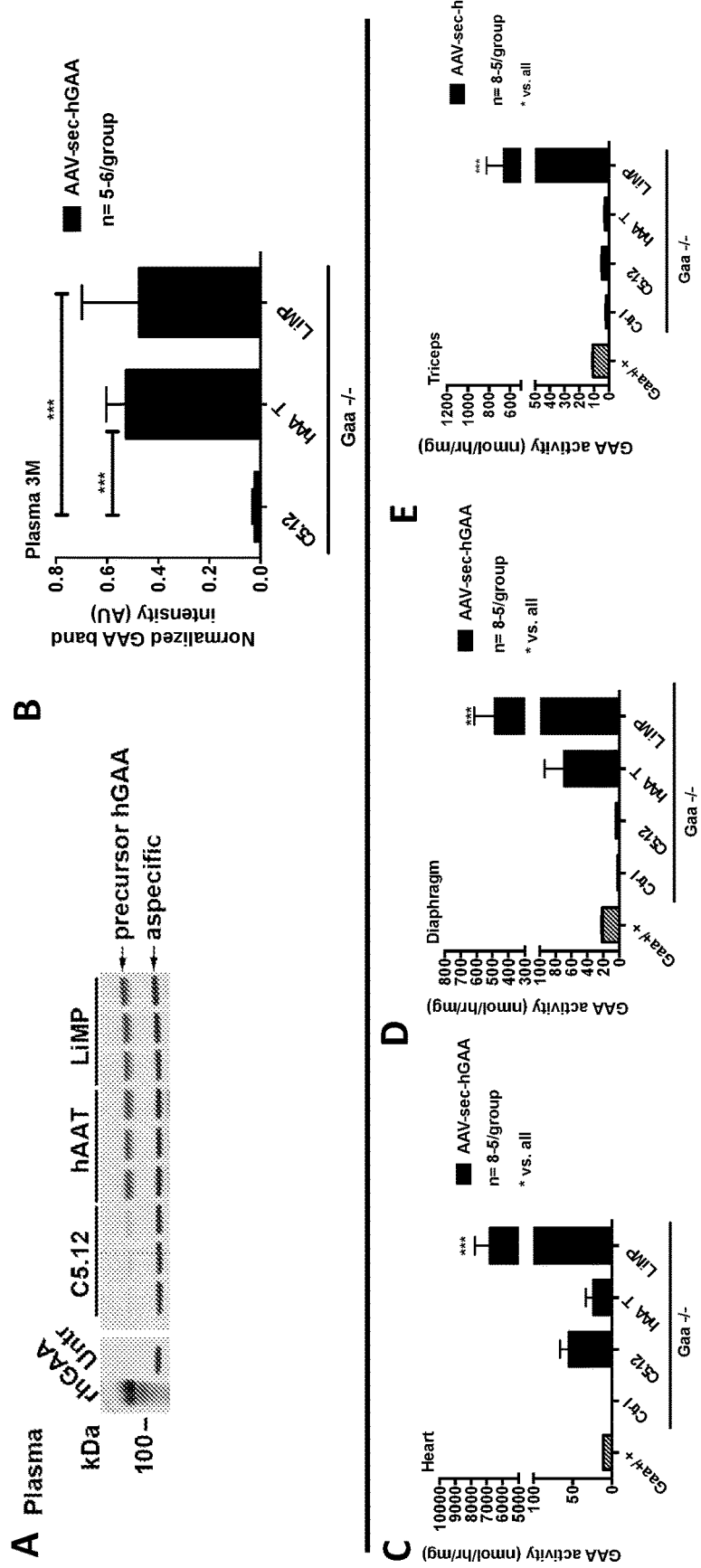
Figure 9:
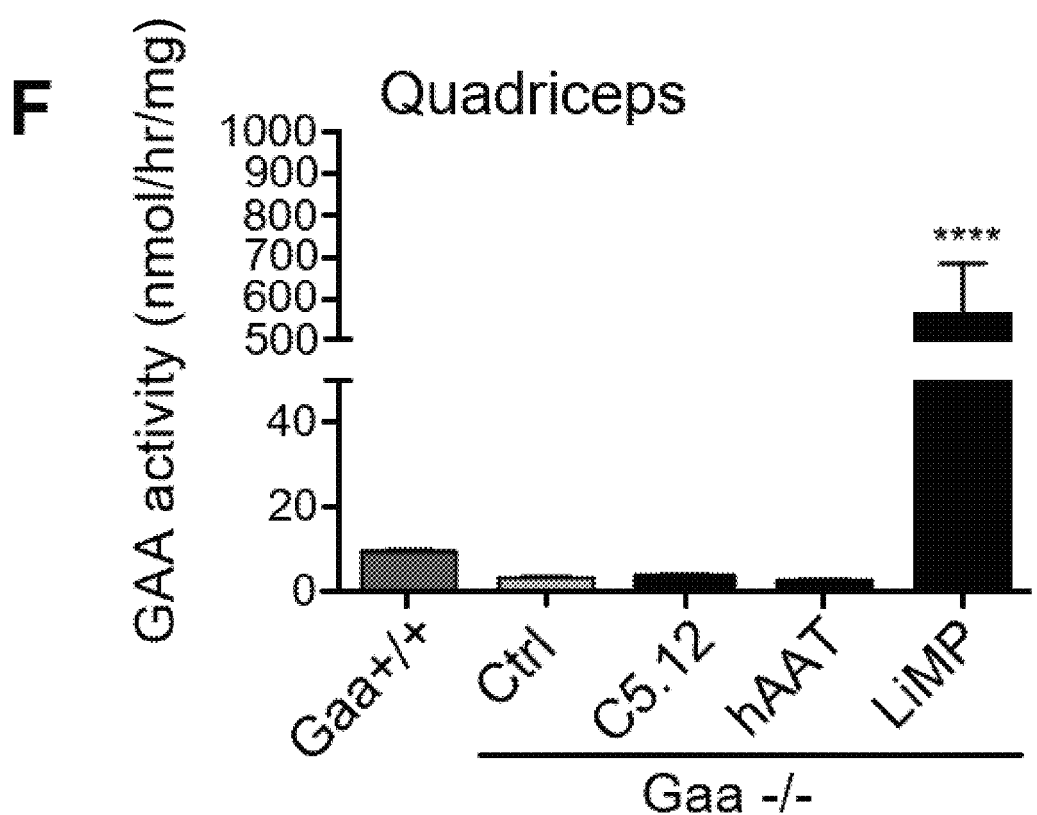

FIG. 9. Activity of hybrid liver-muscle promoter LiMP in newborn Gaa−/− mice.

Analysis of GAA protein 3 months following intravenous injection of an AAV8 vector encoding for a highly secretable GAA protein (sec-hGAA) under the control of the muscle-selective (C5.12), liver-selective (hAAT) or our newly generated hybrid liver-muscle promoter LiMP, that has increased activity in both muscle and liver (see FIGS. 2 and 4B, AAV dose: $3 \times 10^{13}$ vg/kg). A-B: Representative Western blot analysis of mouse plasma with anti-GAA antibody 3 months post-treatment; rhGAA: recombinant human GAA used as positive control; Untr: plasma from untreated Gaa-/-mouse used as negative control; the molecular weight marker (kDa) is depicted on the left. The quantification of GAA bands is shown in panel B. Statistical analyses: One-way ANOVA with Tukey post-hoc.C-F: Analysis of GAA activity in heart, diaphragm, triceps and quadriceps muscles 3 months following intravenous injection of an AAV8 vectors. Ctrl: untreated Gaa-/- mice. Statistical analyses: One-way ANOVA with Tukey post-hoc. Gaa+/+: wild type unaffected littermate mice;*p<0.05, p<0.01, *p<0.001, ****p<0.0001.

Figure 10:
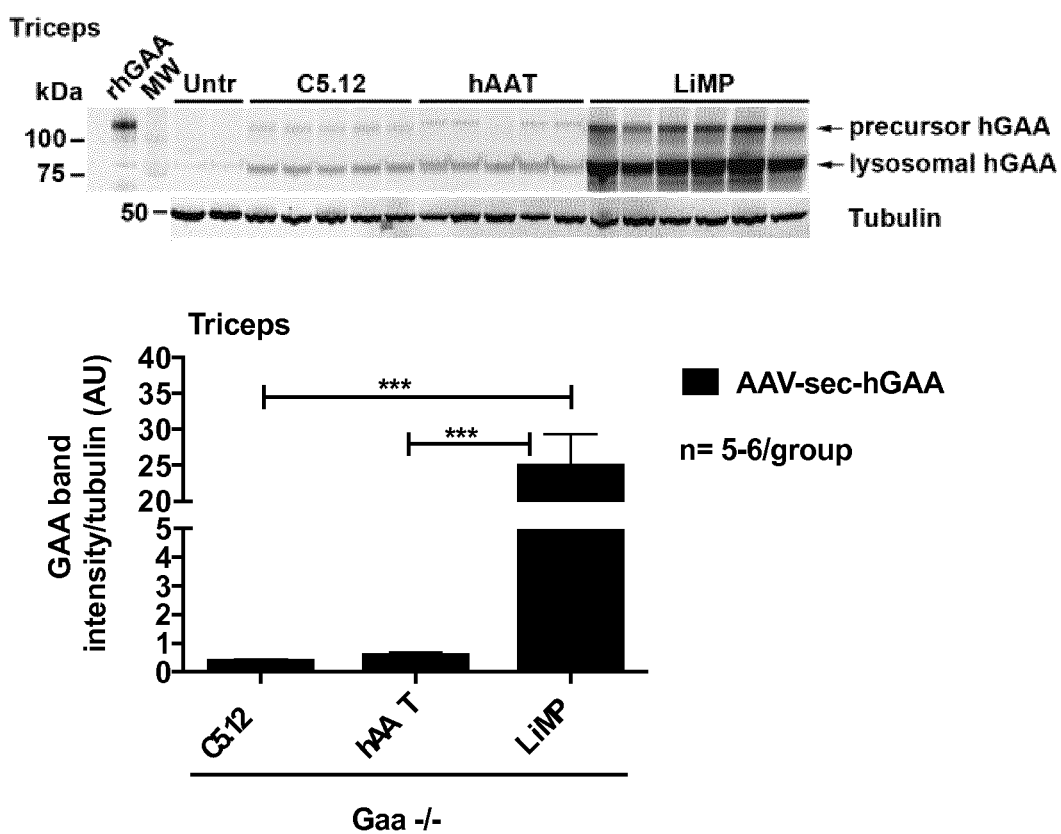
Figure 10:
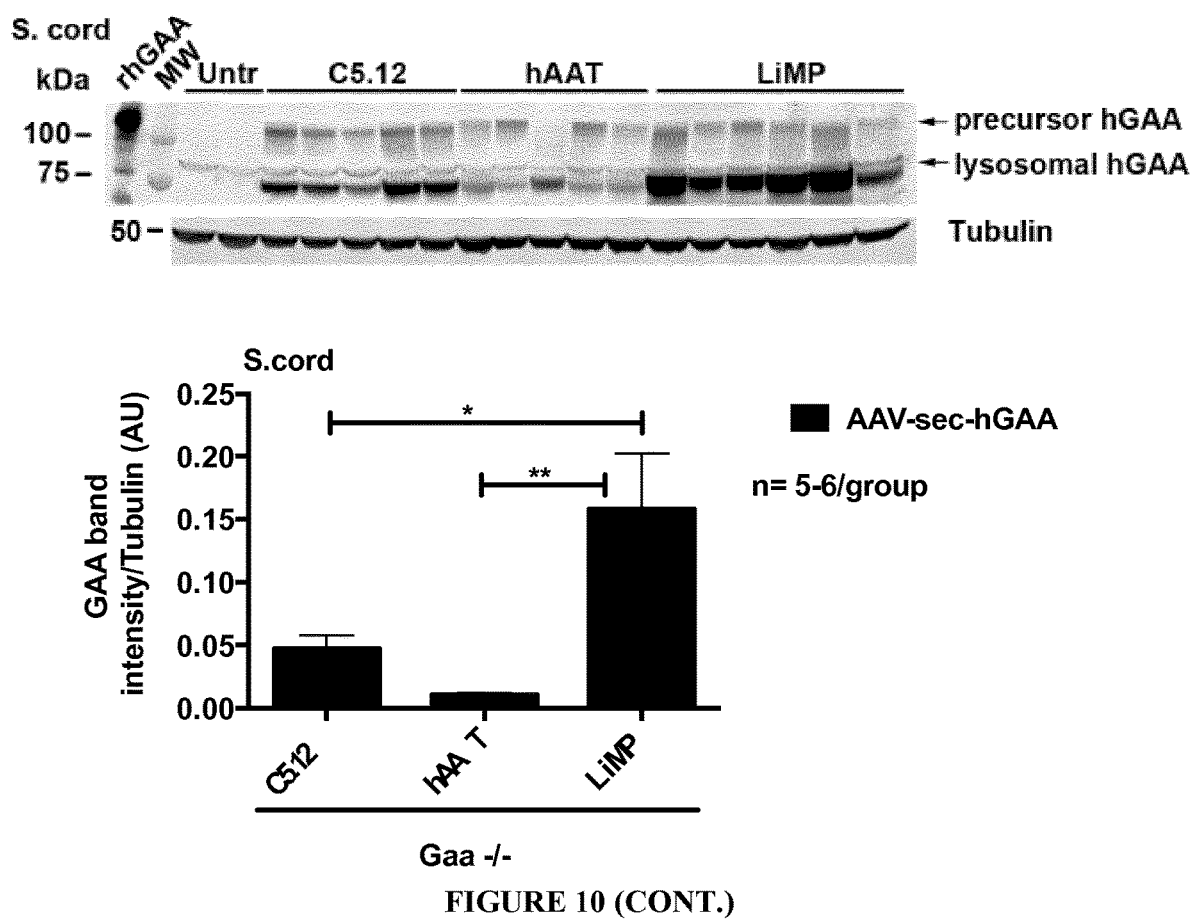
Figure 10:
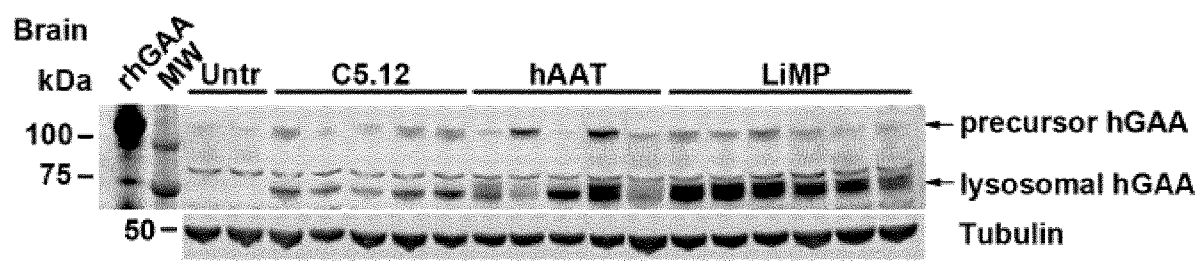
Figure 10:
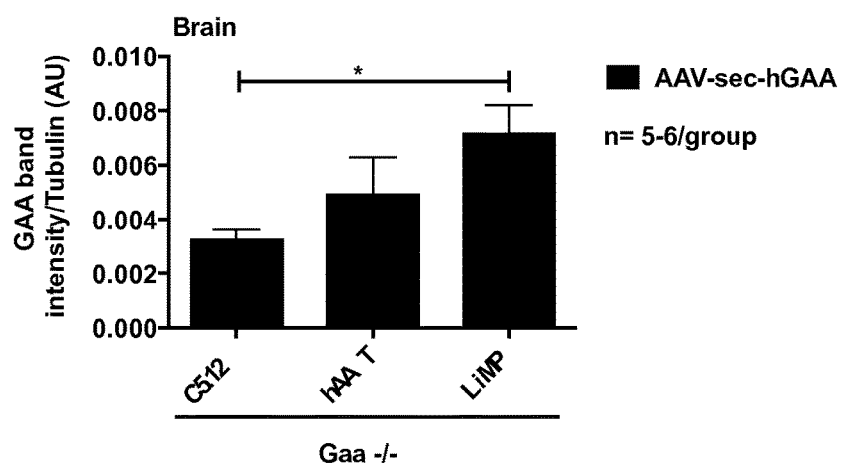
Figure 10:
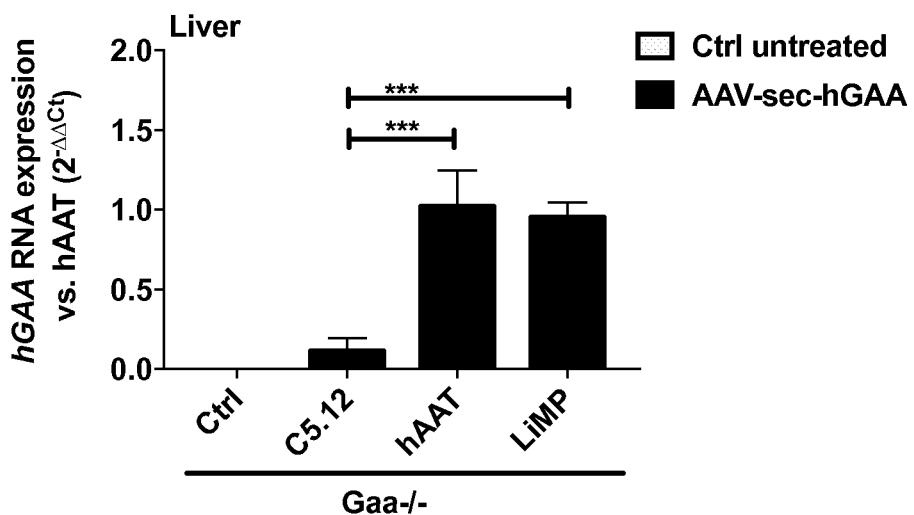
Figure 10:
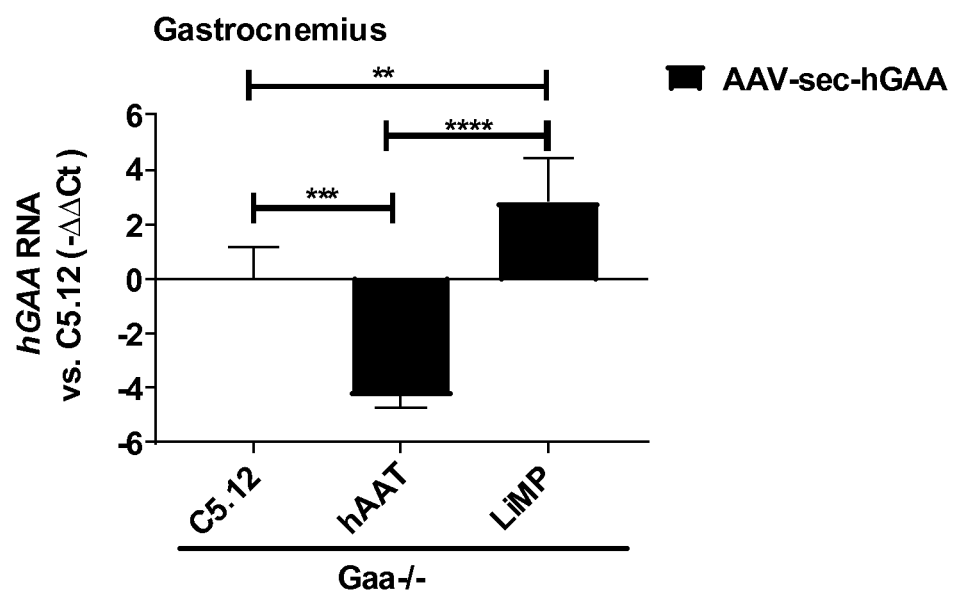

FIG. 10. Analyses of GAA protein amount in muscle and CNS upon AAV gene therapy with the hybrid liver-muscle promoter LiMP in Gaa-/- mice treated as neonates.

Analysis of GAA protein in triceps, spinal cord and brain 3 months following intravenous injection of an AAV8 vector encoding for a highly secretable GAA protein (sec-hGAA) under the control of the muscle-selective (C5.12), liver-selective (hAAT) or our newly generated hybrid liver-muscle promoter LiMP in newborn Gaa-/- mice (AAV dose: $3 \times 10^{13}$ vg/kg). A-C: Western blot analysis of mouse tissues with anti-GAA antibody 3 months post-treatment. Anti-Tubulin antibodies were used as loading control; rhGAA: recombinant human GAA used as positive control; Untr: tissues from untreated Gaa-/- mice used as negative control; the molecular weight marker (kDa) is depicted on the left. The quantification of GAA bands is shown. The GAA band intensity was normalized by the intensity of the Tubulin band used as loading control. D. Relative expression (fold change) of the sec-hGAA transgene RNA in the liver of Gaa-/- mice performed by RT-qPCR. The fold change transgene expression is depicted in comparison to hAAT. E. Relative expression ($-\Delta\Delta$Ct) of the sec-hGAA transgene RNA in the gastrocnemius of AAV-treated Gaa-/- mice performed by RT-qPCR. The relative transgene expression ($-\Delta\Delta$Ct) is depicted in comparison to C5.12. A-E. Statistical analyses: One-way ANOVA with Tukey post-hoc. Gaa+/+: wild type unaffected littermate mice; Untr: untreated Gaa-/- mice. *p<0.05, p<0.01, *p<0.001, ****p<0.0001.

Figure 11:
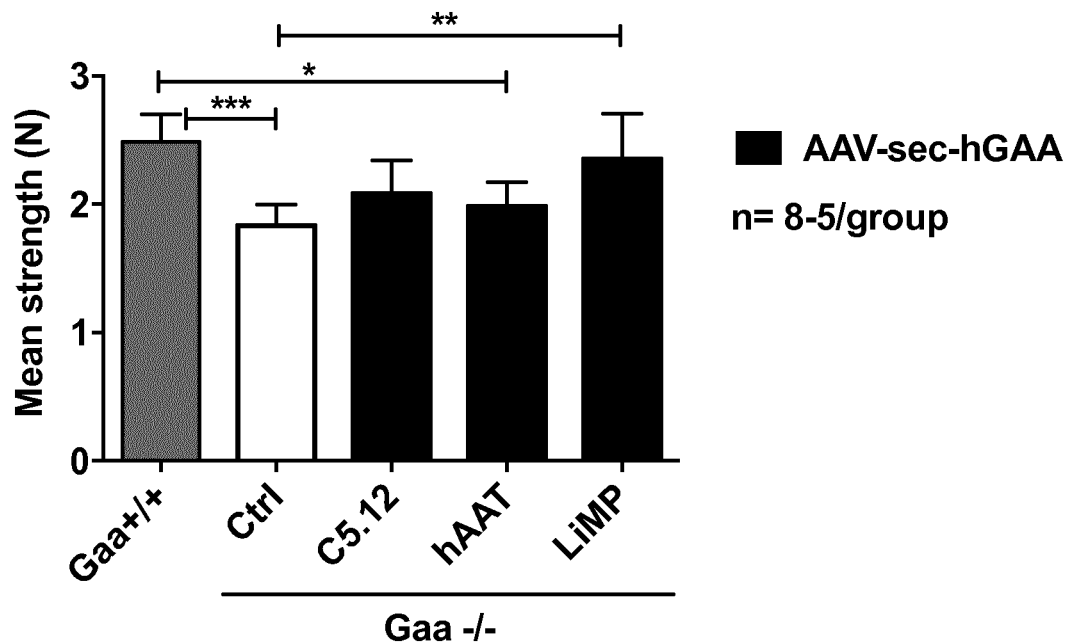

FIG. 11. Preservation of muscle strength with AAV-LiMP-sec-hGAA in Gaa-/- mice treated as neonates.

Analysis of muscle strength by Grip test in Gaa+/+ wild type unaffected littermate mice and Gaa-/- mice 3 months following intravenous injection of an AAV8 vectors encoding for a highly secretable GAA protein (sec-hGAA) under the control of the muscle-selective (C5.12), liver-selective (hAAT) or our newly generated liver-muscle promoter LiMP that has increased activity in both muscle and liver (see FIGS. 2 and 4B, AAV dose: $3 \times 10^{13}$ vg/kg). Gaa+/+: wild type unaffected littermate mice; Ctrl: untreated Gaa-/- mice. Statistical analyses: One-way ANOVA with Tukey post-hoc. *p<0.05, p<0.01, *p<0.001, ****p<0.0001.

Figure 12:
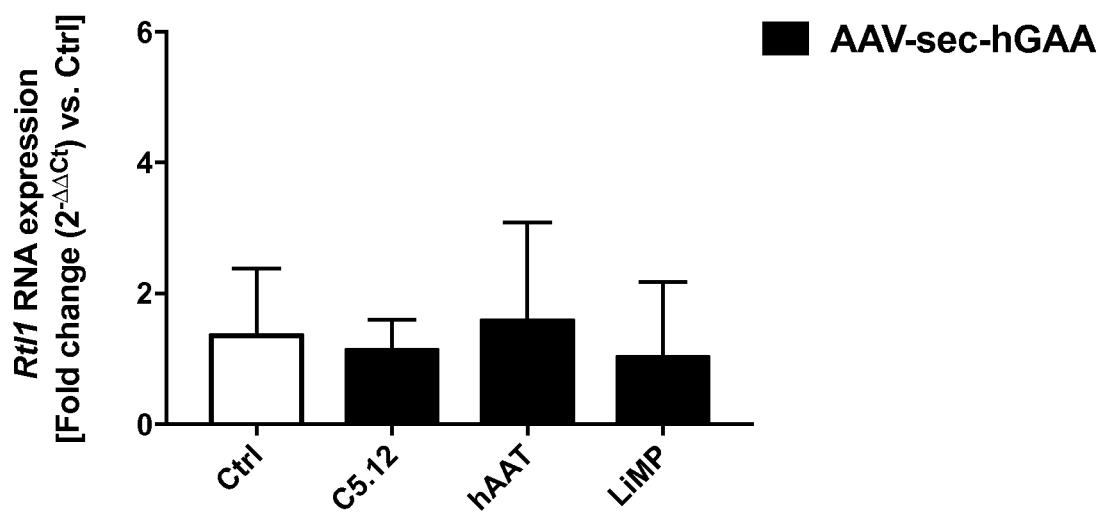

FIG. 12. Lack of upregulation of Rtl1 RNA following delivery of AAV-LiMP-sec-hGAA to newborn Gaa-/- mice.

Analysis of Rtl1 RNA expression in Gaa-/- mice 3 months following intravenous injection of an AAV8 vectors encoding for a highly secretable GAA protein (sec-hGAA) under the control of the muscle-selective (C5.12, n=3 mice), liver-selective (hAAT, n=4 mice) or our newly generated liver-muscle promoter LiMP (n=3 mice). AAV dose: $3 \times 10^{13}$ vg/kg. Ctrl: untreated Gaa-/- mice (n=4). Statistical analyses: One-way ANOVA with Tukey post-hoc, no significant differences were observed.

Figure 13:
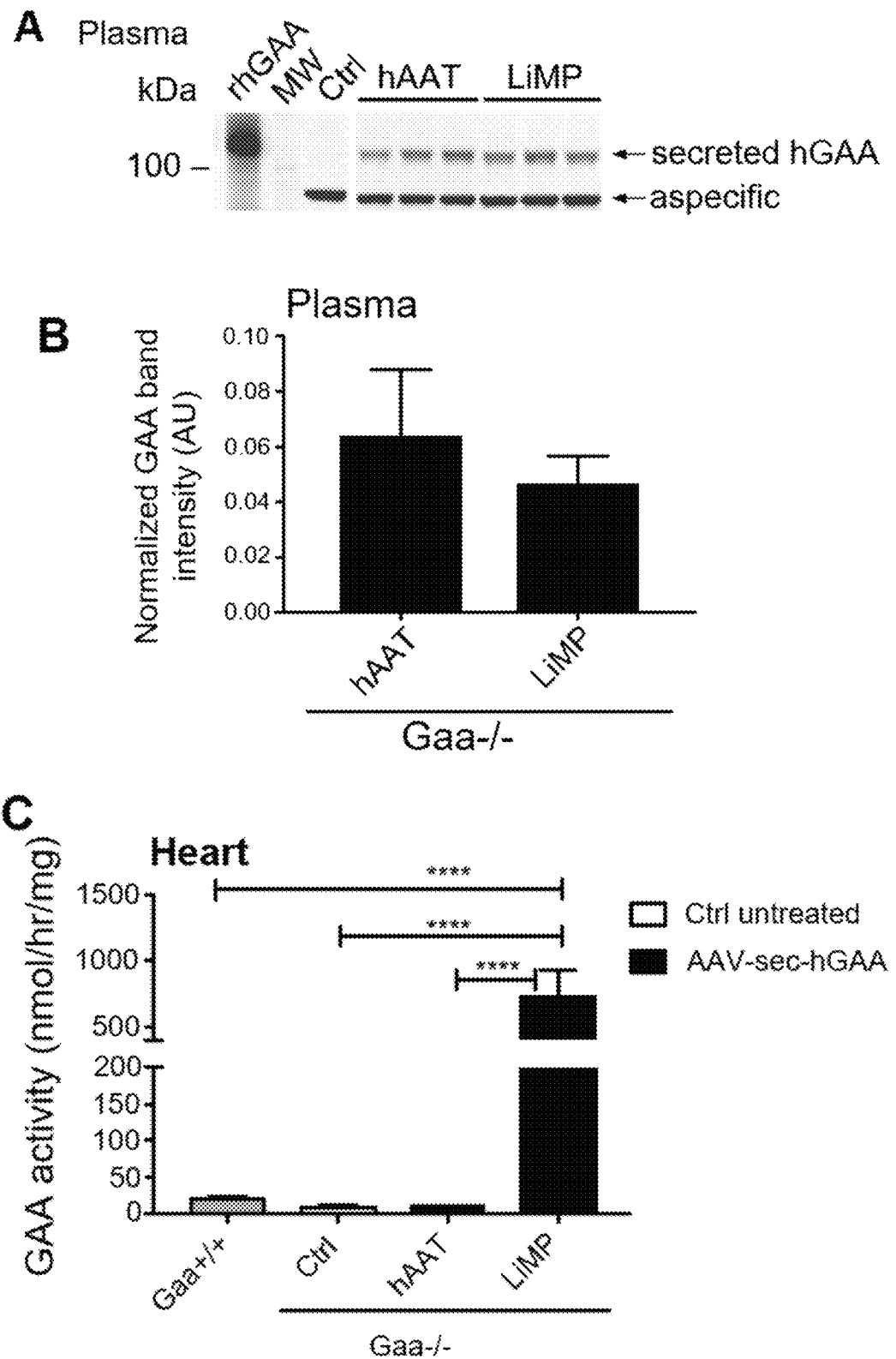
Figure 13:
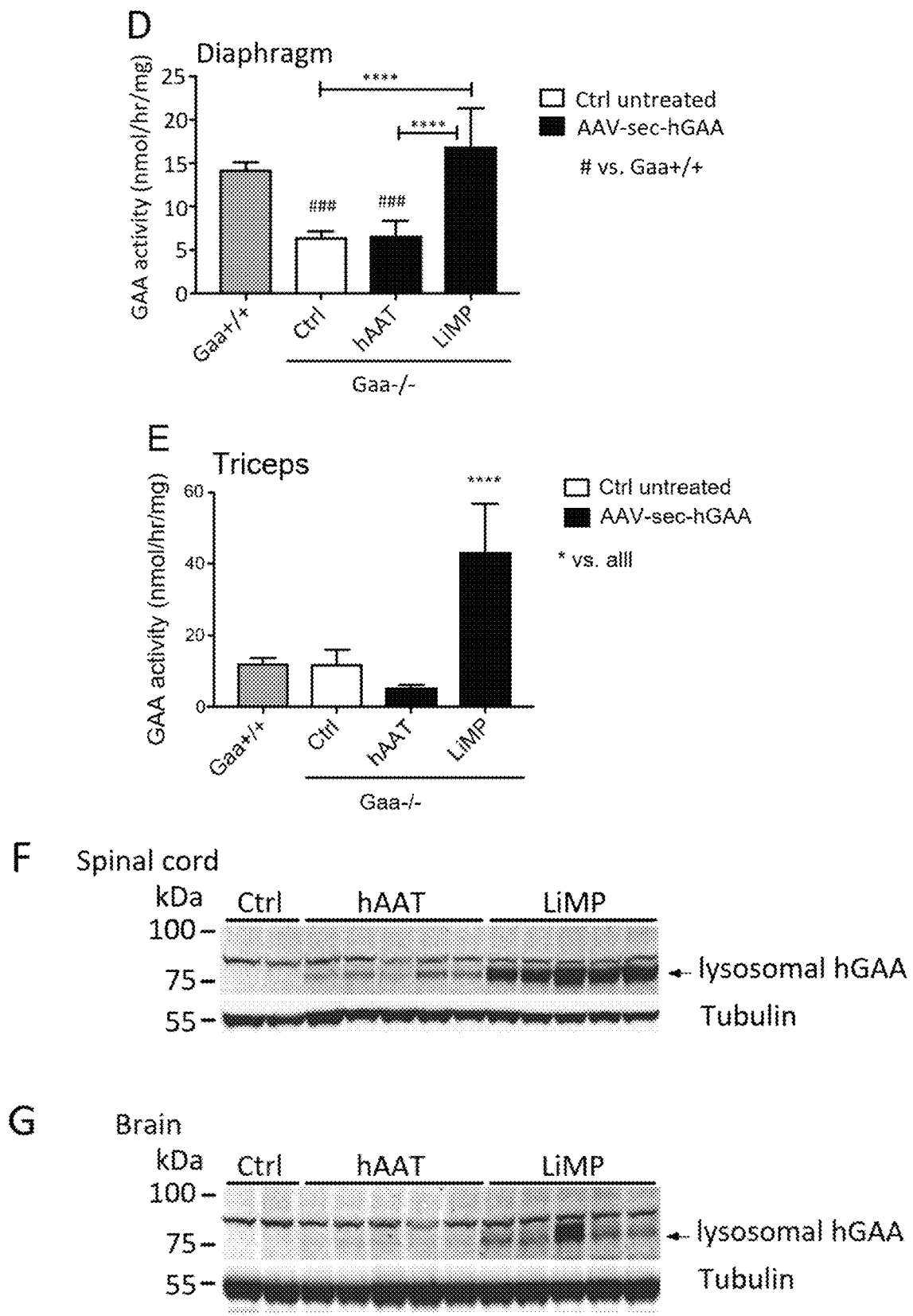
Figure 13:
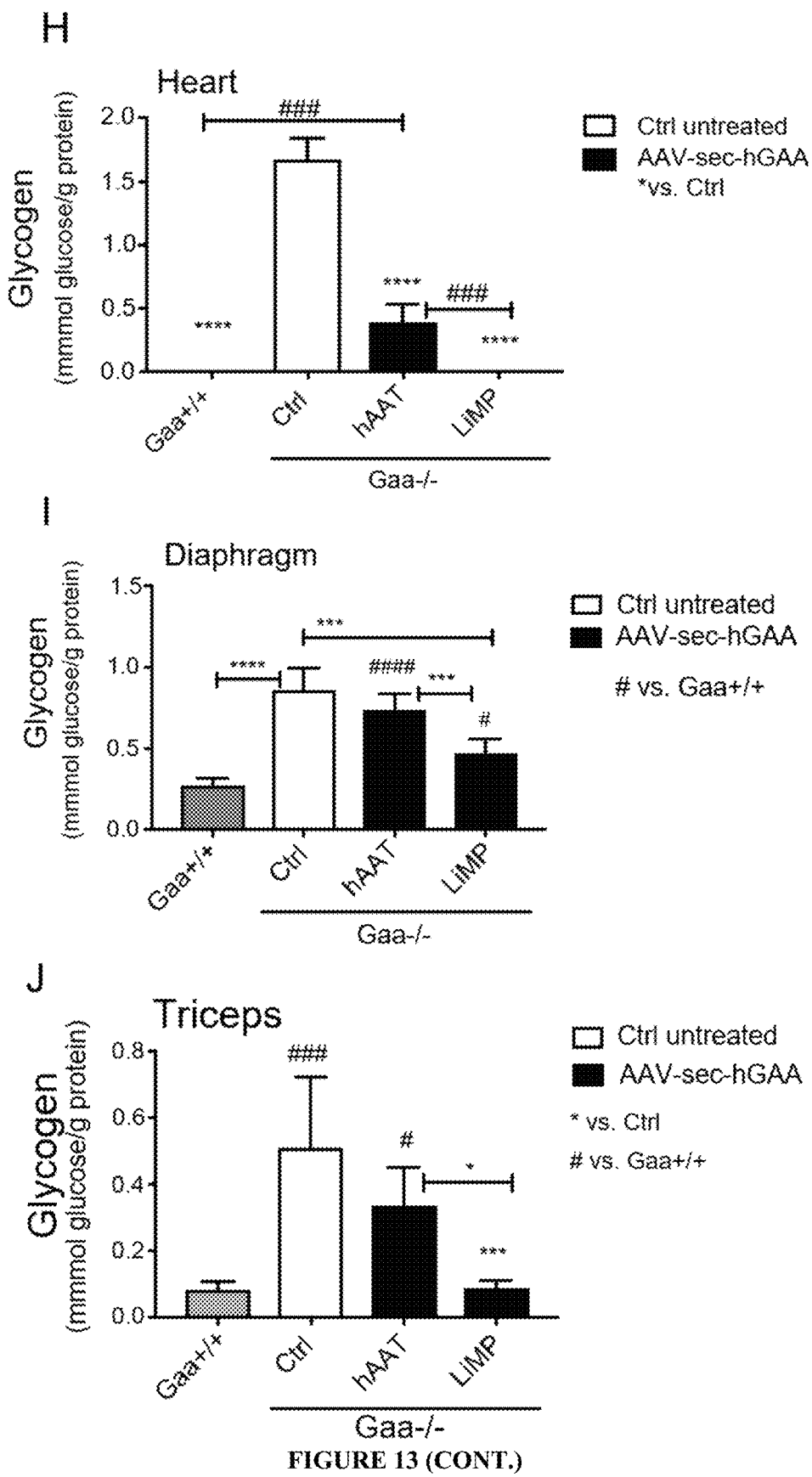
Figure 13:
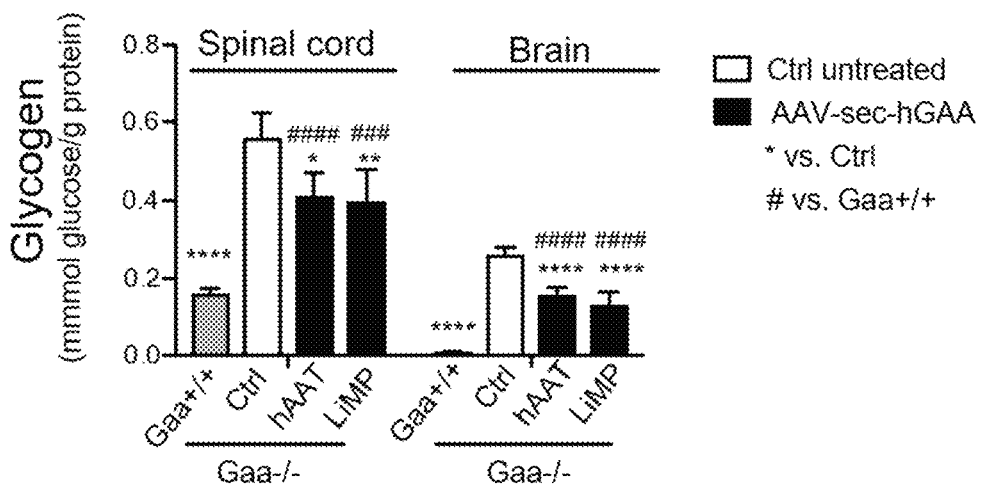
Figure 13:
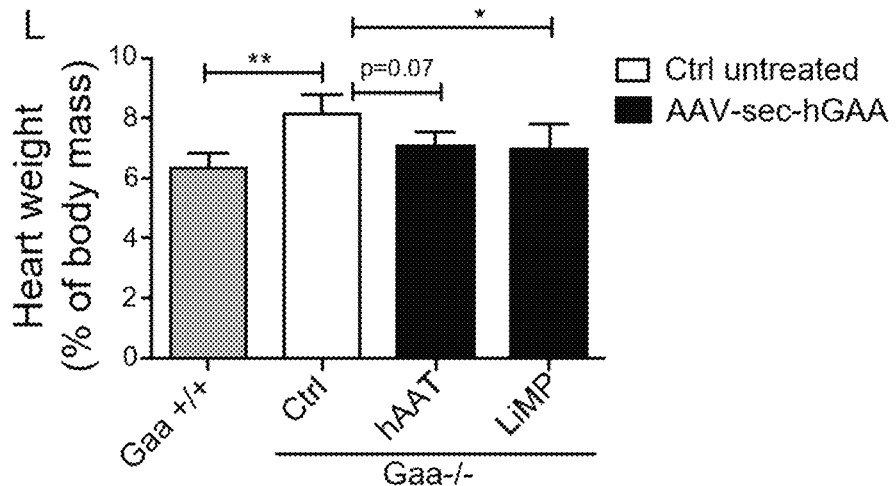
Figure 13:
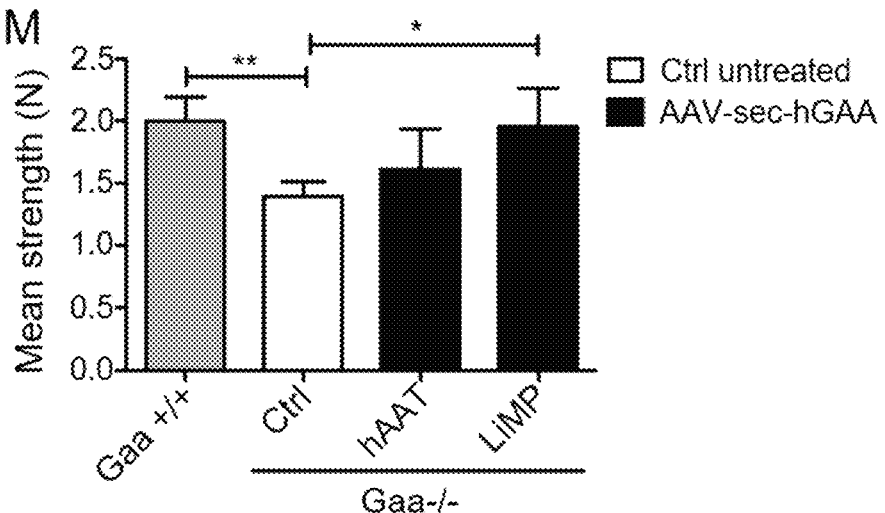

FIG. 13. Rescue of the disease phenotype of Gaa-/- mice treated as neonates with low dose AAV gene therapy using the LiMP promoter.

Analysis of hGAA transgene expression (A-G) and rescue of disease phenotype (H-M) in 4-month old Gaa-/- mice treated as neonates by intravenous injection of AAV9 vectors (dose: $6 \times 10^{12}$ vg/kg) encoding for a codon-optimized highly secretable human GAA (sec-hGAA) under the control of the dual liver-muscle LiMP promoter (n=5), or hepatocyte-specific (hAAT, n=5), as comparison. Untreated Gaa-/- mice were used as affected controls (Ctrl, n=5); littermate Gaa+/+ mice were used as unaffected controls (Gaa+/+, n=6). (A) Representative Western blot of Gaa-/- plasma with anti-human GAA antibody. The molecular weight marker (kDa) is depicted; rhGAA: recombinant human GAA loaded as positive control. (B) Quantification of hGAA protein band in Gaa-/- plasma. (C-E) Analysis of GAA enzyme activity in muscles. (F-G) Western blot analyses of Gaa-/- spinal cord (F) and brain (G) with anti-human GAA antibody; anti-tubulin antibody was used as loading control. The molecular weight marker (kDa) is depicted. (H-K). Glycogen accumulation measured in muscle (H-J) and central nervous system (K). (L) Heart weight normalized by body weight. (M) Muscle strength measured by 4-limb grip test. (B-E, H-M) Data are depicted as average+ SD; n=6-5 mice per cohort as described above. Statistical analysis: t-test (B), one-way ANOVA with Tukey posthoc (C-E, H-M). *p<0.05, p<0.01, *p<0.001, ****p<0.0001, #p<0.05, ###p<0.001. Asterisks and hash marks on the bars show significant differences vs. mouse cohorts specified in the graph legends.

Figure 14:
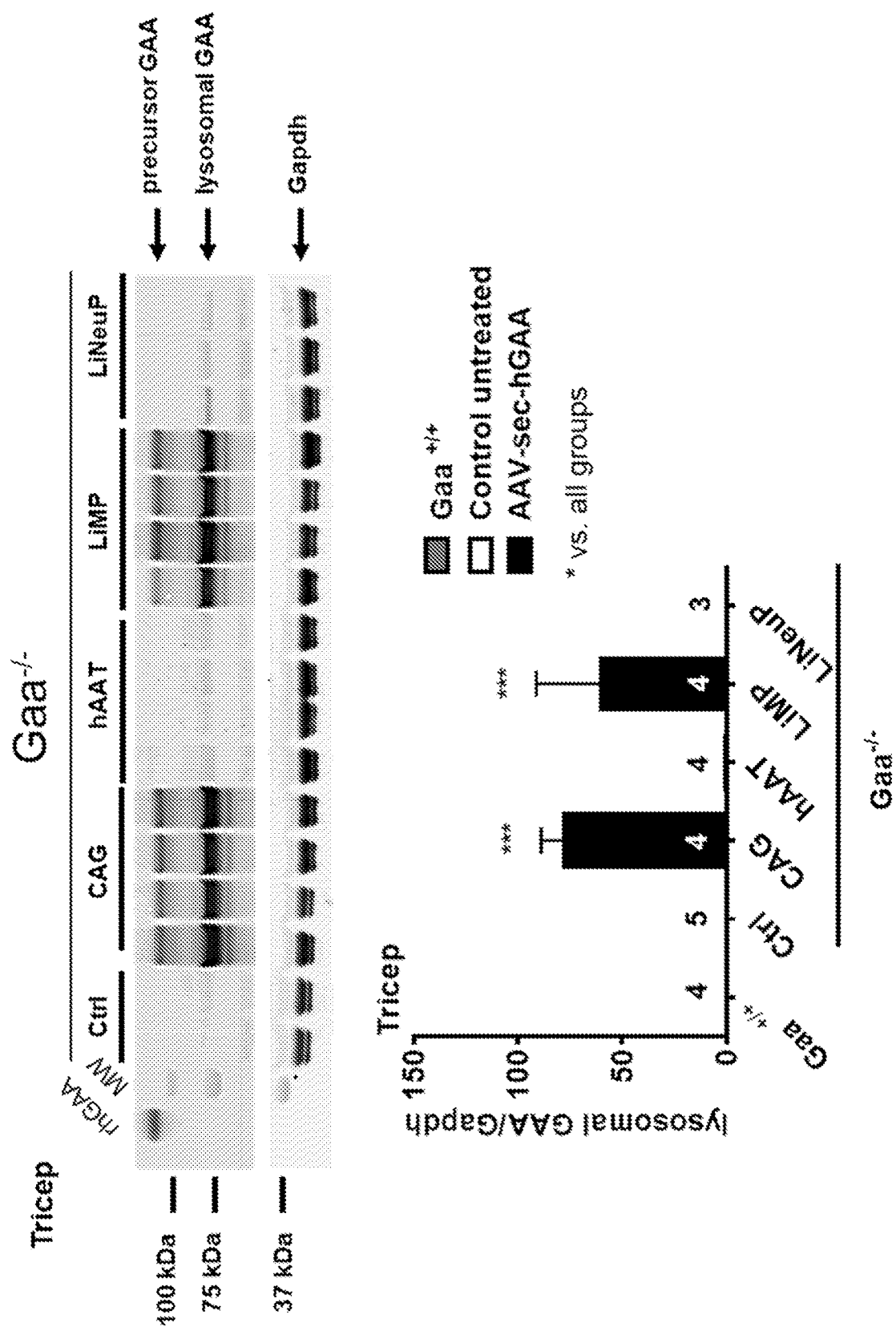

FIG. 14. Analyses of GAA protein amount in muscle upon AAV gene therapy with the hybrid liver promoters LiMP and LiNeuP in Gaa-/- mice treated as neonates.

Analysis of GAA protein in triceps, 4 months following intravenous injection of an AAV9 vector encoding for a highly secretable GAA protein (sec-hGAA) under the control of the ubiquitous (CAG) promoter, liver-specific (hAAT) promoter or our newly generated hybrid liver-muscle LiMP or liver-neuron LiNeuP promoter in newborn Gaa-/- mice (AAV dose: $2 \times 10^{13}$ vg/kg). Top panel: Western blot analysis of triceps with anti-GAA antibody 4 months post-treatment. Anti-GAPDH antibodies were used as loading control; rhGAA: recombinant human GAA used as positive control; Ctrl: tissues from untreated Gaa-/- mice used as negative control; the molecular weight marker (kDa) is depicted on the left. Bottom panel: Quantification of the lysosomal GAA band is shown. The number of mice/group is depicted. The GAA band intensity was normalized by the intensity of the GAPDH band used as loading control. Statistical analyses: One-way ANOVA with Tukey post-hoc. Gaa+/+: wild type unaffected littermate mice; Ctrl: untreated Gaa-/- mice. *p<0.05, p<0.01, *p<0.001, ****p<0.0001.

Figure 15:
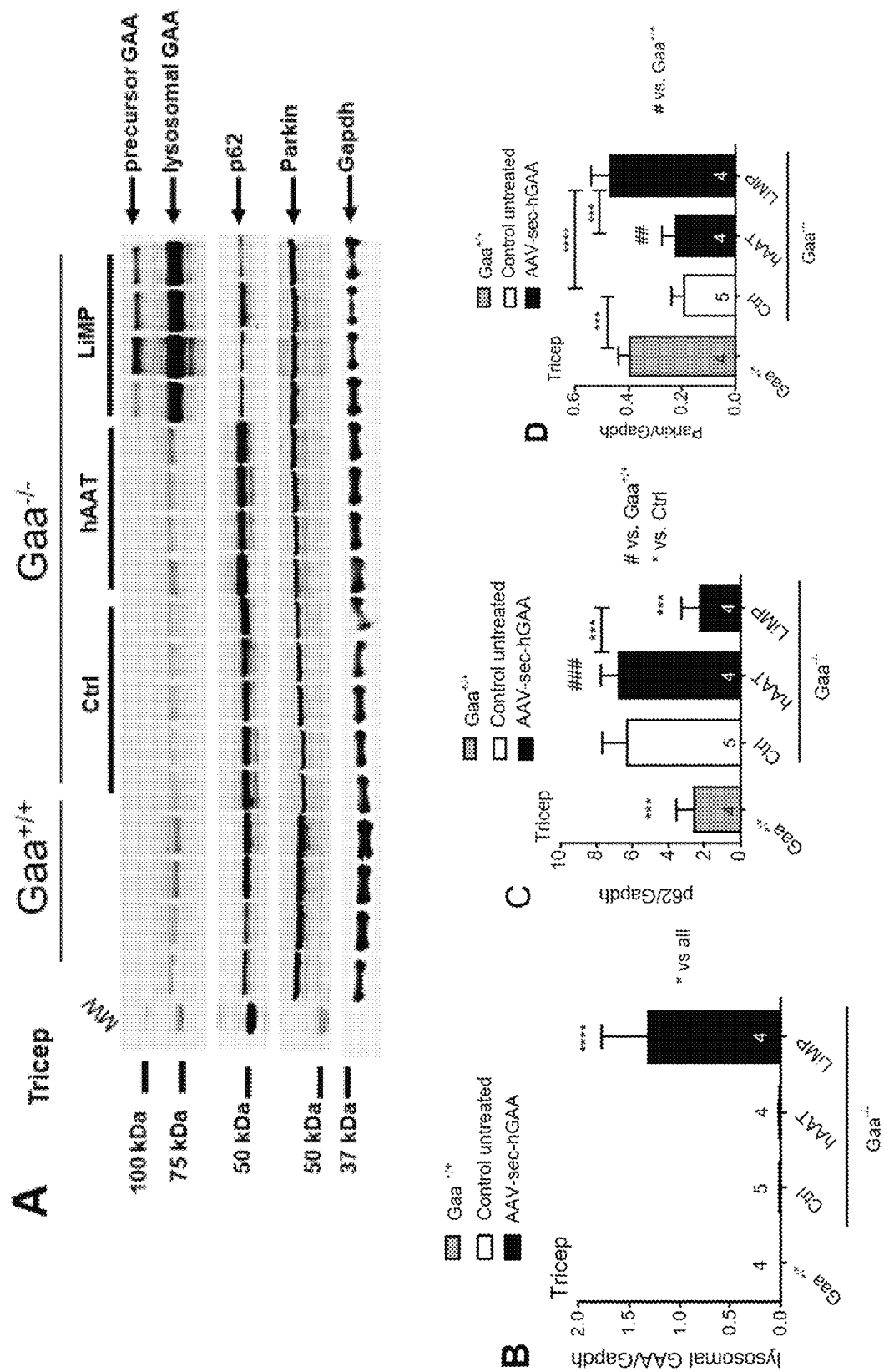

FIG. 15. Analyses of GAA, p62 and parkin protein amount in muscle upon AAV gene therapy with the hybrid liver promoters LiMP in Gaa-/- mice treated as neonates.

Analysis of GAA, p62 and parkin protein in triceps, 4 months following intravenous injection of an AAV9 vector encoding for a highly secretable GAA protein (sec-hGAA) under the control of the liver-specific (hAAT) or our newly generated hybrid liver-muscle LiMP in newborn Gaa-/- mice (AAV dose: $2 \times 10^{13}$ vg/kg). Top panel: Western blot analysis of triceps with anti-GAA, anti-p62, anti-parkin antibodies 4 months post-treatment. Anti-GAPDH antibodies were used as loading control; Ctrl: tissues from untreated Gaa−/− mice used as negative control; the molecular weight marker (kDa) is depicted on the left. Bottom panel: Quantification of the lysosomal GAA band, p62 and parkin bands are shown. The number of mice/group is depicted. The band intensity was normalized by the intensity of the GAPDH band used as loading control. Statistical analyses: One-way ANOVA with Tukey post-hoc. Gaa+/+: wild type unaffected littermate mice; Ctrl: untreated Gaa−/− mice. *$p<0.05$, $p<0.01$, *$p<0.001$, ****$p<0.0001$, ##$p<0.01$, ###$p<0.001$.

Figure 16:

FIG. 16. Analysis of vector genome copy number (VGCN) in liver and triceps of Gaa−/− mice treated as neonates.

Analysis of vector genome copy number (VGCN) in liver (A) and triceps (B) of mice depicted in FIGS. 14 and 15, 4 months following intravenous injection of an AAV9 vector encoding for a highly secretable GAA protein (sec-hGAA) under the control of the ubiquitous (CAG), liver-specific (hAAT) or our newly generated hybrid liver-muscle LiMP or liver-neuron LiNeuP promoters in newborn Gaa−/− mice (AAV dose: $2\times10^{13}$ vg/kg). The number of mice/group is depicted. Statistical analyses: One-way ANOVA with Tukey post-hoc. Gaa+/+: wild type unaffected littermate mice; Ctrl: untreated Gaa−/− mice. *$p<0.05$, $p<0.01$, *$p<0.001$, ****$p<0.0001$.

Figure 17:
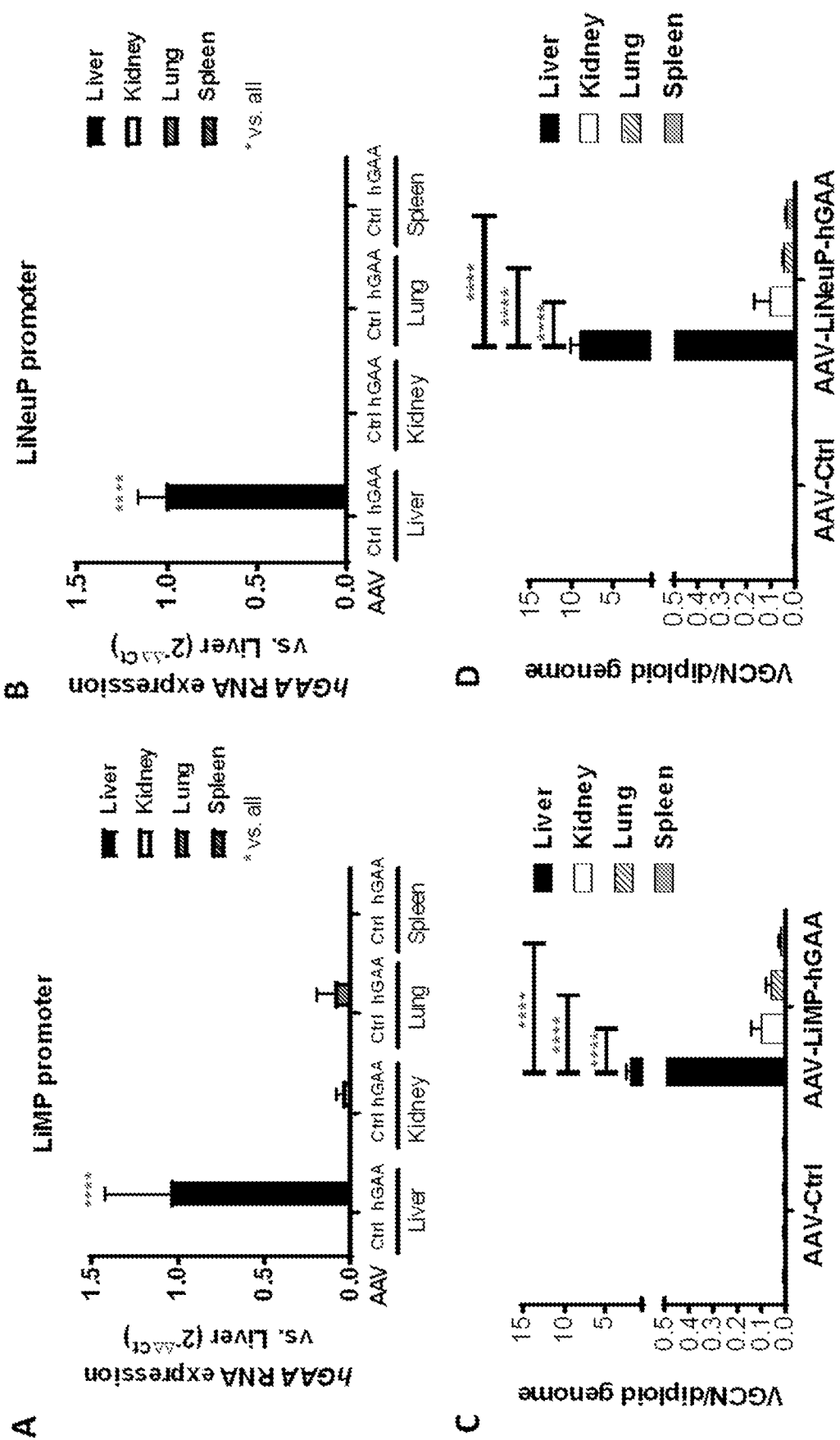

FIG. 17. Analysis of GAA transgene mRNA expression in Gaa−/− mice treated systemically with AAV9 vectors.

(A-B) Relative expression (fold change) of the hGAA transgene mRNA in tissues from Gaa−/− mice following intravenous injection of AAV9-hGAA vectors (native hGAA, dose: $2\times10^{12}$ vg/kg) harboring the indicated promoters; n=3 mice/cohort. An AAV9 vector encoding for luciferase was used as negative control (Ctrl). The fold change transgene mRNA expression is depicted in comparison to liver as control target tissue. (C-D) VGCN in tissues depicted in panel A-B. Data are depicted as average±SD. Statistical analysis: (A-D) Two-way ANOVA (tissue, vector) with Tukey posthoc. *$p<0.05$, $p<0.01$, *$p<0.001$, ****$p<0.0001$.

Figure 18:
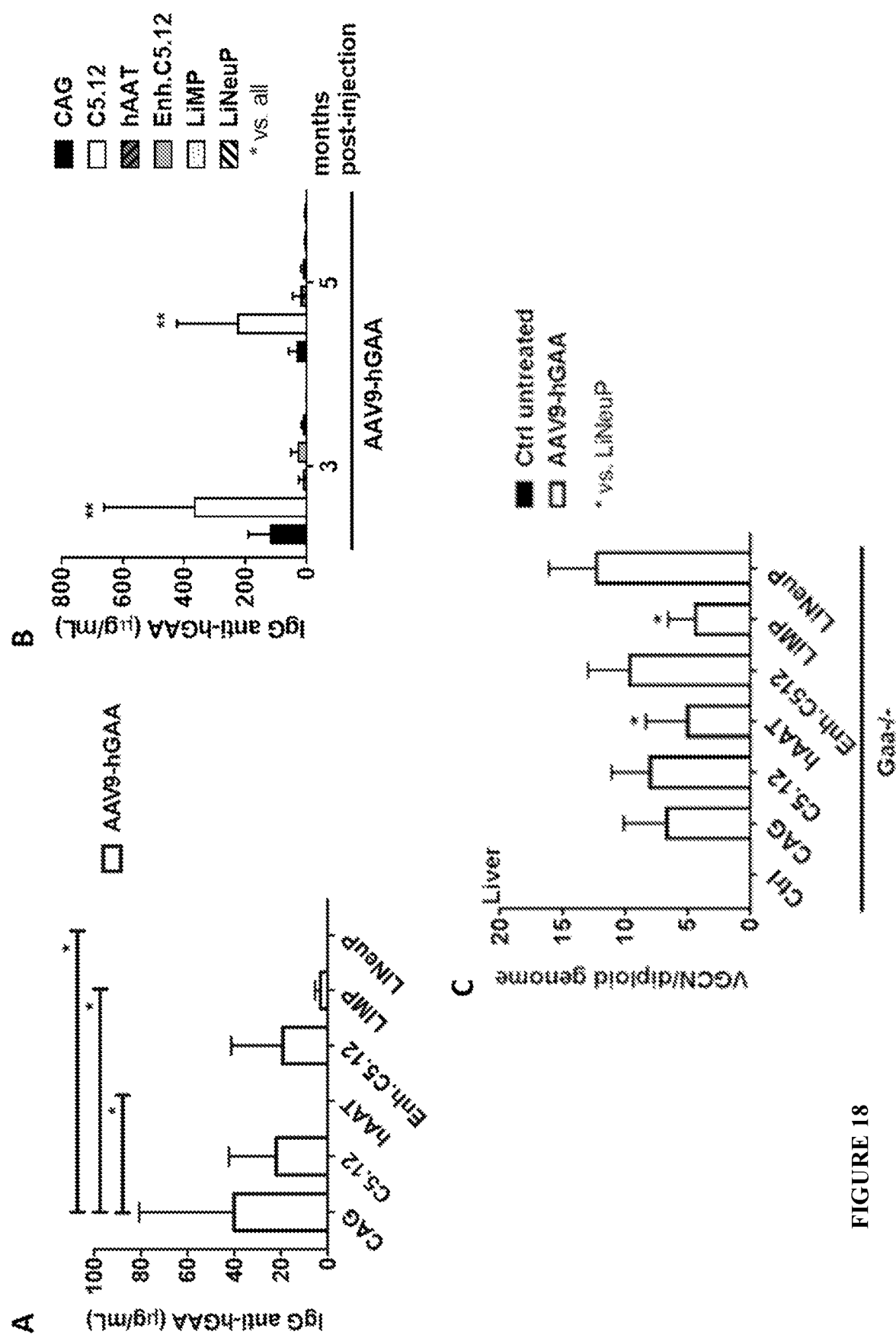

FIG. 18. Anti-hGAA humoral immune responses in adult Gaa−/− mice following AAV gene transfer of hGAA using hybrid promoters.

Analysis of anti-hGAA antibodies (Immunoglobulin G: IgG) in Gaa−/− mice at 1.5 (A), 3 and 5 (B) months and liver vector genome copy number (C) following intravenous injection of AAV9 vectors (dose: $2\times10^{12}$ vg/kg) harboring a native codon optimized human GAA (hGAA) transgene under the control of the hybrid liver-muscle (Enh.C5.12 and LiMP) and liver-neuron (LiNeuP) promoters, or the ubiquitous (CAG), hepatocyte-specific (hAAT) and muscle-specific (C5.12) promoters, as comparison. Gaa−/− mice were treated at 3 months of age. Data are depicted as average±SD; n=3-5 mice/cohort. Untreated Gaa−/− mice were used as affected controls. Statistical analysis: (A) One-way ANOVA with Tukey posthoc. (B) Two-way ANOVA with Tukey posthoc ($p<0.01$ C5.12 vs. CAG, *$p<0.001$ C5.12 vs. hAAT, Enh.C5.12, LiMP and LiNeuP); (C) One-way ANOVA with Tukey posthoc *$p<0.05$, $p<0.01$, *$p<0.001$.

Figure 19:
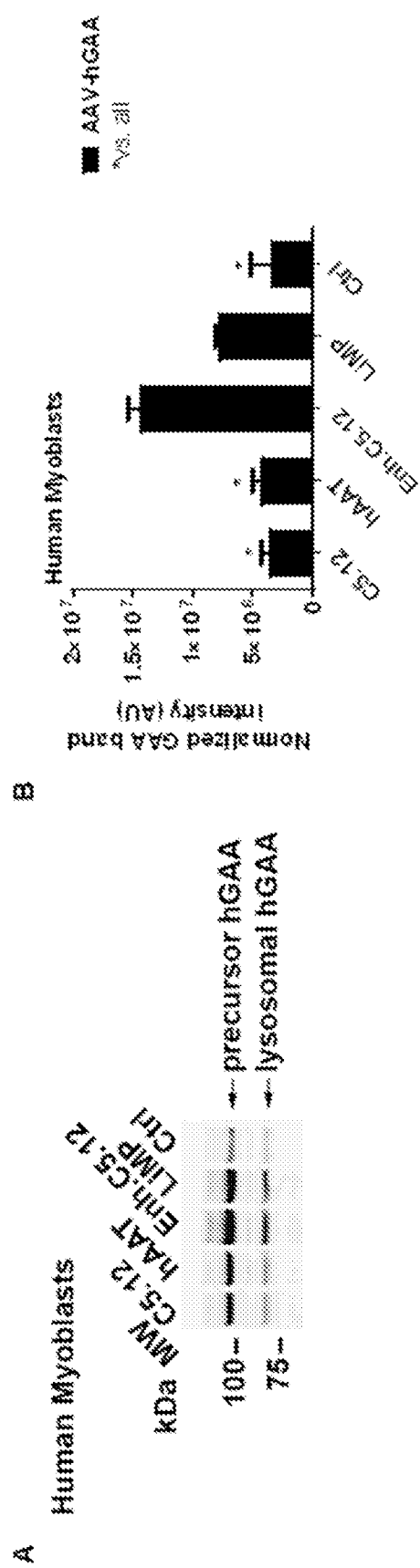

FIG. 19. Activity of the hybrid LiMP promoter in human myoblasts.

(A-B). Analysis of hGAA protein expression upon infection of human myoblasts with AAV9-hGAA vectors (MOI: $2\times10^5$ vg/cell) containing the liver-muscle (Enh.C5.12 and LiMP, FIG. 1A) promoters or the control muscle-specific (C5.12) and hepatocyte-specific (hAAT) promoters (FIG. S1). AAV9 vectors encoding for enhanced green fluorescent protein were used as negative control (Ctrl). (A). Representative Western blot analysis of cell lysates with anti-human GAA antibody. The molecular weight marker (kDa) is depicted. The picture is representative of n=2 independent experiments. (B). Western blot quantification. The GAA band intensity was normalized by the amount of protein lysate loaded. Data are shown as average±SD of n=2 independent experiments. Statistical analysis was performed by One-way ANOVA (vs. Ctrl) with Dunnet's posthoc. *$p<0.05$.

DETAILED DESCRIPTION

Definitions

In the context of the present invention, a "transcription regulatory element" is a DNA sequence able to drive or enhance transgene expression in a tissue or cell. In the context of the present invention, transcription regulatory elements are selected from tissue-selective promoters and tissue-selective enhancers. In a particular embodiment, the transcription regulatory elements are selected from tissue-selective promoters and tissue-selective enhancers of tissue-selective or tissue-specific genes.

In the context of the present invention, the expression "tissue-selective promoters" includes natural or synthetic promoters. In particular, the expression "tissue-selective promoters" also denotes synthetic promoters comprising a tissue-selective promoter and an enhancer having the same tissue-selectivity as the promoter. An illustrative promoter encompassed by this expression is, for example, the fusion of the ApoE enhancer and the hAAT promoter, the fusion of which corresponding to a liver-selective promoter according to the definition provided in this paragraph.

According to the present invention "tissue-selectivity" means that a transcription regulatory element preferentially drives (in case of a promoter) or enhances (in case of an enhancer) expression of a gene operably linked to said transcription regulatory element in a given tissue, or set of tissues, as compared to expression in another tissue(s). This definition of "tissue-selectivity" does not exclude the possibility for a tissue-selective transcription regulatory element (such as a tissue-selective promoter) to leak to some extent. By "leak", "leaking" or declinations thereof, it is meant the possibility for a transcription regulatory element selective of a one tissue to drive or increase expression of a transgene operably linked to said transcription regulatory element into another tissue, although at lower expression levels. For example, a muscle-selective promoter may leak in the liver tissue, meaning that expression drove from this promoter is higher in the muscle tissue than in the liver tissue. Alternatively, the tissue-selective transcription regulatory element may be a "tissue-specific" transcription regulatory element, meaning that this transcription regulatory element not only drives or enhances expression in a given tissue, or set of tissues, in a preferential manner, but also that this regulatory element does not, or does only marginally, drive or enhance expression in other tissues.

In the context of the present invention, a "hybrid transcription regulatory element" denotes a DNA sequence able to drive a transgene expression in two or more tissues or set of tissues in a tissue-dependent manner. According to the present invention, and as is explained in more details below, each transcription regulatory element is tissue- or cell-selective, i.e. it may drive expression of a transgene of interest in a tissue-selective manner, thereby preferentially restricting the expression of the transgene into tissues where the transgene product is desired.

In the context of the present invention, a "tolerogenic tissue", is a tissue, such as liver, from which immune tolerance against a transgene may be achieved when said transgene is expressed from said tissue.

The term "immune tolerance" refers to a state of unresponsiveness to a specific antigen or group of antigens to which a subject would normally be responsive. Alternatively, immune tolerance can be defined as a state in which the immune system actively mediates suppression of immune responses to an antigen, for example via regulatory T cells. In the context of the present invention, the "antigen" or "group of antigens" against which immune tolerance is sought to be achieved is the transgene of interest.

According to the present invention, a "transgene of interest" refers to a polynucleotide sequence that encodes for a RNA or protein product and that may be introduced into a cell for a sought purpose, and is capable of being expressed under appropriate conditions. A transgene of interest may encode a product of interest, for example a therapeutic or diagnostic product of interest. A "therapeutic transgene" is selected and used to lead to a desired therapeutic outcome, in particular for achieving expression of said therapeutic transgene into a cell, tissue or organ into which expression of said therapeutic transgene is needed. Therapy may be achieved by a number of ways, including by expressing a protein into a cell that does not express said protein, by expressing a protein into a cell that expresses a mutated version of the protein, by expressing a protein that is toxic to the target cell into which it is expressed (strategy used, for example, for killing unwanted cells such as cancer cells), by expressing an antisense RNA to induce gene repression or exon skipping, or by expressing a silencing RNA such as a shRNA whose purpose is to suppress the expression of a protein.

According to the present invention, the term "treatment" includes curative, alleviation or prophylactic effects. Accordingly, a therapeutic and prophylactic treatment includes amelioration of the symptoms of a disorder or preventing or otherwise reducing the risk of developing a particular disorder. A treatment may be administered to delay, slow or reverse the progression of a disease and/or of one or more of its symptoms. The term "prophylactic" may be considered as reducing the severity or the onset of a particular condition. "Prophylactic" also includes preventing reoccurrence of a particular condition in a patient previously diagnosed with the condition. "Therapeutic" may also refer to the reduction of the severity of an existing condition. The term "treatment" is used herein to refer to any regimen that can benefit an animal, in particular a mammal, more particularly a human subject. In a particular embodiment, said mammal may be an infant or adult subject, such as a human infant or human adult.

By "cell of therapeutic interest" or "tissue of therapeutic interest", it is meant herein a main cell or tissue where expression of the therapeutic transgene will be useful for the treatment of a disorder. Such tissues of therapeutic interest include without limitation, muscles (such as skeletal, diaphragm, and cardiac muscles), the nervous system (such as the brain or the spinal cord), kidney, lung and intestine. Cells of therapeutic interest include, without limitation, hepatocytes, cardiomyocytes, myofibers, neurons (e.g. motor neurons, sensor neurons), glial cells and endothelial cells.

Hybrid Transcription Regulatory Elements

The present inventors have designed novel multi-tissue-selective transcription regulatory elements, also referred to herein as "hybrid transcription regulatory elements", for increasing gene therapy efficacy. In particular, the novel multi-tissue-selective transcription regulatory elements may combine different tissue-selective enhancers and/or tissue-selective promoters.

The nucleic acid sequence of the invention relates to such a hybrid transcription regulatory element. The nucleic acid molecule of the invention comprises (i) a first transcription regulatory element capable of driving or enhancing tissue-selective expression in a first tissue (i.e. a first tissue-selective transcription regulatory element); and (ii) a second transcription regulatory element capable of driving or enhancing tissue-selective expression in a second tissue (i.e. a second tissue-selective transcription regulatory element), and wherein the first and second transcription regulatory elements are fused together. In the present invention, the first and second transcription regulatory elements have a different tissue-selectivity, and at least one of the first and second transcription regulatory elements is a promoter.

Selection of the transcription regulatory elements to be included in the nucleic acid sequence of the invention will depend on the specific aim of the nucleic acid sequence and the transgene of interest operably linked to it. In particular, in case of the use of the nucleic acid sequence of the invention in a vector for gene therapy, it will depend on the disease or disorder the practitioner aims to treat. Depending on the case, the transcription regulatory elements may be selected as being capable of driving expression in a number of tissues or cells, such as in the liver, muscles, in the central nervous system such as in the brain or the spinal cord, for example in neurons (e.g. in motor neurons, sensory neurons or interneurons) or glial cells, in the peripheral nervous system (PNS), in the kidney, in the eye, or in the lung. Other tissues or cells of interest may include circulating cells such as cells of the immune system, for example in B cells, T cells or macrophages; haematopoietic cells; or endothelial cells.

In a particular embodiment, expression is sought in the liver, for example, for inducing immune tolerance to a transgene of interest, but not only.

In another particular embodiment, expression is sought in muscles.

In still another embodiment, expression is sought in neurons.

In a further particular embodiment, transcription regulatory elements are selected for expression into the liver and the muscles.

In another embodiment, transcription regulatory elements are selected for expression into the liver and neurons.

In another embodiment, transcription regulatory elements are selected for expression into the muscles and neurons.

In a further embodiment, transcription regulatory elements are selected for expression into the liver, muscles and neurons.

As mentioned in the definitions above, the transcription regulatory element(s) may be tissue-selective enhancer(s) or tissue-selective promoter(s).

The first tissue-selective transcription regulatory element drives/enhances expression of a transgene into a first cell or tissue of interest, such as a first cell or tissue of therapeutic interest. In a particular embodiment, the first tissue-selective transcription regulatory element drives/enhances expression of a transgene into the liver. In a particular embodiment, expression into the liver is sought for the tolerogenic properties of this tissue. Therefore, in this particular embodiment, the first transcription regulatory element is a liver-selective transcription regulatory element. Composite or artificial liver promoters are derived by combining promoter regions of liver-expressed genes. Illustrative liver-selective transcription regulatory elements include, without limitation, the Apolipoprotein E (ApoE-enhancer sequence shown in SEQ ID NO:4) and A-I (Apo A-I) enhancers (Van Linthout S, Hum Gene Ther. 2002 May 1; 13 (7): 829-40), antitrypsin promoters-for example the alpha-1 antitrypsin promoter (hAAT-shown in SEQ ID NO: 2), the transthyretin promoter (TTR), the albumin promoter (Alb), the thyroxine-binding globulin (TBG) promoter, the LSP promoter (comprising a thyroid hormone-binding globulin promoter sequence, two copies of an alpha1-microglobulin/bikunin enhancer sequence, and a leader sequence—Ill, Charles R., et al., 1997). Optimization of the human factor VIII complementary DNA expression plasmid for gene therapy of hemophilia A. Blood Coag. Fibrinol. 8: S23-S30.), etc. Other useful liver-selective promoters are known in the art, for example those listed in the Liver Specific Gene Promoter Database compiled by the Cold Spring Harbor Laboratory (rulai.cshl.edu/LSPD/). Other transcription regulatory elements that are, in particular, able to enhance liver-selective expression of genes, are those disclosed in WO2009130208. In a particular embodiment, the liver-selective transcription regulatory element comprises the combination of the ApoE enhancer with a liver-selective promoter selected in the group consisting of antitrypsin promoters—for example the alpha-1 antitrypsin promoter (hAAT—shown in SEQ ID NO:2), the transthyretin promoter (TTR), the albumin promoter (Alb), the thyroxine-binding globulin (TBG) promoter, the LSP promoter defined above, and any other liver-selective promoter such as those listed in the Liver Specific Gene Promoter Database compiled by the Cold Spring Harbor Laboratory (rulai.cshl.edu/LSPD/). In a particular embodiment, the liver-selective transcription regulatory element for use in the context of the present invention is a liver-selective promoter selected in the group consisting of the alpha-1 antitrypsin promoter (hAAT), a combination of the ApoE enhancer and the hAAT promoter, the transthyretin promoter, the albumin promoter, the thyroxine-binding globulin (TBG) promoter and the LSP promoter. A particular liver-selective transcription regulatory element for use in the context of the invention is the combination of the ApoE enhancer (ApoE) and the hAAT promoter.

The second tissue-selective transcription regulatory element drives or enhances expression of a transgene into a second cell or tissue of interest. In particular, the second tissue-selective transcription regulatory element can drives expression of a transgene into a second cell or tissue of interest.

In a particular embodiment, the second tissue-selective transcription regulatory element is a muscle-selective promoter, eventually coupled with a muscle-selective enhancer. In another particular embodiment, the second tissue-selective transcription regulatory element is a muscle-selective enhancer.

One example of a suitable muscle-selective promoter includes a muscle creatine kinase (MCK) promoter. Non-limiting examples of suitable muscle creatine kinase promoters are human muscle creatine kinase promoters and truncated murine muscle creatine kinase [(tMCK) promoters] (Wang B et al, Construction and analysis of compact muscle-selective promoters for AAV vectors. Gene Ther. 2008 November; 15(22):1489-99) (representative GenBank Accession No. AF188002). Human muscle creatine kinase has the Gene ID No. 1158 (representative GenBank Accession No. NC_000019.9, accessed on Dec. 26, 2012). Other examples of muscle-selective promoters include a synthetic promoter C5.12 (spC5.12, alternatively referred to herein as "C5.12"), such as the spC5.12 shown in SEQ ID NO:1 or the spC5.12 promoter (disclosed in Wang et al., Gene Therapy volume 15, pages 1489-1499 (2008)), the MHCK7 promoter (Salva et al. Mol Ther. 2007 February; 15(2):320-9), myosin light chain (MLC) promoters, for example MLC2 (Gene ID No. 4633; representative GenBank Accession No. NG_007554.1, accessed on Dec. 26, 2012); myosin heavy chain (MHC) promoters, for example alpha-MHC (Gene ID No. 4624; representative GenBank Accession No. NG_023444.1, accessed on Dec. 26, 2012); desmin promoters (Gene ID No. 1674; representative GenBank Accession No. NG_008043.1, accessed on Dec. 26, 2012); cardiac troponin C promoters (Gene ID No. 7134; representative GenBank Accession No. NG_008963.1, accessed on Dec. 26, 2012); troponin I promoters (Gene ID Nos. 7135, 7136, and 7137; representative GenBank Accession Nos. NG_016649.1, NG_011621.1, and NG_007866.2, accessed on Dec. 26, 2012); myoD gene family promoters (Weintraub et al., Science, 251, 761 (1991); Gene ID No. 4654; representative GenBank Accession No. NM_002478, accessed on Dec. 26, 2012); alpha actin promoters (Gene ID Nos. 58, 59, and 70; representative GenBank Accession Nos. NG_006672.1, NG_011541.1, and NG_007553.1, accessed on Dec. 26, 2012); beta actin promoters (Gene ID No. 60; representative GenBank Accession No. NG_007992.1, accessed on Dec. 26, 2012); gamma actin promoters (Gene ID No. 71 and 72; representative GenBank Accession No. NG_011433.1 and NM_001199893, accessed on Dec. 26, 2012); muscle-selective promoters residing within intron 1 of the ocular form of Pitx3 (Gene ID No. 5309) (Coulon et al; the muscle-selective promoter corresponds to residues 11219-11527 of representative GenBank Accession No. NG_008147, accessed on Dec. 26, 2012); and the promoters described in US Patent Publication US 2003/0157064, and CK6 promoters (Wang et al 2008 doi: 10.1038/gt.2008.104). In another particular embodiment, the muscle-selective promoter is the E-Syn promoter (sequence shown in SEQ ID NO:13) described in Wang et al., Gene Therapy volume 15, pages 1489-1499 (2008), comprising the combination of a MCK-derived enhancer and of the spC5.12 promoter. In a particular embodiment of the invention, the muscle-selective promoter is selected in the group consisting of a spC5.12 promoter, the MHCK7 promoter, the E-syn promoter, a muscle creatine kinase myosin light chain (MLC) promoter, a myosin heavy chain (MHC) promoter, a cardiac troponin C promoter, a troponin I promoter, a myoD gene family promoter, an alpha actin promoter, an beta actin promoter, an gamma actin promoter, a muscle-selective promoter residing within intron 1 of the ocular form of Pitx3 and a CK6 promoter. In a particular embodiment, the muscle-selective promoter is selected in the group consisting of the spC5.12, desmin and MCK promoters. In a further embodiment, the muscle-selective promoter is selected in the group consisting of the spC5.12 and MCK promoters. In a particular embodiment, the muscle-selective promoter is the spC5.12 promoter. In a specific embodiment, the muscle-selective promoter is not the desmin promoter.

Transcription regulatory elements that are, in particular, able to enhance muscle-selective expression of genes, in particular expression in cardiac muscle and/or skeletal muscle, are those disclosed in WO2015110449. Particular examples of nucleic acid transcription regulatory elements that comprise an artificial sequence include the transcription regulatory elements that are obtained by rearranging the transcription factor binding sites (TFBS) that are present in the sequences disclosed in WO2015110449. Said rearrangement may encompass changing the order of the TFBSs and/or changing the position of one or more TFBSs relative to the other TFBSs and/or changing the copy number of one or more of the TFBSs. For example, a nucleic acid transcription regulatory element for enhancing muscle-selective gene expression, in particular cardiac and skeletal muscle-selective gene expression, may comprise binding sites for E2A, HNH 1, NF1, C/EBP, LRF, MyoD, and SREBP; or for E2A, NF1, p53, C/EBP, LRF, and SREBP; or for E2A, HNH 1, HNF3a, HNF3b, NF1, C/EBP, LRF, MyoD, and SREBP; or E2A, HNF3a, NF1, C/EBP, LRF, MyoD, and SREBP; or for E2A, HNF3a, NF1, CEBP, LRF, MyoD, and SREBP; or for HNF4, NF1, RSRFC4, C/EBP, LRF, and MyoD, or NF1, PPAR, p53, C/EBP, LRF, and MyoD. In further examples, these nucleic acid transcription regulatory elements comprise at least two, such as 2, 3, 4, or more copies of one or more of the TFBSs recited before.

In still another particular embodiment, the second tissue-selective transcription regulatory element is a neuron-selective promoter, eventually coupled with a neuron-selective enhancer. In another particular embodiment, the second tissue-selective transcription regulatory element is a neuron-selective enhancer.

Neuron-selective promoters include, but are not limited to the following: synapsin-1 (Syn) promoter (shown in SEQ ID NO:3), neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al. Neuron, 15:373-84 (1995)), among others which will be apparent to the skilled artisan. In a particular embodiment, the neuron-selective promoter is the Syn promoter. Other neuron-selective promoters include, without limitation: synapsin-2 promoter, tyrosine hydroxylase promoter, dopamine β-hydroxylase promoter, hypoxanthine phosphoribosyltransferase promoter, low affinity NGF receptor promoter, and choline acetyl transferase promoter (Bejanin et al., 1992; Carroll et al., 1995; Chin and Greengard, 1994; Foss-Petter et al., 1990; Harrington et al., 1987; Mercer et al., 1991; Patei et al., 1986). Representative promoters selective for the motor neurons include, without limitation, the promoter of the Calcitonin Gene-Related Peptide (CGRP), a known motor neuron-derived factor. Other promoters functional in motor neurons include the promoters of Choline Acetyl Transferase (ChAT), Neuron Specific Enolase (NSE), Synapsin and Hb9. Other neuron-selective promoters useful in the present invention include, without limitation: GFAP (for astrocytes), Calbindin 2 (for interneurons), Mnx1 (motorneurons), Nestin (neurons), Parvalbumin, Somatostation and Plp1 (oligodendrocytes and Schwann cells).

CRMs useful in the practice of the present invention include those described in Rincon et al., Mol Ther. 2015 January; 23(1):43-52, Chuah et al., Mol Ther. 2014 September; 22(9):1605-13 or Nair et al., Blood. 2014 May 15; 123(20):3195-9.

In a further embodiment, the nucleic acid sequence of the invention comprises more than two tissue-selective transcription regulatory elements, such as three, four or more than four tissue-selective transcription regulatory elements. The design of the nucleic acid of the invention will depend on the specific disorder which is sought to be treated, for example if the disorder is a multi-systemic disease whose treatment would benefit from the expression of the therapeutic transgene in more than one tissue. For example, the nucleic acid sequence of the present invention may comprise a first tissue-selective transcription regulatory element (such as a promoter) capable of driving or enhancing expression of a transgene into a tolerogenic tissue, such as in the liver, a second tissue-selective transcription regulatory element (such as a promoter), and a third tissue-selective transcription regulatory element (such as a promoter), wherein the first, second and third tissue-selective transcription regulatory elements are capable of driving expression of a transgene in different tissues. For example, the first tissue-selective transcription regulatory element may be a liver-selective promoter, the second tissue-selective transcription regulatory element may be a muscle-selective promoter and the third tissue-selective transcription regulatory element may be a neuron-selective promoter. Alternatively, both the second tissue-selective transcription regulatory element and the third tissue-selective transcription regulatory element may have the same tissue-selectivity, which is different from the tissue-selectivity of the first transcription regulatory element, to further increase the expression of the therapeutic transgene in the tissue of interest.

The order of the first, second, and further tissue-selective transcription regulatory elements (such as first, second and further tissue-selective promoters) respectively one to another may vary. In a particular embodiment, the first tissue-selective transcription regulatory element is located 5' or 3' of the second tissue-selective transcription regulatory element, in particular 5' of the second tissue-selective transcription regulatory element. In a particular embodiment, wherein the first transcription regulatory element is a liver-selective promoter, said first transcription regulatory element is located 5' in relation to any other transcription regulatory element introduced in the nucleic acid molecule of the invention. For example, the nucleic acid molecule of the invention may comprise, in this order from 5' to 3':

(i)—a liver-selective promoter; and
any other transcription regulatory element with a tissue selectivity different from liver; or
(ii)—a liver-selective promoter; and
a muscle-selective transcription regulatory element, such as a muscle-selective promoter; or
(iii)—a liver-selective promoter; and
a neuron-selective transcription regulatory element, such as a neuron-selective promoter; or
(iv)—a liver-selective promoter;
a muscle-selective transcription regulatory element, such as a muscle-selective promoter; and
a neuron-selective transcription regulatory element, such as a neuron-selective promoter; or
(v)—a liver-selective promoter;
a neuron-selective transcription regulatory element, such as a neuron-selective promoter; and
a muscle-selective transcription regulatory element, such as a muscle-selective promoter.

In the context of the present invention, the transcription regulatory element introduced into the nucleic acid molecule of the invention may be either fused directly or linked via a linker. For example, in case of a design with two different promoters, a direct fusion means that the first nucleotide of the second promoter immediately follows the last nucleotide of the first promoter. In case of a link via a linker, a nucleotide sequence is present between the last nucleotide of the first promoter and the first nucleotide of the second promoter. For example, the length of the linker may be comprised between 1 and 50 nucleotides, such as from 1 to 40 nucleotides, such as from 1 to 30 nucleotides, such as from 1 to 20 nucleotides, such as from 1 to 10 nucleotides.

In a particular embodiment, the nucleic acid sequence of the invention comprises, in particular in this order from 5' to 3':
- a liver-selective transcription regulatory element; and
- a muscle-selective and/or neuron-selective transcription regulatory element, in particular a muscle-selective or neuron-selective transcription regulatory element.

In a further particular embodiment, the nucleic acid sequence of the invention comprises, in particular in this order from 5' to 3':
- the ApoE enhancer; and
- a spC5.12 promoter.

In a variant of this embodiment, the nucleic acid sequence of the invention comprises a combination of SEQ ID NO:4 and SEQ ID NO:1, such as the sequence shown in SEQ ID NO:5.

In another particular embodiment, the nucleic acid sequence of the invention comprises, in particular in this order from 5' to 3':
- a transcription regulatory element, in particular a promoter, capable of driving/enhancing expression of a transgene into a tolerogenic tissue; and
- a muscle-selective and/or neuron-selective transcription regulatory element, in particular a promoter, furthermore a muscle-selective or neuron-selective promoter.

In a further particular embodiment, the nucleic acid sequence of the invention comprises, in particular in this order from 5' to 3':
- a liver-selective promoter; and
- a muscle-selective and/or or neuron-selective promoter, in particular a muscle-selective or neuron-selective promoter.

In an even further particular embodiment, the nucleic acid sequence of the invention comprises, in particular in this order from 5' to 3':
- the hAAT promoter; and
- a spC5.12 promoter.

In a particular variant of this embodiment, the nucleic acid sequence of the invention comprises a combination of SEQ ID NO:2 and SEQ ID NO:1.

In another further particular embodiment, the nucleic acid sequence of the invention comprises, in particular in this order from 5' to 3':
- the ApoE enhancer/hAAT promoter; and
- a spC5.12 promoter.

In a particular variant of this embodiment, the nucleic acid sequence of the invention comprises a combination of SEQ ID NO:4, SEQ ID NO:2 and SEQ ID NO:1, such as the sequence shown in SEQ ID NO:6.

In another further particular embodiment, the nucleic acid sequence of the invention comprises, in particular in this order from 5' to 3':
- the hAAT promoter; and
- the Syn promoter.

In a particular variant of this embodiment, the nucleic acid sequence of the invention comprises a combination of SEQ ID NO:2 and SEQ ID NO:3.

In a further particular embodiment, the nucleic acid sequence of the invention comprises, in particular in this order from 5' to 3':
- the ApoE enhancer; and
- the Syn promoter.

In a variant of this embodiment, the nucleic acid sequence of the invention comprises a combination of SEQ ID NO:4 and SEQ ID NO:3.

In another further particular embodiment, the nucleic acid sequence of the invention comprises, in particular in this order from 5' to 3':
- the ApoE enhancer/hAAT promoter; and
- the Syn promoter.

In a particular variant of this embodiment, the nucleic acid sequence of the invention comprises a combination of SEQ ID NO:4, SEQ ID NO:2 and SEQ ID NO:3, such as the sequence shown in SEQ ID NO:7.

In another particular embodiment, the nucleic acid sequence of the invention comprises, in particular in this order from 5' to 3':
- the hAAT promoter;
- a spC5.12 promoter; and
- the Syn promoter.

In a particular variant of this embodiment, the nucleic acid sequence of the invention comprises a combination of SEQ ID NO:2, SEQ ID NO:1 and SEQ ID NO:3.

In another particular embodiment, the nucleic acid sequence of the invention comprises, in particular in this order from 5' to 3':
- the hAAT promoter;
- the Syn promoter; and
- a spC5.12 promoter.

In a particular variant of this embodiment, the nucleic acid sequence of the invention comprises a combination of SEQ ID NO:2, SEQ ID NO:3 and SEQ ID NO:1.

In another particular embodiment, the nucleic acid sequence of the invention comprises, in particular in this order from 5' to 3':
- the ApoE enhancer/hAAT promoter;
- the spC5.12 promoter; and
- the Syn promoter.

In a particular variant of this embodiment, the nucleic acid sequence of the invention comprises a combination of SEQ ID NO:4, SEQ ID NO:2, SEQ ID NO:1 and SEQ ID NO:3.

In a further particular embodiment, the nucleic acid sequence of the invention comprises, in particular in this order from 5' to 3':
- the ApoE enhancer/hAAT promoter;
- the Syn promoter; and
- a spC5.12 promoter.

In a particular variant of this embodiment, the nucleic acid sequence of the invention comprises a combination of SEQ ID NO:4, SEQ ID NO:2, SEQ ID NO:3 and SEQ ID NO:1.

In another particular embodiment, the nucleic acid sequence of the invention comprises, in particular in this order from 5' to 3':
- a spC5.12 promoter; and
- the Syn promoter.

In a further particular embodiment, the nucleic acid sequence of the invention comprises, in particular in this order from 5' to 3':
- the MHCK7 promoter; and
- the Syn promoter.

In yet another particular embodiment, the nucleic acid sequence of the invention comprises, in particular in this order from 5' to 3':
- the CK promoter; and
- the Syn promoter.

Expression Cassette

The nucleic acid sequence of the invention may be introduced into an expression cassette, designed for providing the expression of a transgene of interest into a tissue of interest.

The expression cassette of the invention thus includes the nucleic acid sequence described above, and a transgene of interest.

The expression cassette may comprise at least one further regulatory sequence capable of further controlling the expression of the therapeutic transgene of interest by decreasing or suppressing its expression in certain tissues that are not of interest, of by stabilizing the mRNA coding for the protein of interest, such as a therapeutic protein, encoded by the transgene of interest. These sequences include, for example, silencers (such as tissue-specific silencers), microRNA target sequences, introns and polyadenylation signals.

In another particular embodiment, the therapeutic transgene may be preceded by an intron, in particular an intron placed between the hybrid promoter of the invention and the therapeutic transgene. An intron may be introduced to increase mRNA stability and the production of the protein of interest, such as a therapeutic protein of interest. In a further embodiment, the intron is a human beta globin b2 (or HBB2) intron, a coagulation factor IX (FIX) intron, a SV40 intron or a chicken beta-globin intron. In another further embodiment, the intron is a modified intron (in particular a modified HBB2 or FIX intron) designed to decrease the number of, or even totally remove, alternative open reading frames (ARFs) found in said intron. The inventors have previously shown in WO2015/162302 that such a modified intron, in particular a modified HBB2 or FIX intron, has advantageous properties and can significantly improve the expression of a transgene.

In a particular embodiment, the expression cassette of the invention comprises, in this order from 5' to 3':
  the nucleic acid sequence of the invention;
  the transgene of interest; and
  a polyadenylation signal.

In a further particular embodiment, the expression cassette of the invention comprises, in this order from 5' to 3':
  the nucleic acid sequence of the invention;
  an intron, such as an HBB2 or SV40 intron;
  the transgene of interest; and
  a polyadenylation signal.

Vectors, Cells and Pharmaceutical Compositions

The expression cassette of the invention may be introduced into a vector. Thus, the invention also relates to a vector comprising the expression cassette described above. The vector used in the present invention is a vector suitable for RNA/protein expression, and in particular suitable for gene therapy.

In one embodiment, the vector is a plasmid vector.

In another embodiment, the vector is a non-viral vector, such as a nanoparticle, a lipid nanoparticle (LNP) or a liposome, containing the expression cassette of the invention.

In another embodiment, the vector is a system based on transposons, allowing integration of the expression cassette of the invention in the genome of the target cell, such as the hyperactive Sleeping Beauty (SB100X) transposon system (Mates et al. 2009).

In another embodiment, the vector is a viral vector suitable for gene therapy, targeting any cell or tissue of interest such as the tolerogenic tissue described above (for example the liver tissue or cells) and the tissue(s) of therapeutic interest such as muscles or CNS cells (such as neurons, or other spinal cord or brain cells). In this case, the further sequences are added to the expression cassette of the invention, suitable for producing an efficient viral vector, as is well known in the art. In a particular embodiment, the viral vector is derived from an integrating virus. In particular, the viral vector may be derived from an adenovirus, a retrovirus or a lentivirus (such as an integration-deficient lentivirus). In a particular embodiment, the lentivirus is a pseudotyped lentivirus having an enveloped that enable the targeting of cells/tissues of interest, such as liver and/or muscle cells (as described in patent applications EP17306448.6 and EP17306447.8). In case the viral vector is derived from a retrovirus or lentivirus, the further sequences are retroviral or lentiviral LTR sequences flanking the expression cassette. In another particular embodiment, the viral vector is an AAV vector, such as an AAV vector suitable for transducing a tolerogenic tissue, such as the liver, and another tissue of therapeutic interest. In this embodiment, the further sequences are AAV ITR sequences flanking the expression cassette.

In a preferred embodiment, the vector is an AAV vector. The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter). Therefore, AAV vectors have arisen considerable interest as potential vectors for human gene therapy. Among the favorable properties of the virus are its lack of association with any human disease, its ability to infect both dividing and non-dividing cells, and the wide range of cell lines derived from different tissues that can be infected.

Among the serotypes of AAVs isolated from human or non-human primates (NHP) and well characterized, human serotype 2 is the first AAV that was developed as a gene transfer vector. Other currently used AAV serotypes include AAV-1, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods.), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -2G9, -10 such as cy10 and -rh10, -rh74, -dj, Anc80, LK03, AAV2i8, porcine AAV serotypes such as AAVpo4 and AAVpo6, and tyrosine, lysine and serine capsid mutants of the AAV serotypes, etc. In addition, other non-natural engineered variants and chimeric AAV can also be useful.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

AAV-based recombinant vectors lacking the Rep protein integrate with low efficacy into the host's genome and are mainly present as stable circular episomes that can persist for years in the target cells.

Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

In the context of the present invention, the AAV vector comprises an AAV capsid able to transduce the target cells of interest, i.e. cells of the tolerogenic tissue (for example hepatocytes) and cells of the tissue(s) of therapeutic interest such as muscle cells, CNS cells or cardiac cells.

According to a particular embodiment, the AAV vector is of the AAV-1, -2, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -2G9, -10 such as -cy10 and -rh10, -rh39, -rh43, -rh74, -dj, Anc80, LK03, AAV.PHP, AAV2i8, porcine AAV such as AAVpo4 and AAVpo6, and tyrosine, lysine and serine capsid mutants of AAV serotypes. In a particular embodiment, the AAV vector is of the AAV8, AAV9, AAVrh74 or AAV2i8 serotype (i.e. the AAV vector has a capsid of the AAV8, AAV9, AAVrh74 or AAV2i8 serotype). In a further particular embodiment, the AAV vector is a pseudotyped vector, i.e. its genome and capsid are derived from AAVs of different serotypes. For example, the pseudotyped AAV vector may be a vector whose genome is derived from one of the above mentioned AAV serotypes, and whose capsid is derived from another serotype. For example, the genome of the pseudotyped vector may have a capsid derived from the AAV8, AAV9, AAVrh74 or AAV2i8 serotype, and its genome may be derived from and different serotype. In a particular embodiment, the AAV vector has a capsid of the AAV8, AAV9 or AAVrh74 serotype, in particular of the AAV8 or AAV9 serotype, more particularly of the AAV8 serotype.

In a specific embodiment, wherein the vector is for use in delivering the therapeutic transgene to muscle cells, the AAV vector may be selected, among others, in the group consisting of AAV8, AAV9 and AAVrh74.

In another specific embodiment, wherein the vector is for use in delivering the transgene to liver cells, the AAV vector may be selected, among others, in the group consisting of AAV1, AAV5, AAV8, AAV9, AAVrh10, AAVrh39, AAVrh43, AAVrh74, AAV-LK03, AAV2G9, AAV.PHP, AAV-Anc80 and AAV3B.

In a further specific embodiment, wherein the vector is for use in delivering the transgene to the CNS, the AAV vector may be selected, among others, in the group consisting of AAV9, AAV10 and AAV2G9.

In another embodiment, the capsid is a modified capsid. In the context of the present invention, a "modified capsid" may be a chimeric capsid or capsid comprising one or more variant VP capsid proteins derived from one or more wild-type AAV VP capsid proteins. In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in Shen et al., Molecular Therapy, 2007 and in Tenney et al., Virology, 2014. For example, a chimeric AAV vector can derive from the combination of an AAV8 capsid sequence with a sequence of an AAV serotype different from the AAV8 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in Bartel et al., 2011). In addition, capsid variants may include single amino acid changes such as tyrosine mutants (e.g. as described in Zhong et al., 2008).

In addition, the genome of the AAV vector may either be a single stranded or self-complementary double-stranded genome (McCarty et al., Gene Therapy, 2003). Self-complementary double-stranded AAV vectors are generated by deleting the terminal resolution site from one of the AAV terminal repeats. These modified vectors, whose replicating genome is half the length of the wild type AAV genome have the tendency to package DNA dimers. In a preferred embodiment, the AAV vector implemented in the practice of the present invention has a single stranded genome, and further preferably comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid. As is known in the art, additional suitable sequences may be introduced in the nucleic acid construct of the invention for obtaining a functional viral vector. Suitable sequences include AAV ITRs.

Of course, in designing the nucleic acid sequence of the invention and the expression cassette of the invention one skilled in the art will take care of respecting the size limit of the vector used for delivering said construct to a cell or organ. In particular, in case of the vector being an AAV vector, one skilled in the art knows that a major limitation of AAV vector is its cargo capacity which may vary from one AAV serotype to another but is thought to be limited to around the size of parental viral genome. For example, 5 kb is the maximum size usually thought to be packaged into an AAV8 capsid. (Wu Z. et al., Mol Ther., 2010, 18(1): 80-86; Lai Y. et al., Mol Ther., 2010, 18(1): 75-79; Wang Y. et al., Hum Gene Ther Methods, 2012, 23(4): 225-33). Accordingly, those skilled in the art will take care in practicing the present invention to select the components of the nucleic acid construct of the invention so that the resulting nucleic acid sequence, including sequences coding AAV 5'- and 3'-ITRs to preferably not exceed 110% of the cargo capacity of the AAV vector implemented, in particular to preferably not exceed 5.5 kb.

The invention also relates to an isolated cell, for example a liver, muscle or neuron cell, which is transformed with a nucleic acid sequence of the invention or with the expression cassette of the invention. Cells of the invention may be delivered to the subject in need thereof via injection in the tissue of interest or in the bloodstream of said subject. In a particular embodiment, the invention involves introducing the nucleic acid sequence or the expression cassette of the invention into cells of the subject to be treated, in particular into liver, muscle or neuron cells of the subject to be treated, and administering back to the subject said cells into which the nucleic acid or expression cassette has been introduced.

The present invention also provides a pharmaceutical composition comprising a nucleic acid sequence, a vector or a cell of the invention. Such compositions comprise a therapeutically effective amount of the nucleic acid sequence, vector or cell of the invention, and a pharmaceutically acceptable carrier. The term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject. In a particular embodiment, the nucleic acid sequence, expression cassette, vector or cell of the invention is formulated in a composition comprising phosphate-buffered saline and supplemented with 0.25% human serum albumin. In another particular embodiment, the vector of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous or intramuscular administration, preferably intravenous administration, to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

In an embodiment, the nucleic acid sequence, expression cassette or vector of the invention can be delivered in a vesicle, in particular a liposome. In yet another embodiment, the nucleic acid sequence, expression cassette or the vector of the invention can be delivered in a controlled release system.

Methods of Use of the Vector

Thanks to the multi-selective transcription regulatory elements included in the nucleic acid sequence of the invention, a transgene of interest may be expressed in more than one tissue, without eliciting the concerns raised by ubiquitous promoters. In particular, the nucleic acid sequence of the invention may be used to produce less genotoxic expression cassettes. In particular, the nucleic acid sequence of the invention may advantageously avoid the unwanted upregulation of oncogenes.

The nucleic acid sequence, expression cassette or vector of the present invention may be used for treating a disorder by gene therapy. Likewise, the cell of the invention may be used for treating a disorder by cell therapy.

Accordingly, in one aspect, the invention relates to a nucleic acid sequence, expression cassette, vector, cell or pharmaceutical composition as described above, for use as a medicament.

In another aspect, the invention relates to a nucleic acid sequence, expression cassette, vector, cell or pharmaceutical composition as described above, for use in a method for the treatment of a disorder by gene therapy.

In a further aspect, the invention relates to the use of a nucleic acid sequence, expression cassette, vector, cell or pharmaceutical composition as described above, for the manufacture of a medicament for use in the treatment of a disorder by gene therapy.

In another aspect, the invention relates to a method for the treatment of a disorder by gene therapy, comprising administering a therapeutically effective amount of the nucleic acid sequence, expression cassette, vector, cell or pharmaceutical composition described herein to a subject in need thereof.

The disorder may be any disorder for which expression of a given gene may be desirable into at least two different tissues, in particular the disorders whose treatment may be hampered by an anti-transgene immune-response. The disorder is in particular an inherited or acquired disorder, such as an inherited or acquired neuromuscular disease. Of course, the therapeutic transgene and the promoter driving expression into a tissue of therapeutic interest will be selected in view of the disorder to be treated.

In a particular embodiment, the disorder is a lysosomal storage disease [(LSDs), such as mucopolysaccharidosis type I to VII (MPSI-VII), Sandhoff disease and Tay-Sachs] and the nucleic acid sequence of the invention comprises liver-selective, muscle-selective and/or neuron-selective transcription regulatory elements, such as liver-selective and muscle-selective transcription regulatory elements, liver-selective and neuron-selective transcription regulatory elements, and liver-selective, muscle-selective and neuron-selective transcription regulatory elements.

In a particular embodiment, the disorder is a metabolic disease [such as Maple syrup disease (MSUD), Methylmalonic academia (MMA), glycogenosis type I and III (GSDI and III], Niemann-Pick disease (NPC), Canavan disease, Phenylketonuria (PKU)] and the nucleic acid sequence of the invention comprises liver-selective, muscle-selective and/or neuron-selective transcription regulatory elements, such as liver-selective and muscle-selective transcription regulatory elements, liver-selective and neuron-selective transcription regulatory elements, and liver-selective, muscle-selective and neuron-selective transcription regulatory elements.

In a particular embodiment, the disorder is a neuromuscular disorder. The term "neuromuscular disorder" encompasses diseases and ailments that impair the functioning of the muscles, either directly, being pathologies of the voluntary muscle, or indirectly, being pathologies of nerves or neuromuscular junctions. Illustrative neuromuscular disorders include, without limitation, muscular dystrophies (e.g. myotonic dystrophy (Steinert disease), Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy, motor neuron diseases (e.g. amyotrophic lateral sclerosis (ALS), spinal muscular atrophy (Infantile progressive spinal muscular atrophy (type 1, Werdnig-Hoffmann disease), intermediate spinal muscular atrophy (Type 2), juvenile spinal muscular atrophy (Type 3, Kugelberg-Welander disease), adult spinal muscular atrophy (Type 4)), spinal-bulbar muscular atrophy (Kennedy disease)), inflammatory Myopathies (e.g. polymyositis dermatomyositis, inclusion-body myositis), diseases of neuromuscular junction (e.g. myasthenia gravis, Lambert-Eaton (myasthenic) syndrome, congenital myasthenic syndromes), diseases of peripheral nerve (e.g. Charcot-Marie-Tooth disease, Friedreich's ataxia, Dejerine-Sottas disease), metabolic diseases of muscle (e.g. phosphorylase deficiency (McArdle disease) acid maltase deficiency (Pompe disease) phosphofructokinase deficiency (Tarui disease) debrancher enzyme deficiency (Cori or Forbes disease) mitochondrial myopathy, carnitine deficiency, carnitine palmityl transferase deficiency, phosphogly cerate kinase deficiency, phosphoglycerate mutase deficiency, lactate dehydrogenase deficiency, myoadenylate deaminase deficiency), myopathies due to endocrine abnormalities (e.g. hyperthyroid myopathy, hypothyroid myopathy), and other myopathies (e.g. myotonia congenital, paramyotonia congenital, central core disease, nemaline myopathy, myotubular myopathy, periodic paralysis). In this embodiment, the nucleic acid sequence of the invention comprises liver-selective, muscle-selective and/or neuron-selective transcription regulatory elements, such as liver-selective and muscle-selective transcription regulatory elements, liver-selective and neuron-selective transcription regulatory elements, and liver-selective, muscle-selective and neuron-selective transcription regulatory elements.

In a particular, the disorder is a glycogen storage disease. The expression "glycogen storage disease" denotes a group of inherited metabolic disorders involving enzymes responsible for the synthesis and degradation of glycogen. In a more particular embodiment, the glycogen storage disease may be GSDI (von Gierke's disease), GSDII (Pompe disease), GSDIII (Cori disease), GSDIV, GSDV, GSDVI, GSDVII, GSDVIII or lethal congenital glycogen storage disease of the heart. More particularly, the glycogen storage disease is selected in the group consisting of GSDI, GSDII and GSDIII, even more particularly in the group consisting of GSDII and GSDIII. In an even more particular embodiment, the glycogen storage disease is GSDII. In particular, the nucleic acid molecules of the invention may be useful in gene therapy to treat GAA-deficient conditions, or other conditions associated by accumulation of glycogen such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII. In a further particular embodiment, the disorder is Pompe disease and the therapeutic transgene is a gene encoding an acid alpha-glucosidase (GAA) or a variant thereof. Such variants of GAA are in particular disclosed in applications PCT/2017/072942, PCT/EP2017/072945 and PCT/EP2017/072944, which are incorporated herein by reference in their entirety. In this embodiment, the nucleic acid sequence of the invention comprises liver-selective, muscle-selective and/or neuron-selective transcription regulatory elements, such as liver-selective and muscle-selective transcription regulatory elements, liver-selective and neuron-selective transcription regulatory elements, muscle-selective and neuron-selective transcription regulatory elements, and liver-selective, muscle-selective and neuron-selective transcription regulatory elements. In a particular embodiment, the disorder is infantile-onset Pompe disease (IOPD) or late onset Pompe disease (LOPD). Preferably, the disorder is IOPD.

Other diseases of interest include, without limitation: hemophilia A, MPSI, Alzheimer's Disease, Parkinson's Disease, Huntington's Disease, Tourette Syndrome, schizophrenia, Sly disease, Hunter's disease, dementia, paranoia, obsessive compulsive disorder, learning disabilities, ALS, Charcot-Marie Tooth disease, Kennedy's disease, glioblastoma, neuroblastoma, autism, Gaucher's disease, Hurler's disease, Krabbe's disease, altered behaviors (e. g., disorders in sleeping, perception or cognition), One skilled in the art is aware of the transgene of interest useful in the treatment of these and other disorders by gene therapy. For example, the therapeutic transgene is: FVIII for hemophilia A, lysosomal enzymes α-L-iduronidase [IDUA (alphase-Liduronidase)], for MPSI, acid-α-glucosidase (GAA) for Pompe disease, Glycogen Debranching Enzyme (GDE) for Cori disease (GSDIII), G6P for GSDI, alpha-sarcoglycan (SGCA) for LGMD2D; dystrophin or its shortened forms for DMD; and SMN1 for SMA. The transgene of interest may also be a transgene that provides other therapeutic properties than providing a missing protein or a RNA suppressing the expression of a given protein. For example, transgenes of interest may include, without limitation, transgenes that may increase muscle strength, that may reduce apoptosis in the CNS or that may specifically kill cancer cells.

The inventors have shown that a vector comprising a transgene of interest under the control of the hybrid transcription regulatory element the invention has the beneficial effect to reduce pre-existing antibodies against the therapeutic protein encoded by said transgene (such as GAA) in a subject who has previously undergone ERT with said therapeutic protein. Accordingly, in a particular embodiment, the subject in need of the treatment is a subject who has previously received ERT for the treatment of a disease, such as a LSD. In a further particular embodiment, the subject was treated by ERT for a LSD or a GSD. In a further particular embodiment, the subject previously received an ERT treatment with GAA for Pompe disease. In a particular variant of this embodiment comprising the administration to a subject who has previously received an ERT treatment, the subject is further administered with an expression cassette, vector, cell or pharmaceutical composition according to the invention, in particular a vector such as a viral vector, more particularly an AAV vector. In a particular variant, the nucleic acid of the invention is a hybrid regulatory element comprising a first regulatory element capable of driving or enhancing liver-selective expression and a second regulatory element capable of driving or enhancing muscle-selective expression, comprising in particular (i) a combination of the ApoE enhancer and a hAAT promoter and (ii) a spC5.12 promoter.

As such, the invention relates to the expression cassette, vector, cell or pharmaceutical composition as described herein, comprising a hybrid regulatory element of the invention operably linked to a gene of interest encoding a therapeutic enzyme for use in the treatment of a disease by gene therapy, wherein the subject has previously undergone an ERT with the same enzyme. In a particular embodiment, the subject has previously undergone an ERT and developed an immune response to the enzyme that was administered.

Furthermore, the expression cassette, vector, cell or pharmaceutical composition as described herein comprises a hybrid regulatory element of the invention operably linked to a gene encoding an therapeutic enzyme may be used in a method for the treatment of a disease by reducing or eliminating the immune response induced by a previous ERT administered to the subject with the same enzyme.

In another embodiment, the invention relates to the expression cassette, vector, cell or pharmaceutical composition as described herein comprising a hybrid regulatory element of the invention operably linked to a gene encoding an therapeutic enzyme, for use in combination with an ERT with the same enzyme for the treatment of a disease. In a particular embodiment, the ERT is administered to the subject before or after, in particular before, the expression cassette, vector, cell or pharmaceutical composition as described herein.

In a further particular embodiment, the expression cassette, vector, cell or pharmaceutical composition as described herein comprises a hybrid regulatory element of the invention operably linked to a gene encoding a GAA, and is for use in a method for the treatment of Pompe disease in a subject who has previously received an ERT with GAA.

It should be understood that all the particular embodiments of the expression cassette, of the vector, of the cell and of the pharmaceutical composition of the invention also comprise the possibility for the transgene of interest to be any of the therapeutic transgene specifically disclosed in this application, preferably acid-alpha glucosidase (GAA). As is mentioned elsewhere in the present application, GAA may be used for the treatment of Pompe disease, such as for the treatment of infantile onset Pompe disease (IOPD) or late onset Pompe disease (LOPD). In a particular embodiment, the transgene of interest encodes a wild-type GAA protein comprising its native signal peptide. In another particular embodiment, the transgene of interest encodes a truncated GAA polypeptide, comprising a deletion of at least one amino acid from the N-terminal end of a parent GAA polypeptide, wherein the parent polypeptide corresponds to a precursor form of a GAA polypeptide devoid of its signal peptide, wherein said truncated GAA polypeptide has 1 to 75 consecutive amino acids deleted at its N-terminal end as compared to the parent GAA polypeptide, and wherein said truncated GAA polypeptide further comprises a signal peptide fused to its N-terminal end.

In a particular embodiment, the truncated GAA polypeptide has 1 to 75 consecutive amino acids deleted at its N-terminal end as compared to the parent GAA polypeptide, in particular 6, 7, 8, 9, 10, 40, 41, 42, 43, 44, 45 or 46 consecutive amino acids deleted at its N-terminal end as compared to a parent GAA polypeptide, even more particularly 8, 42 or 43 consecutive amino acids truncated at its N-terminal end as compared to a parent GAA polypeptide. In a particular embodiment, the parent polypeptide is a human GAA (hGAA), in particular the hGAA having the amino acid sequence shown in SEQ ID NO:14 or in SEQ ID NO:15, in particular in SEQ ID NO:14, or a hGAA which is a functional variant of the hGAA having the amino acid sequence shown in SEQ ID NO:14 or in SEQ ID NO:15, in particular in SEQ ID NO:14. In yet another embodiment, the truncated GAA polypeptide has the amino acid sequence shown in SEQ ID NO:16. The signal peptide which is fused to the truncated GAA polypeptide may be the natural signal peptide of GAA shown in SEQ ID NO:17, or an alternative signal peptide selected in the group consisting of SEQ ID NO:18 to 21, in particular the signal peptide of SEQ ID NO:18. In a particular embodiment, the truncated GAA polypeptide is of SEQ ID NO:16, and is fused to a signal peptide of SEQ ID NO:18 (polypeptide also referred to as "highly secretable GAA protein", or "sp7-Δ8-co" or "sec-hGAA" in the present application). Such truncated forms of GAA are disclosed in application PCT/EP2017/072944.

Methods of administration of the vector of the invention include but are not limited to intradermal, intramuscular, intraperitoneal, intravenous, subcutaneous, intranasal, epidural, locoregional administration as described in WO2015158924 and oral routes. In a particular embodiment, the administration is via the intravenous or intramuscular route. The vector of the invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical composition of the invention locally to the area in need of treatment, e.g. the liver or the muscle. This may be achieved, for example, by means of an implant, said implant being of a porous, nonporous, or gelatinous material, including membranes, such as sialastic membranes, or fibers.

The amount of the vector of the invention which will be effective in the treatment of disorder to be treated can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the vector of the invention administered to the subject in need thereof will vary based on several factors including, without limitation, the route of administration, the specific disease treated, the subject's age or the level of expression necessary to obtain the therapeutic effect. One skilled in the art can readily determine, based on its knowledge in this field, the dosage range required based on these factors and others. In case of a treatment comprising administering an AAV vector to the subject, typical doses of the vector are of at least $1\times10^8$ vector genomes per kilogram body weight (vg/kg), such as at least $1\times10^9$ vg/kg, at least $1\times10^{10}$ vg/kg, at least $1\times10^{11}$ vg/kg, at least $1\times10^{12}$ vg/kg at least $1\times10^{13}$ vg/kg, at least $1\times10^{14}$ vg/kg or at least $1\times10^{15}$ vg/kg.

In a particular embodiment, the vector of the invention may be administered at a dose lower than typical doses used in gene therapy. In particular, in a treatment comprising administering an AAV vector to the subject in need thereof, the vector may be administered at a dose at least 2-times lower than the above typical doses, in particular at a dose at least 3-times, 4-times, 5-times, 6-times, 7-times, 8-times, 9-times, 10-times, 11-times, 12-times, β-times, 14-times, 15-times, 16-times, 17-times, 18-times, 19-times, 20-times, 21-times, 22-times, 23-times, 24-times, 25-times, 26-times, 27-times, 28-times, 29-times, 30-times, 31-times, 32-times, 33-times, 34-times, 35-times, 36-times, 37-times, 38-times, 39-times, 40-times, 41-times, 42-times, 43-times, 44-times, 45-times, 46-times, 47-times, 48-times, 49-times, or even at least 50-times lower than the typical AAV doses typically used in gene therapy. In a particular embodiment, this lower dose reduction is used for the treatment of a LSD, in particular Pompe disease. In a further particular embodiment, the lower dose is used with a an AAV vector comprising a hybrid regulatory element according to the invention, comprising a first regulatory element capable of driving or enhancing liver-selective expression and a second regulatory element capable of driving or enhancing muscle-selective expression, comprising in particular (i) a combination of the ApoE enhancer and a hAAT promoter and (ii) a spC5.12 promoter.

EXAMPLES

Materials and Methods

GAA Expression Cassettes and AAV Vectors

The GAA transgene expression cassettes used in this study contained the codon-optimized human GAA (hGAA) coding sequence [Puzzo & Colella et al. Sci Transl Med. 2017 Nov. 29; 9(418)]. Codon-optimization was performed using a commercial algorithm (Thermo Fisher Scientific) [Puzzo & Colella et al. Sci Transl Med. 2017 Nov. 29; 9(418)]. The hGAA transgenes used are two: 1. hGAA, encoding for the native hGAA protein (hGAA); or 2. sec-hGAA, encoding for an engineered highly secretable GAA, having an heterologous signal peptide and a deletion of 8 amino-acids in the propeptide (sp7-Δ8-hGAAco, abbreviate as sec-hGAA in the text) [Puzzo & Colella et al. Sci Transl Med. 2017 Nov. 29; 9(418)]. Transgene sequences were cloned into an AAV vector backbone under the transcriptional control of the apolipoprotein E (hepatocyte control region enhancer) and the human alpha 1-antitrypsin (hAAT) promoter, the SPc5.12 promoter, or the CMV enhancer/chicken β-actin promoter (CAG) promoter. All DNA sequences used in the study were synthetized either by GeneCust or Thermo Fisher Scientific.

AAV vectors used in this study were produced using an adenovirus-free transient transfection method of HEK293 cells as described [Puzzo & Colella et al. Sci Transl Med. 2017 Nov. 29; 9(418)]. Titers of AAV vector stocks were determined using quantitative real-time PCR (qPCR) and SDS-PAGE followed by SYPRO Ruby protein gel stain and band densitometry. All vector preparations used in the study were quantified side-by-side before use. The primers used for qPCR on AAV genome annealed to BGH polyA (Fw: tctagttgccagccatctgttgt (SEQ ID NO:8); Rev: tgggagtggcaccttcca (SEQ ID NO:9) and codon-optimized hGAA (Fw: agatacgccggacattggactg (SEQ ID NO:10); Rev: gcacgcccagcagattgaac (SEQ ID NO:11). The AAV serotypes used are AAV8 and AAV9 that show a similar transduction profile upon systemic administration to mice (Zincarelli et al. Mol Ther. 2008 June; 16(6):1073-80).

In Vitro Experiments

Human hepatoma cells (HuH7), mouse myoblast C2 cells (C2) and mouse NSC34 cells were seeded in 6-well plates ($5 \times 10^5$ cells/well) and transfected using Lipofectamine 3000 (Thermo Fisher Scientific) accordingly to manufacturer's instructions. 72 hours after transfection, cells and conditioned media were harvested and analyzed for GAA activity and Western blot analyses. Human skeletal muscle myoblasts (CSC-C3196, Creative Bioarray) were seeded on collagen-coated 12-well plates and infected with AAV9-hGAA or AAV9-EGFP vectors 2 hours in OPTIMEM medium (Thermo Fisher Scientific) at a multiplicity of infection (MOI) of $2 \times 10^5$ vg/cell. After infection, cells were maintained in Creative Biorray SuperCult® Skeletal Muscle Cell Growth Medium Kit (Creative Bioarray) supplemented with 10% fetal bovine serum and human fibroblast growth factor-2 (FGF-2, Miltenyi Biotec). Infection was repeated twice, every 48H; cells were harvested 48 hours following the second infection.

Mouse Studies

Wild type C57BL/6 mice were purchased from Charles River (Charles River, France). The Gaa−/− mouse was generated by targeted disruption of exon 6 (Raben N. et al. J Biol Chem. 1998 Jul. 24; 273(30):19086-92). Gaa−/− mice in the C57BL/6J/129X1/SvJ background (FIG. 5, 6, 8, 9, 10, 11, 12, 13, 16, 17, 18) or DBA/2J C57 background (FIG. 7, 8, 14, 15) were used. Male littermate affected Gaa−/− and unaffected Gaa+/+ mice were used. AAV vectors were delivered to: 1. adult mice via the tail vein in a volume of 0.2 ml; 2. newborn mice at postnatal day 1-2 via the temporal vein in a volume of 0.03 ml. Experimental groups were sized to allow for statistical analysis; all the animals were included in the analysis and none of the outliers was excluded. Mice were assigned randomly to the experimental groups, and the operators who performed vector delivery and functional analyses were blinded to group identity. For the immunization-eradication studies 14 mice were treated by intravenous injection of rhGAA at the dose of 20 mg/kg every two weeks for a total of 3 administrations.

Each rhGAA infusion was performed 15 minutes after intraperitoneal administration of 25 mg/kg of antihistaminic (Diphenhydramine hydrochloride), as previously described. Two weeks after the last rhGAA administration anti-hGAA IgG were measured. The immunized Gaa−/− mice (n=8) were allocated to three AAV9-treatment groups ($2 \times 10^{12}$ vg/kg; AAV-Ctrl n=2, AAV-hAAT n=3, AAV-LiMP n=3).

GAA Activity

GAA activity was measured in mouse plasma (1/1000-1/2000 dilution) and tissues. Snap-frozen tissues were homogenized in di UltraPure™ DNase/RNase-Free Distilled Water (Thermo Fisher Scientific). 50-100 mg of tissue were weighed and homogenized, then centrifuged for 20 minutes at 10000×g to collect supernatant. The enzymatic reaction was set up using 10 µl of sample (plasma or tissue homogenate) and 20 µl of substrate—4 MUα-D-glucoside, in a 96 wells plate. The reaction mixture was incubated at 37° C. for one hour, and then stopped by adding 150 µl of Sodium Carbonate buffer pH 10.5. A standard curve (0-2500 pmol/µl of 4 MU) was used to measure released fluorescent 4 MU from individual reaction mixture, using the EnSpire alpha plate reader (Perkin-Elmer) at 449 nm (Emission) and 360 nm (Excitation). The protein concentration of the clarified supernatant was quantified by BCA (Thermo Fisher Scientific). To calculate the GAA activity, released 4 MU concentration was divided by the sample protein concentration and activity was reported as nmol/hour/mg protein.

Vector Genome Copy Number Analysis

DNA was extracted from tissues homogenates using the Nucleospin 8 (Macherey-Nagel, France) and quantified. Vector genome copy number was determined by qPCR using 100 ng of DNA, primers and probe annealed on the codon-optimized hGAA (Fw: agatacgccggacattggactg (SEQ ID NO:10); Rev: gcacgcccagcagattgaac (SEQ ID NO:11); probe gtgtggtcctcttgggagc (SEQ ID NO:12). Either Sybergreen or Taqman system was used as previously described. [Puzzo & Colella et al. Sci Transl Med. 2017 Nov. 29; 9(418)]. VGCN were normalized by microgram of DNA used in the qPCR. To quantify VGCN per diploid genome, DNA was extracted from tissues homogenates using Gentra Puregene Tissue kit (Qiagen) and quantified.

RNA Extraction and Expression Analysis

Snap-frozen tissues were weighted and 50-100 mg were homogenized in Trizol reagent (Thermo Fisher Scientific). Total RNA was extracted from tissue homogenates using the PureLink RNA mini kit with PureLink DNAse set (Thermo Fisher Scientific). RNA was quantified and 2-5 ug were retro-transcribed to cDNA using the Maxima First Strand cDNA Synthesis Kit for RT-qPCR with dsDNase (Thermo Scientific); RT-minus reactions were performed as negative control. For hGAA RNA expression, qPCR analyses on cDNA were performed using Sybergreen and primers annealing on codon-optimized hGAA (Fw: agatacgccgga-cattggactg (SEQ ID NO: 10); Rev: gcacgcccagcagattgaac (SEQ ID NO:11); primers annealing on mouse Actin gene were used to normalize hGAA expression (mActin Fw: ggctgtattcccctccateg (SEQ ID NO:22); mActin Rev: ccagttggtaacaatgccatgt (SEQ ID NO:23); mouse Actin and beta-2 microglobulin (B2m; B2m Forward: 5'-ggtctttctggtgcttgtctca-3'; B2m Reverse: 5'-gttcggcttcccat-tctcc-3') were used to normalize hGAA expression for data depicted in FIG. 17. For Rtl1 expression analyses the qPCR on cDNA was performed using the TaqMan method, commercial probes and primers previously reported by Chandler and co-authors (Chandler et al, JCI, 2015 February;125 (2): 870-80) and the Maxima ROX qPCR Master Mix (Thermo Scientific). The TaqMan gene expression assays (#4331182, Thermo Scientific) were the following: Rtl1 (Mm02392620_s1; Gapdh (Mm 99999915_g1).

Western Blot Analyses

HuH7, C2 and NSC34 cell lysates were prepared using 10 mM PBS (pH7.4) containing 1% of Triton-X100 and protease inhibitors (Roche Diagnosis). Western blot on mouse plasma was performed on samples diluted 1:4 in distilled water. Mouse tissues were prepared as indicated for GAA activity. Protein concentration was determined using the BCA Protein Assay (Thermo Fisher Scientific). SDS-page electrophoresis was performed in a 4-15% gradient polyacrylamide gel. SDS-page electrophoresis was performed in a 4-15% gradient polyacrylamide gel. After transfer the membrane was blocked with Odyssey buffer (Li-Cor Biosciences) and incubated with an anti-GAA antibody (mouse monoclonal, SantaCruz Biotechnology, or rabbit monoclonal, Abcam), anti-eGFP (mouse monoclonal, Santa Cruz) or anti-tubulin (mouse monoclonal, Sigma Aldrich); anti-p62 (mouse monoclonal, Abcam) anti-Parkin (rabbit polyclonal, Abcam); Gapdh (rabbit polyclonal, Thermo Fischer Scientific). The membrane was washed and incubated with the appropriate secondary antibody (Li-Cor Biosciences), and visualized by Odyssey imaging system (Li-Cor Biosciences).

Anti-GAA Antibody Detection

Anti-GAA antibody measurement was performed according to a published protocol. Briefly, maxisorp 96 wells plates (Thermo Fisher Scientific) were coated with 1 µg/ml of rhGAA. IgG standard curves were made by serial 1 to 2 dilutions of commercial mouse (Sigma Aldrich) recombinant IgG which were coated directly onto the wells in duplicate. Anti-mouse (Southern biotech) IgG secondary antibodies were used as secondary antibodies.

Functional Assessment

Grip strength was measured as already reported. Using a grip strength meter, (Columbus instruments) three independent measurements of the four limbs strength were calculated. Mean values of the grip strength/mouse was calculated.

Respiratory function during quiet breathing was evaluated as already reported [DeRuisseau et al., PNAS, 2009]. Briefly, a flow-through (0.5 L/min) plethysmograph (EMKA technologies) was used to measure the breathing pattern in treated Gaa−/− mice and controls. The instrument was calibrated with known airflow and pressure signals before data collection. Signals were analyzed by using the IOX2 software (EMKA technologies). Animals were allowed for acclimation into the plethysmograph chamber before testing. During both acclimation and data acquirement, mice were breathing normoxic air (21% O2, 79% N2).

Results

1. Cloning of Multi Tissue Promoters in AAV Plasmids

We selected from the literature basic single-tissue transcription regulatory elements to evaluate the possibility of generating multi-tissue promoters.

For liver we selected the hepatocyte-restricted Apolipoprotein (ApoE) enhancer (SEQ ID NO: 4) with human alpha-1 anti-trypsin (hAAT) promoter (SEQ ID NO: 2).

For muscle we selected the synthetic spC5.12 muscle-selective promoter (SEQ ID NO: 1).

For neurons we selected the pan-neuron human Synapsin (hSYN) promoter (SEQ ID NO: 3).

Based on these transcription regulatory elements we generated 3 different multi-tissue promoters (FIG. 1).

Liver Enhanced-Muscle Promoter (Referred as Enh.C5.12), SEQ ID NO: 5

This promoter was generated by cloning the ApoE hepatocyte control region/enhancer upstream of the synthetic spC.12 muscle-selective promoter.

Liver-Muscle Promoter (LiMP), SEQ ID NO: 6

This promoter was generated by cloning the ApoE hepatocyte control region and the hAAT promoter upstream of the synthetic spC5.12 muscle-selective promoter.

Liver-Neuron Promoter (LiNeuP), SEQ ID NO: 7

This promoter was generated by cloning the ApoE hepatocyte control region and the hAAT promoter upstream of the hSYN promoter.

A codon-optimized human GAA transgene (hGAA) was cloned in all the expression cassettes (FIG. 1 and Table 1). Two versions of the hGAA were used: the native one and an engineered highly secretable one having a heterologous signal peptide (sp7-Δ8-co, referred as sec-hGAA; Table 1) [Puzzo & Colella et al. Sci Transl Med. 2017 Nov. 29; 9(418) An improved synthetic human beta-globin-derived (HBB2.1) intron was inserted between the promoters and the GAA transgene to stabilize the transgene mRNA (Ronzitti et al. Molecular therapy Methods & clinical development. 2016; 3:16049). The HBB2 intron was exchanged with the short SV40 intron (Trapani et al., EMBO molecular medicine. 2014; 6(2):194-211) in LiMP- and LiNeuP-expression cassettes to fit the AAV DNA packaging limit (Table 1).

TABLE 1

List of all GAA expression cassettes used

| Regulatory element | Tissue selectivity | Promoter short name | Enhancer | Promoter | hGAA codon-optimized | |
|---|---|---|---|---|---|---|
| REPORTED | Single tissue | C5.12 | No | spC5.12 | Native (referred to as hGAA) | Highly secretable (sp7-Δ8-co, referred to as sec-hGAA) |
| | Single tissue | hAAT | ApoE | hAAT | | |
| | Single tissue | hSYN | No | hSYN | | |
| ORIGINAL (invention) | Multi-tissue | Enh.C5.12 | ApoE | spC5.12 | | |
| | Multi-tissue | LiMP | ApoE | hAAT + spC5.12 | | |
| | Multi-tissue | LiNeuP | ApoE | hAAT + hSYN | | |

2. Evaluation of Multi-Tissue Promoters in Cell Lines

First, we tested the multi-tissue promoters in vitro in cell lines in comparison to the basic single tissue promoters (FIG. 2-3). A highly secretable version of the GAA transgene was used as model therapeutic gene [Puzzo & Colella et al. Sci Transl Med. 2017 Nov. 29; 9(418)]. We evaluated the ability of Enh.C5.12 and LiMP hybrid liver-muscle promoters to drive sec-hGAA expression in both hepatocyte and muscle cell lines (FIG. 2A). To this aim we transiently transfected the HuH7 human hepatocyte cell line (FIG. 2A) and the C2 mouse myoblast cell line (FIG. 2B). Then we evaluated GAA enzyme activity in cell media and protein expression in cell lysates by Western blot analyses (FIG. 2). In hepatocyte cells, the full liver-muscle promoter LiMP (hAAT+C5.12), but not the Enh.C512, showed significantly higher activity compared to C5.12 (FIG. 2A). The Enh.C512 (ApoE+C5.12) indeed provided a small but nonsignificant increase of enzyme activity as compared to C5.12 (FIG. 2A). In muscle cells, both LiMP and Enh.C5.12 showed significantly higher activity compared to both C5.12 and hAAT (FIG. 2A). These features make LiMP a good candidate for strong liver-muscle transgene expression. Notably, the increased transcriptional activity we found using Enh.C5.12 and LiMP in muscle cells (FIG. 2A) was unexpected based on the combination of a muscle-selective promoter (spC5.12) with hepatocyte-selective regulatory elements (ApoE/hAAT). Then, we evaluated the ability of the liver-neuron LiNeuP promoter (hAAT+hSYN) to drive sec-hGAA expression in both hepatocyte and neuronal cell lines (FIG. 1E-H; FIG. S2C-D). To this aim we transiently transfected the HuH7 hepatocyte cells and the NSC34 mouse neuronal cell line (spinal cord neuron×neuroblastoma hybrid cell line) (FIG. 3). In hepatocytes we found that LiNeuP lead to significant enzyme activity in media and significant protein amounts in lysates (FIG. 3A). In neuronal cells, LiNeuP lead to significant enzyme activity in media (FIG. 3B), and lead to clear GAA protein expression in cell lysates (FIG. 3B). Thus LiNeuP can induce expression in both hepatocytes and neuronal cells while each of the individual promoters comprised in this novel hybrid promoter can only drive expression in hepatocytes (for hAAT) or neuronal cells (for hSYN). In summary, the ability of LiNeuP to drive efficient transgene expression in both hepatocyte and neuronal cells makes it a promising hybrid liver-neuron promoter.

3. Evaluation of Multi Tissue Promoters in Animal Models

To evaluate the tissue selectivity and the tolerogenic properties of Enh.C5.12, LiMP and LiNeuP promoters in vivo we produced AAV vectors and performed gene transfer in the C57Bl/6 mouse model and in the mouse model of Pompe disease.

I. EVALUATION OF PROMOTER ACTIVITY IN WILD TYPE B6 MICE AFTER SYSTEMIC AAV GENE TRANSFER

To assess the ability of the newly generated Enh.C5.12, LiMP and LiNeuP promoters to drive expression in different tissues, as designed, we generated AAV vector of serotype 9 that is able to infect liver, muscle and neurons upon intravenous administration to animal models. We used as transgene the native human GAA (hGAA) which is the full length GAA codon optimized. In this study we compared both the ubiquitous CAG promoter, single tissue promoters (hAAT, C5.12 and hSYN) and our multi-tissue promoters (Enh.C5.12, LiMP and LiNeuP, Table 2). This study provides data about the ability of these promoters to provide hGAA to the circulation and the activity of all promoters in the desired tissues (Liver, Heart, Quadriceps, Spinal Cord and Brain).

One month after intravenous injection of AAV9 vectors encoding for native GAA, circulating GAA protein was very low or barely detectable using the C5.12 and hSYN promoters while it was clearly detected using the multi-tissue promoters Enh.C5.12, LiMP and LiNeuP promoters (FIG. 4A). LiMP and LiNeuP resulted to be the best performing hybrid promoters among those generated to provide hGAA protein to the circulation for therapeutic cross-correction (FIG. 4A).

Mouse tissues from the treated mice were collected 6 weeks after treatment for RNA expression analysis (FIG. 4B). The expression of the hGAA RNA was evaluated in liver, cardiac muscle (heart), skeletal muscle (quadriceps) and CNS (spinal cord and brain). The hGAA expression was normalized by the expression of a reference mouse gene (Actin). FIG. 4B shows the relative expression of the hGAA mRNA in all the tissue analyzed. As observed in vitro (FIG. 2 A-B), the hAAT promoter is active in liver but not in muscle (heart and quadriceps) while the C5.12 promoter is active in muscle but not in liver. Notably we found that the multi-tissue promoter LiMP is able to drive efficient transgene expression in both liver and muscle, indicating that it is a hybrid liver-muscle promoter (FIG. 4B). Differently, Enh.C5.12 promoter is able to drive high expression in muscle but low expression in liver. Indeed in liver Enh.C5.12 provided significantly lower transgene expression compared to hAAT and a slightly higher but not significant expression compared to the C5.12 promoter (FIG. 4B). Therefore, Enh.C5.12 can be used when it is required a strong expression in muscle and a weak expression in liver. As we observed in vitro (FIG. 3), the liver-neuron promoter LiNeuP is able to drive high GAA expression in both liver and CNS (FIG. 4B). Importantly, we confirmed that the basic hAAT and hSYN promoters are not active in CNS and liver, respectively (FIG. 4B). Notably, the tissue selectivity of LiMP and LiNeuP was preserved, as they remained not active in neurons and muscle, respectively (FIG. 4B). Overall the hGAA transgene expression data clearly show the generation of hybrid promoters which are able to drive multi-tissue-selective transgene expression. As expected, vector genome copy number (VGCN) analyses in the tissues analyzed showed that most of the AAV vector transduces to the liver upon intravenous injection in mice (Zincarelli et al. Mol Ther. 2008 June; 16(6):1073-80). No significant differences in VGCN were observed among the different vectors (FIG. 4B).

5A). GAA enzyme activity in mouse plasma confirmed that the hybrid Enh.C5.12 and LiMP promoters provide higher GAA protein levels to the circulation for therapeutic purposes compared to C5.12 (FIG. 5B).

TABLE 2

Promoters evaluated in vivo in study I.

| Regulatory element | Tissue selectivity | Promoter short name | Enhancer | Promoter | hGAAco |
|---|---|---|---|---|---|
| REPORTED | Ubiquitous | CAG | CMV | CAG | Native (referred to as hGAA) |
| | Single tissue | C5.12 | no | spC5.12 | |
| | Single tissue | hAAT | ApoE | hAAT | |
| | Single tissue | hSYN | no | hSYN | |
| ORIGINAL (INVENTION) | Multi-tissue | Enh.C5.12 | ApoE | spC5.12 | |
| | Multi-tissue | LiMP | ApoE | hAAT + spC5.12 | |
| | Multi-tissue | LiNeuP | ApoE | hAAT + hSYN | |

II. EVALUATION OF ACTIVITY AND TOLEROGENIC PROPERTIES OF LIVER/MUSCLE PROMOTERS IN MOUSE MODELS OF POMPE DISEASE (GAA-/-) AFTER SYSTEMIC AAV GENE TRANSFER

In this study we compared liver and muscle single-tissue promoters (hAAT and C5.12) to our multi-tissue liver+muscle promoters (Enh.C5.12, LiMP) driving the expression of both the native (hGAA) and a highly secretable (sec-hGAA) GAA proteins (Table 3). The Gaa-/- mice are used to model Pompe patho-physiology. We and others previously reported that the expression of native GAA in Gaa-/- muscle induces a strong humoral immune response towards the protein [Puzzo & Colella et al. Sci Transl Med. 2017 Nov. 29; 9(418)], Zhang. Et al. Hum Gene Ther. 2012 May; 23(5):460-72). Then, we recently showed that a highly secretable GAA protein is less immunogenic than the native one [Puzzo & Colella et al. Sci Transl Med. 2017 Nov. 29; 9(418)]. Therefore this study provides data about the tolerogenic properties of the newly developed hybrid liver-muscle promoters (Enh.C5.12 and LiMP) in the context of high and low immunogenicity provided by the use of native and highly secretable GAA forms, respectively. The ability of the promoters to provide GAA in the circulation for therapeutic purposes was also evaluated. When we delivered AAV expressing the immunogenic native GAA protein (hGAA) to Gaa-/- mice, we observed that GAA expression driven by promoters shown in study I to be mostly expressed in muscles, C5.12 and Enh.C5.12 (FIG. 4B) resulted in humoral immune response to the protein (FIG. 5A). Notably, the use of the hybrid liver-muscle LiMP promoter significantly prevented the induction of anti-hGAA immune responses (FIG. 5A). These data prove that the strong GAA liver expression provided by LiMP (as reported in study I, FIG. 4B) induced immunological tolerance to hGAA (FIG.

Next, muscle being a highly immunogenic tissue, we tested whether AAV gene transfer using the LiMP promoter could eradicate a pre-existing anti-transgene humoral immune response.

To this aim, we immunized Gaa-/- mice by three intravenous injections of recombinant human GAA (rhGAA) at a dose of 20 mg/kg (FIG. 6A). Then, two weeks after we measured anti-GAA IgG in plasma and treated the immunized mice with AAV9-LiMP-hGAA vectors by intravenous delivery (FIG. 6B). An AAV9-hAAT-hGAA vector was used as tolerogenic control. Six weeks after AAV treatment (dose of $2\times10^{12}$ vg/kg), IgG anti-hGAA were significantly decreased in mice treated with LiMP and hAAT vectors but not with a control AAV vector expressing luciferase (FIG. 6B).

Overall, these results indicate that AAV gene transfer with dual promoters endowed with a strong liver expression component results in dominant transgene immune tolerance.

TABLE 3

Promoters evaluated in vivo in study II.

| Regulatory element | Tissue selectivity | Promoter short name | Enhancer | Promoter | hGAAco | |
|---|---|---|---|---|---|---|
| REPORTED | Single tissue | C5.12 | no | spC5.12 | Native (hGAA) | secretable (sp7-Δ8-co, sec-hGAA)) |
| ORIGINAL | Multi-tissue | Enh.C5.12 | ApoE | spC5.12 | | |
| (INVENTION) | Multi-tissue | LiMP | ApoE | hAAT + spC5.12 | | |

III. EVALUATION OF TOLEROGENIC PROPERTIES AND THERAPEUTIC EFFICACY OF HYBRID LIVER-MUSCLE AND LIVER/NEURONS PROMOTERS IN ADULT GAA-/- MICE BY SYSTEMIC AAV GENE TRANSFER

Based on our previous data (FIGS. 2-5), in this study we tested the advantages of using the best performing tolerogenic multi-tissue promoters (LiMP and LiNeuP) to rescue the whole-body disease phenotype of Gaa-/- mice. In particular we evaluated the therapeutic efficacy of AAV vectors expressing a highly secretable GAA protein (sp7-Δ8-co, referred to as sec-hGAA) under the control of the liver-selective hAAT promoter, the liver-muscle LiMP promoter and the liver-neuron LiNeuP promoter (Table 4). AAV vectors expressing sec-hGAA under the control of the ubiquitous CAG promoter were used as control. In the context of Pompe disease, the expression of secretable GAA from the liver into the circulation would allow targeting other tissues by protein uptake. However, GAA uptake is limited in skeletal muscle and neurons by: 1. low levels of GAA receptor on the cell surface and 2. autophagy block that impairs GAA targeting to lysosomes; then, the size restriction imposed by the blood-brain barrier significantly limits GAA bio-distribution to the CNS.

In view of our results reported above, we expected that by co-expressing GAA in liver and other affected tissues we will achieve higher therapeutic efficacy than by targeting liver alone. Importantly, in study III, we showed that liver targeting thanks to our new multi-tissues promoters provides immunological tolerance to the expressed GAA transgene (please see FIG. 5A). Analyses of sec-hGAA protein levels in the circulation and humoral immune response to GAA in study III confirmed that the LiMP and LiNeuP promoters provide similar levels of GAA when compared to hAAT (FIG. 7, upper panel) in the absence of humoral immune response (FIG. 7, anti-GAA IgG levels indicated below the western-blot photograph). Notably, strong immune response to GAA is observed when using the ubiquitous CAG promoter (FIG. 7, upper panel). The CAG promoter also provided significant lower amounts of circulating GAA compared to hAAT, LiMP and LiNeuP (FIG. 7, lower panel). These data demonstrate that a hybrid liver-based multi-tissue promoters, according to the invention, have advantages over ubiquitous promoters. Notably, ubiquitous GAA expression driven by the CAG promoter, which also leads to expression in the liver, does not necessarily result in immune tolerance to the transgene product, while the plasma of all the mice receiving LiMP and LiNeuP driven GAA vectors contained no detectable anti-GAA IgG. The above results surprisingly show that a careful selection of multiple tissue-selective promoters leads to transgene expression in several tissues of interest and immune tolerance, in contrast to what could be achieved with either muscle-selective promoters or with ubiquitous promoters. Based on these promising results, we then evaluated the therapeutic efficacy of AAV vectors expressing sec-hGAA under the control of the LiMP and LiNeuP promoters in Gaa-/- mice. GAA enzyme activity in the circulation confirmed GAA expression from all AAV tested (FIG. 8A). Muscle strength is significantly decreased in untreated Gaa-/- mice (Ctrl, FIG. 8B) compared to unaffected Gaa+/+ mice (Ctrl, FIG. 8B). Notably, Gaa-/- mice treated with AAV-sec-hGAA gene therapy using LiMP and LiNeuP showed no significant differences in muscle strength compared to unaffected Gaa+/+(FIG. 8B). Notably significant rescue was also observed in Gaa-/- mice treated with AAV-LiNeuP vectors compared to untreated Gaa-/- mice (Ctrl, FIG. 8B). Respiratory function in Gaa-/- treated by AAV expressing sec-hGAA under the control of the LiMP and LineUP promoters was significantly improved in Gaa-/- mice compared to untreated Gaa-/- mice (Ctrl) and was comparable to Gaa+/+ animals (FIG. 8C, D).

IV. EVALUATION OF THERAPEUTIC EFFICACY OF LIVER/MUSCLE PROMOTER LiMP IN NEWBORNS GAA-/- MICE BY SYSTEMIC AAV GENE TRANSFER

In this study, we tested the advantage of using the liver-muscle tolerogenic multi-tissue promoter LiMP to determine whether persistent GAA expression and therapeutic efficacy could be achieved in a condition of hepatocyte proliferation which could lead to dilution of the AAV genomes from liver and therapeutic efficacy [Wang et al, Hum Gene Ther. 2012 May; 23(5):533-9]. To this aim we have injected Gaa-/- mice with AAV vectors, mimicking the treatment of Pompe subjects during the early post-natal stage. Therapeutic intervention in the first months of life is an important medical need for PD subjects presenting the infantile form of the disease [infantile onset PD (IOPD)] [Chien et. al., Pediatr Neonatol. 2013 August; 54(4):219-27]. Notably, newborn screening for PD has been approved in many countries and may facilitate timely therapeutic interventions. In particular, here we evaluated the advantage of expressing the highly secretable GAA protein (sp7-Δ8-co, referred to as sec-hGAA) from single tissue promoters [muscle (C5.12) and liver (hAAT)] compared to the LiMP promoter (Table 5) that provides GAA expression in both liver and muscle (as observed in study I, FIG. 4B) and provides the therapeutic enzyme to the circulation (study I, FIG. 4A).

The analysis of GAA protein in the circulation 3 months after treatment of newborns Gaa-/- mice with AAV-sec-hGAA vectors showed that similar protein amount are achieved with hAAT and LiMP promoters, this is consistent with the effect of liver proliferation on both AAV genomes (FIG. 9). Notably, circulating GAA provided by the muscle promoter C5.12 was significantly lower than that provided by hAAT and LiMP promoters (FIG. 9A-B). GAA activity in cardiac and skeletal muscle was also significantly higher in heart, diaphragm, triceps and quadriceps of Gaa-/- mice treated with AAV-LiMP compared to AAV-05.12 or AAV-hAAT vectors (FIG. 9C-F). Notably, the amount of therapeutic GAA protein was significantly higher in muscle (such as triceps) and CNS (spinal cord) of Gaa-/- mice treated with LiMP vectors compared to C5.12 and hAAT vectors (FIG. 10A-B). In brain (FIG. 10C) significant higher GAA protein was observed in Gaa-/- mice treated with LiMP vectors compared to those treated with C5.12 vectors. This result reflects the hybrid transcriptional activity of the LiMP promoter which allows transgene expression from both liver (FIG. 10 D) for cross-correction together with endogenous transgene expression in muscle (FIG. 10E). Notably, since hAAT and LiMP vectors provided similar amount of enzyme to the circulation (FIG. 9A-B), the higher expression achieved with LiMP in muscle (FIG. 10A) and spinal cord (FIG. 10B) results from endogenous transgene expression in

TABLE 4

Promoters evaluated in vivo in study III.

| Regulatory element | Tissue selectivity | Promoter short name | Enhancer | Promoter | hGAAco |
|---|---|---|---|---|---|
| REPORTED | Ubiquitous | CAG | CMV | CAG | secretable (sp7-Δ8-co) |
|  | Single tissue | hAAT | ApoE | hAAT |  |
| ORIGINAL (INVENTION) | Multi-tissue | LiMP | ApoE | hAAT + spC5.12 |  |
|  | Multi-tissue | LiNeuP | ApoE | hAAT + hSYN |  | muscle (FIG. 10E). Importantly muscle strength in Gaa−/− mice was significantly preserved only by treatment with AAV encoding sec-hGAA under the control of the LiMP promoter (FIG. 11). This is the result of GAA secretion in the circulation (FIG. 9A-B) and high GAA expression in muscle (FIG. 9C-D-F and FIG. 10A) achieved only by using the hybrid LiMP promoter but not the single tissue C5.12 and hAAT promoters.

It has been previously reported that systemic AAV gene transfer to newborn mice results in the integration of part of the vector genomes into the liver genomic DNA (Chandler et al, JCI, 2015 February; 125(2):870-80). Most of the integrations occurs in a mouse-specific genomic hotspot (Rian locus) promoting hepatic genotoxicity and the development of hepatocellular carcinoma (HCC) only when CAG and TBG, but not hAAT promoters are used (Chandler et al, JCI, 2015 February; 125(2):870-80). This is due to the strong transactivation activity of CAG and TBG promoters that induces the upregulation of the HCC-associated Rtl1 gene, which is close to Rian (Chandler et al, JCI, 2015 February; 125(2):870-80). Notably, we found that the Rian RNA was not upregulated in Gaa−/− mice treated as newborns with AAV-LiMP vectors compared to both untreated and AAV-hAAT-treated Gaa−/− mice (FIG. 12). No significant Rtl1 transactivation was also observed in Gaa−/− mice treated with AAV-05.12 vectors compared to untreated Gaa−/− mice (FIG. 12). Therefore, the use of the hAAT promoter in our hybrid LiMP and LiNeUP promoters and of the C5.12 promoter in LiMP provides additional favorable features to our hybrid regulatory elements for in vivo gene therapy.

Then, differently from ubiquitous promoters, the present invention prevents ectopic transgene expression in tissues that do not express physiologically the therapeutic transgene of interest or where the expression of the transgene of interest is not desired. Therefore the present invention may also prevent possible toxicities recently reported in preclinical studies in Non Human Primate treated by systemic delivery of AAV vectors injected at high doses and containing the ubiquitous chicken beta actin promoter (Hinderer et al., Hum Gene Ther. 2018 Feb. 12).

among the LiMP and hAAT promoters. GAA activity was instead significantly higher in heart (FIG. 13C), diaphragm (FIG. 13D) quadriceps (data not shown) and triceps (FIG. 13E) of Gaa−/− mice treated with LiMP compared to hAAT. The use of the LiMP promoter also resulted in higher amounts of hGAA protein in triceps (as representative muscle) and spinal cord (FIG. 13F) of AAV-treated Gaa−/− mice. No differences were found in brain hGAA amounts when using LiMP and hAAT promoters (FIG. 13G).

Glycogen was significantly reduced upon treatment with LiMP vectors in heart (FIG. 13H), diaphragm (FIG. 13I), quadriceps (data not shown) and triceps (FIG. 13J) of Gaa−/− mice as compared to both untreated (Ctrl) and hAAT-treated Gaa−/− mice. In spinal cord and brain, significant glycogen reduction was observed in all AAV-treated Gaa−/− mice compared to untreated Gaa−/− mice (Ctrl) despite at levels still different from unaffected Gaa+/+(FIG. 13K). Notably, significant rescue of cardiomegaly (FIG. 13L) and muscle strength (FIG. 13M) was observed only in Gaa−/− mice treated with LiMP vectors as compared to untreated Gaa−/− mice. VGCN in the liver and quadriceps showed similar levels of tissue transduction (data not shown).

IgG to hGAA were not detected in plasma of AAV-treated Gaa−/− mice analyzed monthly by ELISA assay (Table 6).

TABLE 6

| Months post injection[a] | IgG (µg/mL) | | | |
|---|---|---|---|---|
| | 1 | 2 | 3 | 4 |
| hAAT (n = 5)[b] | 0 ± 0.0[c] | 0 ± 0.0 | 0 ± 0.0 | 0 ± 0.0 |
| LiMP (n = 6) | 0 ± 0.0 | 0 ± 0.0 | 0 ± 0.0 | 0 ± 0.0 |

[a] AAV dose: $6 \times 10^{12}$ vg/kg ($1.2 \times 10^{10}$ vg/pup)
[c] Mean ± SD
[b] n of mice As observed in Gaa−/− mice treated with AAV8 vectors (FIG. 12), no significant transactivation activity upon the Rtl1 oncogene was observed in the liver of Gaa−/− mice treated with AAV9 vectors containing either hAAT or LiMP promoters as compared to untreated Gaa−/− mice.

TABLE 5

Promoters evaluated in vivo in study IV.

| Regulatory element | Tissue selectivity | Promoter short name | Enhancer | Promoter | hGAAco |
|---|---|---|---|---|---|
| REPORTED | Single tissue | C5.12 | no | spC5.12 | secretable (sp7-Δ8-co, referred to as sec-hGAA) |
| | Single tissue | hAAT | ApoE | hAAT | |
| ORIGINAL (INVENTION) | Multi-Tissue | LiMP | ApoE | hAAT + spC5.12 | |

V. EVALUATION OF THE LIVER/MUSCLE PROMOTER LiMP ABILITY TO PROVIDE SUSTAINED THERAPEUTIC EFFICACY IN NEONATE GAA−/− MICE AT LOW VECTOR DOSES

We next asked whether AAV gene therapy with LiMP-sec-hGAA vectors in neonate Gaa−/− mice could result in therapeutic efficacy at low vector doses [$1.2 \times 10^{10}$ vg/pup ($6 \times 10^{12}$ vg/kg); FIG. 13]. At the end of the study (4 months after treatment), the amount of enzyme in the bloodstream was not different in Gaa−/− mice treated with LiMP and hAAT vectors (FIG. 13A-B). The analysis of hGAA RNA expression in the liver also showed no significant differences Overall these results show that the dual liver-muscle promoter LiMP allows to achieve superior therapeutic efficacy as compared to the hAAT promoter in neonate animals following systemic AAV liver gene therapy at low vector doses.

VI. THE LIVER/MUSCLE PROMOTER LiMP PROVIDE LEVELS OF GAA TO MUSCLE NOT DIFFERENT FROM A STRONG UBIQUITOUS PROMOTER FOLLOWING SYSTEMIC AAV GENE TRANSFER IN NEWBORNS GAA−/− MICE

In this study we evaluated the amount of GAA provided to muscle when using the liver-muscle LiMP and liver-neuron LiNeuP promoters in comparison to a strong ubiquitous promoter following systemic AAV gene transfer in newborns Gaa−/− mice. In this settings, as shown above, hepatocyte proliferation lead to dilution of the AAV genomes from liver and therapeutic efficacy [Wang et al, Hum Gene Ther. 2012 May; 23(5):533-9]. We have injected Gaa−/− mice with AAV vectors encoding a highly secretable GAA protein (sp7-Δ8-co, referred to as sec-hGAA) from the ubiquitous promoter CAG [the CMV enhancer/chicken beta-actin promoter (CAG) promoter] compared to the LiMP and LiNeuP promoters (Table 7); the single liver promoter hAAT was used as control (Table 7).

The analysis of GAA protein in skeletal muscle (Triceps, FIG. 14) 4 months after treatment of newborns Gaa−/− mice with AAV-sec-hGAA vectors showed that similar protein amounts are achieved with CAG and LiMP promoters which were both higher than those achieved with hAAT and LiNeuP. This is consistent with the effect of liver proliferation on AAV genomes which are significantly lost over mouse growth and lack of transcriptional activity of hAAT and LiNeuP in muscle (FIG. 14).

TABLE 7

Promoters evaluated in vivo in studies VI and VII.

| Regulatory element | Tissue specificity | Promoter short name | Enhancer | Promoter | hGAAco |
|---|---|---|---|---|---|
| REPORTED | Ubiquitous | CAG | CMV | CAG | secretable (sp7-Δ8-co, referred to as sec-hGAA) |
|  | Single tissue | hAAT | ApoE | hAAT |  |
| ORIGINAL (INVENTION) | Multi-Tissue | LiMP | ApoE | hAAT + spC5.12 |  |
|  |  | LiNeuP | ApoE | hAAT + hSYN |  |

VII. THE LIVER/MUSCLE PROMOTER LiMP NORMALIZES AUTOPHAGY AND MITOPHAGY IN MUSCLES OF GAA−/− MICE FOLLOWING NEONATAL AAV GENE TRANSFER

In this study we evaluated the normalization of p62 (a marker of autophagy block) and Parkin (a marker of mitophagy) in muscles of Gaa−/− mice treated as neonates by systemic AAV gene transfer. To this aim, we have injected Gaa−/− mice with AAV vectors encoding a highly secretable GAA protein (sp7-Δ8-co, referred to as sec-hGAA) from the liver-muscle promoter LiMP compared to the single liver promoter hAAT. As expected from the data reported above, 4 months after treatment of newborns Gaa−/− mice, GAA protein was higher in triceps of mice treated with LiMP compared to hAAT (FIG. 15A-B). Then, p62 was increased in triceps of untreated Gaa−/− mice compared to unaffected Gaa+/+, reflecting autophagy block (FIG. 15C). Notably, p62 content was normalized in the triceps of Gaa−/− mice treated with LiMP but not hAAT vectors (FIG. 15A, B). Parkin amount was instead significantly reduced in tricep of untreated Gaa−/− mice compared to unaffected Gaa+/+ (FIG. 15A, C), reflecting impaired mitophagy. Notably normal Parkin content was restored in triceps of Gaa−/− mice upon treatment with LiMP vectors but not hAAT vectors (FIG. 15A, C). The analysis of vector genome copy numbers (VGCN) in liver and triceps of mice depicted in FIGS. 15 and 16 showed no significant differences except for the CAG vector for which significant higher VCGN were found in the liver (FIG. 16 A-B).

VIII. SPECIFICITY OF LIMP AND LINEUP PROMOTER UPON SYSTEMIC AAV GENE THERAPY IN MICE

The specificity of the liver-muscle promoter LiMP and liver-neuron promoter LiNeuP was confirmed by the low or absent activity observed in non-target tissues such as kidney, lung and spleen (FIG. 17 A-B). In the lung, some detectable hGAA mRNA expression observed using the LiMP promoter could possibly derive from promoter activity in smooth muscle cells (FIG. 17B). As expected, VGCN were higher in liver compared to other tissues (FIG. 17 C-D). Overall, the hGAA mRNA expression data show that the hybrid promoters LiMP and LiNeuP drive efficient and specific transgene expression in target tissues (FIG. 17).

IX. HYBRID PROMOTERS WITH STRONG LIVER ACTIVITY PREVENT THE DEVELOPMENT OF IMMUNE RESPONSES TO HGAA IN GAA−/− MICE

Gene transfer of native hGAA to Gaa−/− mice driven by either ubiquitous or muscle-specific promoters has been reported to induce unwanted humoral immune responses towards the hGAA protein [Falk et al., Mol Ther Methods Clin Dev. 2015 Mar. 25; 2:15007; Franco et al. Mol Ther. 2005 November; 12(5):876-84]. Conversely, we [Puzzo et al., Sci Transl Med. 2017 Nov. 29; 9(418)] and others [Franco et al. Mol Ther. 2005 November; 12(5):876-84] have shown that restriction of native hGAA transgene expression to hepatocytes prevents the development of anti-hGAA immunity and provides stable immunological tolerance to the transgene product. To evaluate the immunological properties of the hybrid liver-muscle and liver-neuron promoters of the invention, we delivered AAV9 vectors encoding native hGAA systemically to adult immunocompetent Gaa−/− mice (vector dose: $2\times10^{12}$ vg/kg) and evaluated anti-hGAA humoral immune responses (FIG. 18). Adult Gaa−/− mice were specifically used in these experiments as neonate animals have been reported to be more prone to develop pro-tolerogenic responses. At early time points after treatment, high anti-hGAA IgG were induced in mice treated with the Enh.C5.12 vector in addition to the control CAG and C5.12 vectors (FIG. 18A). Conversely, anti-hGAA IgG measured at early times points in mice treated with LiMP, LiNeuP and control hAAT vectors (FIG. 18A) were either low or absent and significantly different from those measured in the CAG cohort (FIG. 18A). The use of the hybrid promoters LiMP and LiNeuP prevented the induction of anti-hGAA IgG long-term (FIG. 18B). Conversely, antihGAA IgG peaked with time in the C5.12 cohort leading to significantly higher levels than those measured in the other cohorts (FIG. 18B). The reduced humoral immune response observed with Enh.C5.12 compared to C5.12 suggests the increased transgene expression in the liver achieved by using the ApoE enhancer (FIG. 4B, liver) allow to reduce anti-GAA immunity long term (FIG. 5A, FIG. 18). Interestingly, these data suggest that liver transgene expression determined by the CAG and Enh.C5.12 promoters may reduce but not prevent anti-hGAA humoral immune responses (FIG. 18 A-B). VGCN showed no important impact of vector genomes on liver transduction (FIG. 18C).

X. TRANSCRIPTIONAL ACTIVITY OF THE LIVER/MUSCLE LIMP PROMOTER IN HUMAN MYOBLASTS IN VITRO

The transcriptional activity of the liver/muscle promoter LiMP was further confirmed in human myoblasts in vitro (FIG. 19).

VI. CONCLUSION

In the present study, we showed that hybrid regulatory elements allowed to overcome the limitation of persistence of transgene expression mediated by AAV gene transfer. In particular, we demonstrated that systemic AAV gene therapy with the LIMP promoter resulted in superior therapeutic efficacy compared to single tissue promoters (liver-specific, hAAT, or muscle-specific, C5.12) in Gaa−/− mice treated as neonates. In this model, we observed long-term complete rescue of the disease phenotype, including clearance of pathological glycogen accumulation whole-body and significant rescue cardiac hypertrophy and muscle strength. These results were achieved using AAV vector doses 10-50 times lower than those currently used in other studies in newborn animals and in ongoing clinical trials for other lethal neuromuscular diseases. These findings support the future application of this AAV gene therapy approach to infantile onset Pompe disease. Based on their favorable safety and efficacy profile, dual promoters may provide a significant advantage in the development of gene-based therapies for the treatment of several other diseases with systemic, multiple organ involvement and early lethality.

The invention claimed is:

1. A nucleic acid sequence comprising:
   (i) a first transcription regulatory element capable of driving or enhancing tissue-selective expression in a first tissue, wherein said first tissue is the liver; and
   (ii) a second transcription regulatory element capable of driving or enhancing tissue-selective expression in a second tissue, wherein said second tissue is not the liver;
   wherein the first and second transcription regulatory elements are fused together; and
   wherein the second transcription regulatory element is a muscle-selective promoter;
   wherein the first transcription regulatory element is a combination of ApoE enhancer and alpha-1 antitrypsin (hAAT) promoter; and
   wherein the second transcription regulatory element is spC5.12 promoter.

2. An expression cassette comprising the nucleic acid sequence according to claim 1 and a transgene of interest.

3. A vector comprising the expression cassette according to claim 2.

4. The vector according to claim 3, wherein said vector is a viral vector selected from an adenovirus vector, a retrovirus vector, a lentivirus vector and an AAV vector.

5. An isolated cell transformed with the nucleic acid sequence according to claim 1, an expression cassette comprising said nucleic acid sequence, or a vector comprising said expression cassette.

6. A pharmaceutical composition comprising the vector according to claim 3.

7. A pharmaceutical composition comprising the isolated cell according to claim 5.

8. A method of treating a disorder by gene therapy comprising expression of a therapeutic transgene in a tissue of therapeutic interest, said method comprising administering an expression cassette, a vector or a cell comprising the nucleic acid sequence according to claim 1 to a subject in need of treatment.

9. The method according to claim 8, wherein the disorder is selected from the group consisting of:

a lysosomal storage disease (LSD), a metabolic disease, a neuromuscular disorder and other diseases.

10. The method according to claim 9, wherein the disorder is a glycogen storage disease selected from Pompe disease, infantile onset Pompe disease and late onset Pompe disease.

11. The method according to claim 9, wherein:

the lysosomal storage disease (LSD) is mucopolysaccharidosis type I to VII (MPSI-VII), Sandhoff disease or Tay-Sachs;

the metabolic disease is Maple syrup disease (MSUD), Methylmalonic academia (MMA), glycogenosis type I and III (GSDI and III), Niemann-Pick disease (NPC), Canavan disease, or Phenylketonuria (PKU);

the neuromuscular disorder is a muscular dystrophy, myotonic dystrophy (Steinert disease), Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy, a motor neuron disease, amyotrophic lateral sclerosis (ALS), spinal muscular atrophy, Infantile progressive spinal muscular atrophy type 1 (Werdnig-Hoffmann disease), intermediate spinal muscular atrophy (Type 2), juvenile spinal muscular atrophy (Type 3, Kugelberg-Welander disease), adult spinal muscular atrophy (Type 4), spinal-bulbar muscular atrophy (Kennedy disease), an inflammatory myopathy, polymyositis dermatomyositis, inclusion-body myositis, neuromuscular junction disease, myasthenia gravis, Lambert-Eaton (myasthenic) syndrome, congenital myasthenic syndromes, diseases of peripheral nerve, Charcot-Marie-Tooth disease, Friedreich's ataxia, Dejerine-Sottas disease, metabolic diseases of muscle, phosphorylase deficiency (McArdle disease), acid maltase deficiency (Pompe disease), phosphofructokinase deficiency (Tarui disease), debrancher enzyme deficiency (Cori or Forbes disease), mitochondrial myopathy, carnitine deficiency, carnitine palmityl transferase deficiency, phosphogly cerate kinase deficiency, phosphoglycerate mutase deficiency, lactate dehydrogenase deficiency, myoadenylate deaminase deficiency, myopathies due to endocrine abnormalities, hyperthyroid myopathy, hypothyroid myopathy, and other myopathies, myotonia congenita paramyotonia congenita, central core disease, nemaline myopathy, myotubular myopathy or periodic paralysis; and other diseases are hemophilia A, MPSI, Alzheimer's Disease, Parkinson's Disease, Huntington's Disease, Tourette Syndrome, schizophrenia, Sly disease, Hunter's disease, dementia, paranoia, obsessive compulsive disorder, learning disabilities, ALS, Charcot-Marie Tooth disease, Kennedy's disease, glioblastoma, neuroblastoma, autism, Gaucher's disease, Hurler's disease, Krabbe's disease, altered behaviors, or disorders in sleeping, perception or cognition.

12. The nucleic acid sequence according to claim 1, comprising a combination of ApoE enhancer of SEQ ID NO:4, hAAT promoter of SEQ ID NO:2 and spC5.12 promoter of SEQ ID NO:1.

13. The nucleic acid sequence according to claim 1, consisting of the sequence of SEQ ID NO:6.

* * * * *